United States Patent
Faulks et al.

(10) Patent No.: US 11,688,511 B2
(45) Date of Patent: Jun. 27, 2023

(54) CAREGIVER AND STAFF INFORMATION SYSTEM

(71) Applicant: Hill-Rom Services, Inc., Batesville, IN (US)

(72) Inventors: Sherrod L. Faulks, Durham, NC (US); Elizabeth A. Kowal, Cary, NC (US); David M. Girardeau, Pittsboro, IN (US); Bartholomew F. Sferrazza, Holly Springs, NC (US); John Moulson, Raleigh, NC (US); Dino R. Bostic, Cary, NC (US); Darren S. Hudgins, Cary, NC (US); Adam Drufke, Cary, NC (US); Ronald W. Taylor, Morrisville, NC (US); Collin Davidson, Apex, NC (US); Jennifer A. Gunn, Durham, NC (US); John S. Schroder, Apex, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 17/578,878

(22) Filed: Jan. 19, 2022

(65) Prior Publication Data
US 2022/0139540 A1    May 5, 2022

Related U.S. Application Data

(63) Continuation of application No. 17/176,234, filed on Feb. 16, 2021, now Pat. No. 11,257,588, which is a
(Continued)

(51) Int. Cl.
*G16H 40/20* (2018.01)
*G08B 21/18* (2006.01)
(Continued)

(52) U.S. Cl.
CPC ............ *G16H 40/20* (2018.01); *G06Q 10/10* (2013.01); *G08B 21/04* (2013.01); *G08B 21/18* (2013.01);
(Continued)

(58) Field of Classification Search
CPC ........ G16H 40/20; G16H 80/00; G06Q 10/10; G08B 21/04; G08B 21/18; G08B 27/005; H04L 67/12
See application file for complete search history.

(56) References Cited

U.S. PATENT DOCUMENTS

| | | |
|---|---|---|
| 4,237,344 A | 12/1980 | Moore |
| 4,555,805 A | 11/1985 | Talbot |

(Continued)

FOREIGN PATENT DOCUMENTS

WO    2660744 A1    11/2013

OTHER PUBLICATIONS

Voalté Me for iPhone™ In a Heartbeat v2.x-2012; © Voalte, Inc.; 10 pages.

(Continued)

*Primary Examiner* — An T Nguyen
(74) *Attorney, Agent, or Firm* — Barnes & Thornburg LLP

(57) ABSTRACT

A mobile caregiver application is stored on mobile devices of caregivers for managing alert messages generated by a variety of equipment in a healthcare information system. The mobile caregiver application allows secure voice, text, and, optionally, video communication between caregivers using their mobile devices.

20 Claims, 58 Drawing Sheets

Related U.S. Application Data continuation of application No. 16/143,971, filed on Sep. 27, 2018, now Pat. No. 10,957,445.

(60) Provisional application No. 62/660,576, filed on Apr. 20, 2018, provisional application No. 62/568,671, filed on Oct. 5, 2017.

(51) Int. Cl.
| | | |
|---|---|---|
| *G08B 27/00* | (2006.01) | |
| *H04L 67/12* | (2022.01) | |
| *G08B 21/04* | (2006.01) | |
| *G16H 80/00* | (2018.01) | |
| *G06Q 10/10* | (2023.01) | |

(52) U.S. Cl.
CPC .......... *G08B 27/005* (2013.01); *G16H 80/00* (2018.01); *H04L 67/12* (2013.01)

(56) References Cited

U.S. PATENT DOCUMENTS

| | | | |
|---|---|---|---|
| 4,634,815 A | 1/1987 | Marquis | |
| 4,669,393 A | 6/1987 | Wuthrich | |
| 4,730,715 A | 3/1988 | Siegenthaler | |
| 4,730,821 A | 3/1988 | Fluckiger | |
| 4,731,868 A | 3/1988 | Dreier | |
| 4,735,344 A | 4/1988 | Wuethrich | |
| 4,742,903 A | 5/1988 | Trummer | |
| 4,750,192 A | 6/1988 | Dzung | |
| 4,785,389 A | 11/1988 | Kislovski | |
| 4,793,405 A | 12/1988 | Diggelmann et al. | |
| 4,815,579 A | 3/1989 | Fritz | |
| 4,819,780 A | 4/1989 | Trummer et al. | |
| 4,823,694 A | 4/1989 | Siegenthaler | |
| 4,827,225 A | 5/1989 | Lee | |
| 4,853,686 A | 8/1989 | Kueng et al. | |
| 4,871,125 A | 10/1989 | Haueter | |
| 4,872,185 A | 10/1989 | Braun et al. | |
| 4,887,807 A | 12/1989 | Berger et al. | |
| 4,907,264 A | 3/1990 | Seiler et al. | |
| 4,914,691 A | 4/1990 | Berger | |
| 4,928,273 A | 5/1990 | Protopapas | |
| 4,958,976 A | 9/1990 | Haueter | |
| 4,984,247 A | 1/1991 | Kaufmann et al. | |
| 5,003,593 A | 3/1991 | Mihm, Jr. | |
| 5,003,598 A | 3/1991 | Kunstadt | |
| 5,016,546 A | 5/1991 | Haueter | |
| 5,056,204 A | 10/1991 | Bartschi | |
| 5,081,389 A | 1/1992 | Abbott et al. | |
| 5,170,412 A | 12/1992 | Massey | |
| 5,177,765 A | 1/1993 | Holland et al. | |
| 5,177,766 A | 1/1993 | Holland et al. | |
| 5,181,225 A | 1/1993 | Neeser et al. | |
| 5,203,263 A | 4/1993 | Berger et al. | |
| 5,214,703 A | 5/1993 | Massey et al. | |
| 5,216,691 A | 6/1993 | Kaufmann | |
| 5,220,448 A | 6/1993 | Vogel et al. | |
| 5,227,907 A | 7/1993 | Rao et al. | |
| 5,237,506 A | 8/1993 | Horbal et al. | |
| 5,265,128 A | 11/1993 | Widmer et al. | |
| 5,276,844 A | 1/1994 | Aebi et al. | |
| 5,278,541 A | 1/1994 | Wicht et al. | |
| 5,301,116 A | 4/1994 | Grunig | |
| 5,305,384 A | 4/1994 | Ashby et al. | |
| 5,317,566 A | 5/1994 | Joshi | |
| 5,317,640 A | 5/1994 | Callias | |
| 5,319,355 A | 6/1994 | Russek | |
| 5,319,363 A | 6/1994 | Welch et al. | |
| 5,319,486 A | 6/1994 | Vogel et al. | |
| 5,319,643 A | 6/1994 | Rao et al. | |
| 5,334,952 A | 8/1994 | Maddy et al. | |
| 5,365,233 A | 11/1994 | Schaub | |
| 5,375,118 A | 12/1994 | Rao et al. | |
| 5,383,045 A | 1/1995 | Vogel et al. | |
| 5,384,852 A | 1/1995 | Scharen | |
| 5,389,863 A | 2/1995 | Fluckiger | |
| 5,392,355 A | 2/1995 | Khurana et al. | |
| 5,394,402 A | 2/1995 | Ross | |
| 5,406,470 A | 4/1995 | Ridley et al. | |
| 5,436,935 A | 7/1995 | Bernhard et al. | |
| 5,450,231 A | 9/1995 | Battig et al. | |
| 5,463,622 A | 10/1995 | Keller et al. | |
| 5,467,344 A | 11/1995 | Solomon et al. | |
| 5,478,993 A | 12/1995 | Derksen | |
| 5,493,613 A | 2/1996 | Denno et al. | |
| 5,508,840 A | 4/1996 | Vogel et al. | |
| 5,530,763 A | 6/1996 | Aebi et al. | |
| 5,534,851 A | 7/1996 | Russek | |
| 5,557,653 A | 9/1996 | Paterson et al. | |
| 5,559,992 A | 9/1996 | Stutz et al. | |
| 5,561,412 A | 10/1996 | Novak et al. | |
| 5,568,478 A | 10/1996 | van Loo, Jr. et al. | |
| 5,570,354 A | 10/1996 | Simon | |
| 5,586,188 A | 12/1996 | Renggli et al. | |
| 5,594,798 A | 1/1997 | Cox et al. | |
| 5,596,638 A | 1/1997 | Paterson et al. | |
| 5,608,762 A | 3/1997 | Maddy | |
| 5,611,527 A | 3/1997 | Wuthrich | |
| 5,615,230 A | 3/1997 | Gunther et al. | |
| 5,615,995 A | 4/1997 | Nobile et al. | |
| 5,625,839 A | 4/1997 | Kohler et al. | |
| 5,628,258 A | 5/1997 | Zwahlen et al. | |
| 5,634,000 A | 5/1997 | Wicht | |
| 5,673,307 A | 9/1997 | Holland et al. | |
| 5,686,391 A | 11/1997 | Crudden | |
| 5,687,217 A | 11/1997 | Bliss et al. | |
| 5,689,098 A | 11/1997 | Gillieron | |
| 5,699,038 A | 12/1997 | Ulrich et al. | |
| 5,701,193 A | 12/1997 | Vogel et al. | |
| 5,768,272 A | 6/1998 | Rao et al. | |
| 5,778,244 A | 7/1998 | Putnins et al. | |
| 5,787,077 A | 7/1998 | Kuehnel et al. | |
| 5,794,163 A | 8/1998 | Paterson et al. | |
| 5,805,590 A | 9/1998 | Gillard et al. | |
| 5,805,690 A | 9/1998 | Koepper et al. | |
| 5,809,258 A | 9/1998 | Bemanian et al. | |
| 5,825,779 A | 10/1998 | Putnins et al. | |
| 5,838,223 A | 11/1998 | Gallant et al. | |
| 5,841,246 A | 11/1998 | Manders | |
| 5,857,087 A | 1/1999 | Bemanian et al. | |
| 5,859,857 A | 1/1999 | Martinson et al. | |
| 5,867,813 A | 2/1999 | Di Pietro et al. | |
| 5,877,675 A | 3/1999 | Rebstock et al. | |
| 5,896,511 A | 4/1999 | Manning et al. | |
| 5,898,671 A | 4/1999 | Hunt et al. | |
| 5,903,571 A | 5/1999 | Koepper et al. | |
| 5,907,542 A | 5/1999 | Kuehnel et al. | |
| 5,920,263 A * | 7/1999 | Huttenhoff ............... | G08B 5/36 340/573.1 |
| 5,926,511 A | 7/1999 | Fleischmann | |
| 5,928,376 A | 7/1999 | Dettmar et al. | |
| 5,942,986 A | 8/1999 | Shabot et al. | |
| 5,942,996 A | 8/1999 | Scarangella et al. | |
| 5,943,020 A | 8/1999 | Liebendoerfer et al. | |
| 5,975,273 A | 11/1999 | Zwahlen et al. | |
| 5,983,260 A | 11/1999 | Hauser et al. | |
| 5,991,298 A | 11/1999 | Hunt et al. | |
| 5,995,572 A | 11/1999 | Dettmar | |
| 5,999,846 A | 12/1999 | Pardey et al. | |
| 6,014,384 A | 1/2000 | Weberhofer | |
| 6,025,791 A | 2/2000 | Tonks | |
| 6,044,158 A | 3/2000 | Terpening et al. | |
| 6,046,918 A | 4/2000 | Jitaru | |
| 6,061,256 A | 5/2000 | Kolar | |
| 6,104,723 A | 8/2000 | Martinson et al. | |
| 6,141,346 A | 10/2000 | Caldara et al. | |
| 6,147,592 A | 11/2000 | Ulrich et al. | |
| 6,212,384 B1 | 4/2001 | Almgren et al. | |
| 6,240,078 B1 | 5/2001 | Kuhnel et al. | |
| 6,243,844 B1 | 6/2001 | Tonks | |
| 6,256,674 B1 | 7/2001 | Manning et al. | |
| 6,257,389 B1 | 7/2001 | Paping et al. | |
| 6,264,020 B1 | 7/2001 | Rufener et al. | |

(56) References Cited

U.S. PATENT DOCUMENTS

| | | |
|---|---|---|
| 6,272,633 B1 | 8/2001 | Duke et al. |
| 6,315,462 B1 | 11/2001 | Anthamatten et al. |
| 6,332,100 B1 | 12/2001 | Sahai et al. |
| 6,345,784 B1 | 2/2002 | Shnaps |
| 6,356,638 B1 | 3/2002 | Hardy et al. |
| 6,356,762 B1 | 3/2002 | Guenther |
| 6,362,725 B1 | 3/2002 | Ulrich et al. |
| 6,373,209 B1 | 4/2002 | Gerber et al. |
| 6,385,444 B1 | 5/2002 | Peschel et al. |
| 6,415,412 B2 | 7/2002 | Tonks |
| 6,426,957 B1 | 7/2002 | Hauser et al. |
| 6,427,133 B1 | 7/2002 | Paping et al. |
| 6,470,033 B1 | 10/2002 | Menzi et al. |
| 6,474,592 B1 | 11/2002 | Shnaps |
| 6,496,499 B1 | 12/2002 | Hamilton et al. |
| 6,539,025 B1 | 3/2003 | Manning et al. |
| 6,581,841 B1 | 3/2003 | Christoffersen |
| 6,616,140 B2 | 9/2003 | Siegenthaler |
| 6,618,797 B1 | 9/2003 | Dery et al. |
| 6,628,323 B1 | 9/2003 | Wegmann |
| 6,651,041 B1 | 11/2003 | Juric |
| 6,700,806 B2 | 3/2004 | Kolar |
| 6,754,516 B2 | 6/2004 | Mannheimer |
| 6,755,503 B2 | 6/2004 | von Niederhausern et al. |
| 6,768,771 B1 | 7/2004 | Costantini |
| 6,771,775 B1 | 8/2004 | Widmer |
| 6,782,102 B2 | 8/2004 | Blanchard et al. |
| 6,804,656 B1 | 10/2004 | Rosenfeld et al. |
| 6,862,201 B2 | 3/2005 | Hodge, Jr. |
| 6,892,083 B2 | 5/2005 | Shostak |
| 6,897,780 B1 | 5/2005 | Ulrich et al. |
| 6,900,824 B2 | 5/2005 | Glaeser |
| 6,901,255 B2 | 5/2005 | Shostak |
| 6,928,370 B2 | 8/2005 | Anuzis et al. |
| 6,944,448 B1 | 9/2005 | Bobst |
| 6,952,159 B1 | 10/2005 | Müller |
| 6,963,650 B2 | 11/2005 | Combest |
| 6,967,553 B2 | 11/2005 | Jitaru |
| 7,003,278 B2 | 2/2006 | Beni et al. |
| 7,009,850 B2 | 3/2006 | Jitaru |
| 7,012,820 B2 | 3/2006 | Jitaru |
| 7,015,699 B1 | 3/2006 | Suntio |
| 7,035,622 B2 | 4/2006 | Pappalardo et al. |
| 7,035,623 B2 | 4/2006 | Pappalardo et al. |
| 7,090,053 B2 | 8/2006 | Bothwell et al. |
| 7,091,817 B2 | 8/2006 | Peck et al. |
| 7,093,823 B2 | 8/2006 | Sevalie' |
| 7,123,950 B2 | 10/2006 | Mannheimer |
| 7,130,203 B2 | 10/2006 | Mbaye |
| 7,190,802 B2 | 3/2007 | Rains et al. |
| 7,206,594 B2 | 4/2007 | Shostak |
| 7,212,815 B1 | 5/2007 | Juric |
| 7,215,945 B2 | 5/2007 | Pappalardo et al. |
| 7,218,710 B1 | 5/2007 | Ali et al. |
| 7,224,281 B2 | 5/2007 | Santoso et al. |
| 7,225,408 B2 | 5/2007 | O'Rourke |
| 7,242,308 B2 | 7/2007 | Ulrich et al. |
| 7,248,881 B2 | 7/2007 | Shostak |
| 7,249,036 B2 | 7/2007 | Bayne |
| 7,256,708 B2 | 8/2007 | Rosenfeld et al. |
| 7,257,415 B2 | 8/2007 | Shostak |
| 7,263,669 B2 | 8/2007 | Denholm |
| 7,286,472 B2 | 10/2007 | Wu |
| 7,295,094 B2 | 11/2007 | Jitaru et al. |
| 7,301,451 B2 | 11/2007 | Hastings |
| 7,307,543 B2 | 12/2007 | Rosenfeld et al. |
| 7,308,718 B1 | 12/2007 | Brookner |
| 7,310,541 B2 | 12/2007 | Shostak |
| 7,315,825 B2 | 1/2008 | Rosenfeld et al. |
| 7,319,386 B2 | 1/2008 | Collins, Jr. et al. |
| 7,321,862 B2 | 1/2008 | Rosenfeld et al. |
| 7,379,405 B2 | 5/2008 | Chang |
| 7,408,793 B2 | 8/2008 | Jitaru et al. |
| 7,428,189 B2 | 9/2008 | Hubicki |
| 7,430,692 B2 | 9/2008 | White, III et al. |
| 7,436,311 B2 | 10/2008 | Rapaport et al. |
| 7,450,402 B2 | 11/2008 | Jitaru |
| 7,454,359 B2 | 11/2008 | Rosenfeld et al. |
| 7,457,751 B2 | 11/2008 | Shostak |
| 7,471,685 B2 | 12/2008 | Wu |
| 7,475,019 B2 | 1/2009 | Rosenfeld et al. |
| 7,538,659 B2 | 5/2009 | Ulrich et al. |
| 7,542,759 B2 | 6/2009 | Edward et al. |
| 7,545,786 B2 | 6/2009 | Krahn et al. |
| 7,558,082 B2 | 7/2009 | Jitaru |
| 7,571,317 B1 | 8/2009 | Vilhuber |
| 7,616,616 B2 | 11/2009 | Amann et al. |
| 7,657,849 B2 | 2/2010 | Chaudhri et al. |
| 7,675,190 B1 | 3/2010 | Müller et al. |
| 7,716,491 B2 | 5/2010 | Brookner et al. |
| 7,737,827 B2 | 6/2010 | Perkins et al. |
| 7,746,218 B2 | 6/2010 | Collins, Jr. et al. |
| 7,747,021 B2 | 6/2010 | Lindteigen et al. |
| 7,756,728 B2 | 7/2010 | Maughan et al. |
| 7,764,518 B2 | 7/2010 | Jitaru |
| 7,764,972 B2 | 7/2010 | Shostak |
| 7,769,054 B2 | 8/2010 | Hamilton |
| 7,769,598 B2 | 8/2010 | Denholm |
| 7,769,694 B2 | 8/2010 | Schwartz et al. |
| 7,813,744 B2 | 10/2010 | Johnson |
| 7,818,263 B2 | 10/2010 | Schwartz et al. |
| 7,822,017 B2 | 10/2010 | D'Souza et al. |
| 7,848,270 B2 | 12/2010 | Hilmersson |
| 7,852,831 B2 | 12/2010 | Akbar |
| 7,853,537 B2 | 12/2010 | Moy et al. |
| 7,904,312 B2 | 3/2011 | Denholm |
| 7,916,871 B2 | 3/2011 | Brookner et al. |
| 7,953,070 B1 | 5/2011 | Agarwal et al. |
| 7,953,447 B2 | 5/2011 | Shostak |
| 7,958,201 B2 | 6/2011 | Lindsay |
| 7,978,619 B2 | 7/2011 | Nielsen |
| 7,981,032 B2 | 7/2011 | Santoso et al. |
| 8,015,030 B2 | 9/2011 | Brown |
| 8,046,721 B2 | 10/2011 | Chaudhri et al. |
| 8,092,380 B2 | 1/2012 | Rothman et al. |
| 8,098,806 B2 | 1/2012 | Shostak |
| 8,100,829 B2 | 1/2012 | Rothman et al. |
| 8,112,278 B2 | 2/2012 | Burke |
| 8,115,640 B2 | 2/2012 | Walls |
| 8,121,649 B2 | 2/2012 | Shostak |
| 8,122,006 B2 | 2/2012 | de Castro Alves et al. |
| 8,131,259 B2 | 3/2012 | Haynes et al. |
| 8,160,895 B2 | 4/2012 | Schmitt et al. |
| 8,165,893 B1 | 4/2012 | Goldberg et al. |
| 8,170,887 B2 | 5/2012 | Rosenfeld et al. |
| 8,175,887 B2 | 5/2012 | Shostak |
| 8,175,895 B2 | 5/2012 | Rosenfeld et al. |
| 8,183,987 B2 | 5/2012 | Traughber et al. |
| 8,223,715 B2 | 7/2012 | Hamilton et al. |
| 8,250,483 B2 | 8/2012 | Blomquist |
| 8,255,238 B2 | 8/2012 | Powell et al. |
| 8,283,814 B2 | 10/2012 | Liao |
| 8,286,171 B2 | 10/2012 | More et al. |
| 8,332,017 B2 | 12/2012 | Tarassenko et al. |
| 8,346,572 B2 | 1/2013 | Eaton, Jr. et al. |
| 8,355,925 B2 | 1/2013 | Rothman et al. |
| 8,374,988 B2 | 2/2013 | Gawlick |
| 8,401,606 B2 | 3/2013 | Mannheimer |
| 8,401,607 B2 | 3/2013 | Mannheimer |
| 8,403,847 B2 | 3/2013 | Rothman et al. |
| 8,406,456 B2 | 3/2013 | More |
| 8,416,085 B2 | 4/2013 | Gawlick |
| 8,417,233 B2 | 4/2013 | Woloshyn |
| 8,417,662 B2 | 4/2013 | Gawlick |
| 8,451,101 B2 | 5/2013 | Somasundaram et al. |
| 8,454,506 B2 | 6/2013 | Rothman et al. |
| 8,467,536 B2 | 6/2013 | Lewis et al. |
| 8,478,695 B2 | 7/2013 | Simcik et al. |
| 8,494,868 B2 | 7/2013 | Saalsaa |
| 8,498,865 B1 | 7/2013 | Shostak |
| 8,503,621 B2 | 8/2013 | Patel et al. |
| 8,525,687 B2 | 9/2013 | Tran |
| 8,543,066 B2 | 9/2013 | Marklund et al. |
| 8,543,534 B2 | 9/2013 | Alves et al. |

(56) References Cited

U.S. PATENT DOCUMENTS

| | | |
|---|---|---|
| 8,612,248 B2 | 12/2013 | Denholm |
| 8,615,291 B2 | 12/2013 | Moorman et al. |
| 8,618,927 B2 | 12/2013 | Wohlert |
| 8,619,610 B2 | 12/2013 | Simha et al. |
| 8,620,020 B2 | 12/2013 | More |
| 8,626,246 B2 | 1/2014 | Shostak |
| 8,681,989 B2 | 3/2014 | Park et al. |
| 8,708,903 B2 | 4/2014 | Tran |
| 8,737,209 B2 | 5/2014 | Ivanov et al. |
| 8,756,528 B2 | 6/2014 | Cristofoli |
| 8,775,196 B2 | 7/2014 | Simpson et al. |
| 8,825,508 B2 | 9/2014 | Nilsson |
| 8,838,196 B2 | 9/2014 | Mannheimer |
| 8,842,001 B2 | 9/2014 | Gilham et al. |
| 8,849,718 B2 | 9/2014 | Dala et al. |
| 8,856,729 B2 | 10/2014 | Moore et al. |
| 8,886,663 B2 | 11/2014 | Gainsboro et al. |
| 8,886,792 B2 | 11/2014 | Biondi et al. |
| 8,890,656 B2 | 11/2014 | Pendse |
| 8,918,304 B2 | 12/2014 | Le et al. |
| 8,933,820 B1 | 1/2015 | Tyson et al. |
| 8,942,671 B2 | 1/2015 | Haynes et al. |
| 8,948,734 B2 | 2/2015 | Vaglio et al. |
| 8,949,738 B2 | 2/2015 | Felt |
| 8,977,548 B2 | 3/2015 | Shostak |
| 9,019,099 B2 | 4/2015 | Fox et al. |
| 9,020,476 B2 | 4/2015 | Leipzig et al. |
| 9,020,547 B2 | 4/2015 | Amann et al. |
| 9,052,809 B2 | 6/2015 | Vesto |
| 9,058,741 B2 | 6/2015 | Steinhauer et al. |
| 9,059,971 B2 | 6/2015 | Graham et al. |
| 9,098,604 B2 | 8/2015 | Treacy |
| 9,098,696 B2 | 8/2015 | Johnson et al. |
| 9,124,386 B2 | 9/2015 | Dadu et al. |
| 9,129,501 B1 | 9/2015 | King et al. |
| 9,137,267 B2 | 9/2015 | Patel et al. |
| 9,137,405 B2 | 9/2015 | Eschbach et al. |
| 9,159,313 B2 | 10/2015 | Saeki et al. |
| 9,166,977 B2 | 10/2015 | Desai et al. |
| 9,167,445 B2 | 10/2015 | Hedlund et al. |
| 9,185,202 B2 | 11/2015 | Herbst et al. |
| 9,185,578 B2 | 11/2015 | Hedlund et al. |
| 9,185,579 B2 | 11/2015 | Hedlund et al. |
| 9,215,583 B2 | 12/2015 | Shostak |
| 9,218,454 B2 | 12/2015 | Kiani et al. |
| 9,241,066 B2 | 1/2016 | Wong et al. |
| 9,246,991 B2 | 1/2016 | Moore et al. |
| 9,258,143 B2 | 2/2016 | Chavez |
| 9,280,637 B2 | 3/2016 | Vaglio et al. |
| 9,305,450 B2 | 4/2016 | Halverson et al. |
| 9,355,214 B2 | 5/2016 | Wilson et al. |
| 9,361,769 B2 | 6/2016 | Taughber et al. |
| 9,400,874 B2 | 7/2016 | Powell et al. |
| 9,432,072 B2 | 8/2016 | Karlsson |
| 9,449,355 B2 | 9/2016 | Kozicki et al. |
| 9,492,341 B2 | 11/2016 | Huster |
| 9,521,552 B2 | 12/2016 | Adrangi et al. |
| 9,524,569 B2 | 12/2016 | Moore et al. |
| 9,582,978 B2 | 2/2017 | Herbst et al. |
| 9,585,565 B2 | 3/2017 | Carnes |
| 9,621,348 B2 | 4/2017 | Bahjat |
| 9,626,479 B2 | 4/2017 | Zaleski |
| 9,633,088 B1 | 4/2017 | Nagy et al. |
| 9,637,133 B1 * | 5/2017 | McCusker ......... A61B 5/02055 |
| 9,649,073 B2 | 5/2017 | King et al. |
| 9,654,448 B2 | 5/2017 | Cummings et al. |
| 9,659,482 B2 | 5/2017 | Yang |
| 9,667,491 B2 | 5/2017 | Piekarski et al. |
| 9,706,966 B2 | 7/2017 | Colman et al. |
| 9,722,775 B2 | 8/2017 | Hjelm et al. |
| 9,734,301 B2 | 8/2017 | King et al. |
| 9,747,778 B2 | 8/2017 | Mukherji et al. |
| 9,749,825 B2 | 8/2017 | Payne et al. |
| 9,750,872 B2 | 9/2017 | De La Huerga |
| 9,779,209 B2 | 10/2017 | Greer |
| 9,805,573 B2 | 10/2017 | Herbst et al. |
| 9,817,809 B2 | 11/2017 | Shostak |
| 9,819,651 B2 | 11/2017 | Mahler |
| 9,824,312 B2 | 11/2017 | Fletcher et al. |
| 9,830,801 B2 | 11/2017 | Rusin et al. |
| 9,833,194 B2 | 12/2017 | Hayes et al. |
| 9,836,940 B2 | 12/2017 | Herbst et al. |
| 9,838,062 B2 | 12/2017 | Larsen |
| 9,872,148 B2 | 1/2018 | King et al. |
| 9,881,475 B2 | 1/2018 | Herbst et al. |
| 9,911,300 B2 | 3/2018 | Herbst et al. |
| 9,916,420 B2 | 3/2018 | Cardoza et al. |
| 9,924,908 B2 | 3/2018 | Hubert et al. |
| 9,928,379 B1 | 3/2018 | Hoffer |
| 9,946,711 B2 | 4/2018 | Reiter et al. |
| 9,946,984 B2 | 4/2018 | Ahari et al. |
| 9,990,827 B2 | 6/2018 | Vaddepally |
| 9,996,667 B2 | 6/2018 | Moore et al. |
| 10,037,411 B2 | 7/2018 | Bala et al. |
| 10,042,979 B2 | 8/2018 | Moore et al. |
| 10,068,057 B2 | 9/2018 | Moore |
| 10,078,875 B2 | 9/2018 | Powell et al. |
| 10,098,593 B2 | 10/2018 | Collins, Jr. et al. |
| 10,115,171 B2 | 10/2018 | Portnoy |
| 10,121,346 B2 | 11/2018 | Herbst et al. |
| 10,232,139 B1 * | 3/2019 | Hang ................ A61M 21/02 |
| 10,957,445 B2 | 3/2021 | Faulks et al. |
| 11,257,588 B2 | 2/2022 | Faulks et al. |
| 2001/0014161 A1 | 8/2001 | Baiker et al. |
| 2001/0029489 A1 | 10/2001 | Brookner et al. |
| 2001/0031650 A1 | 10/2001 | Baiker et al. |
| 2001/0047278 A1 | 11/2001 | Brookner et al. |
| 2002/0007316 A1 | 1/2002 | Frank |
| 2002/0010640 A1 | 1/2002 | Dutta et al. |
| 2002/0040282 A1 | 4/2002 | Bailey et al. |
| 2002/0060164 A1 | 5/2002 | LeMoine et al. |
| 2002/0070258 A1 | 6/2002 | LeMoine et al. |
| 2002/0077991 A1 | 6/2002 | Heimann et al. |
| 2002/0083019 A1 | 6/2002 | Bystrak et al. |
| 2002/0083023 A1 | 6/2002 | Rosenkranz et al. |
| 2002/0126310 A1 | 9/2002 | Hersberger et al. |
| 2002/0128986 A1 | 9/2002 | Stutz |
| 2002/0133471 A1 | 9/2002 | Eskandari et al. |
| 2002/0140162 A1 | 10/2002 | Gasser et al. |
| 2002/0143713 A1 | 10/2002 | Stutz |
| 2002/0169728 A1 | 11/2002 | Moy et al. |
| 2002/0178130 A1 | 11/2002 | Moy et al. |
| 2002/0191585 A1 | 12/2002 | Wu |
| 2002/0193132 A1 | 12/2002 | Wu |
| 2003/0004900 A1 | 1/2003 | Schwartz et al. |
| 2003/0029294 A1 | 2/2003 | Lay et al. |
| 2003/0074324 A1 | 4/2003 | Kresina et al. |
| 2003/0097337 A1 | 5/2003 | Brookner et al. |
| 2003/0191730 A1 | 10/2003 | Adkins et al. |
| 2004/0043797 A1 | 3/2004 | Shostak |
| 2004/0073453 A1 | 4/2004 | Nenov et al. |
| 2004/0082454 A1 | 4/2004 | White et al. |
| 2004/0107163 A1 | 6/2004 | Dutta et al. |
| 2005/0023409 A1 | 2/2005 | Shnaps et al. |
| 2005/0065817 A1 | 3/2005 | Mihai et al. |
| 2005/0077357 A1 | 4/2005 | Roux |
| 2005/0122682 A1 | 6/2005 | Streit et al. |
| 2005/0124350 A1 | 6/2005 | Wu |
| 2005/0146431 A1 | 7/2005 | Hastings et al. |
| 2005/0165321 A1 * | 7/2005 | Fischell .............. A61B 5/349 |
| | | 600/515 |
| 2006/0016881 A1 | 1/2006 | Roux |
| 2006/0091204 A1 | 5/2006 | Gal |
| 2006/0094439 A1 | 5/2006 | Christian |
| 2006/0097033 A1 | 5/2006 | Le Gal |
| 2006/0157567 A1 | 7/2006 | Baumann et al. |
| 2006/0168259 A1 | 7/2006 | Spilotro et al. |
| 2006/0187868 A1 | 8/2006 | Pearce et al. |
| 2007/0004971 A1 | 1/2007 | Riley et al. |
| 2007/0033074 A1 * | 2/2007 | Nitzan ................ G16H 50/50 |
| | | 705/3 |
| 2007/0142076 A1 | 6/2007 | Sjostedt |
| 2007/0150726 A1 | 6/2007 | Sinnreich et al. |
| 2007/0210917 A1 | 9/2007 | Collins, Jr. et al. |

(56) References Cited

U.S. PATENT DOCUMENTS

| | | |
|---|---|---|
| 2007/0239488 A1 | 10/2007 | DeRosso |
| 2007/0257577 A1 | 11/2007 | Bizjak |
| 2007/0271606 A1 | 11/2007 | Amann et al. |
| 2007/0281748 A1 | 12/2007 | Piekarski |
| 2007/0298782 A1 | 12/2007 | Wu |
| 2008/0004499 A1* | 1/2008 | Davis ............... G16H 40/63 600/300 |
| 2008/0039071 A1 | 2/2008 | Pearce et al. |
| 2008/0096506 A1 | 4/2008 | Nguyen et al. |
| 2008/0125080 A1 | 5/2008 | Phillips |
| 2008/0153509 A1 | 6/2008 | Piekarski |
| 2008/0183814 A1* | 7/2008 | Sanghavi ............ G06Q 10/107 709/204 |
| 2008/0201429 A1 | 8/2008 | Barbell et al. |
| 2009/0113933 A1 | 5/2009 | Hatem |
| 2009/0212925 A1 | 8/2009 | Schuman, Sr. et al. |
| 2009/0212926 A1 | 8/2009 | Du et al. |
| 2009/0212956 A1* | 8/2009 | Schuman ............ H04L 67/18 340/573.1 |
| 2009/0214009 A1 | 8/2009 | Schuman, Sr. et al. |
| 2009/0217080 A1 | 8/2009 | Ferguson et al. |
| 2010/0001838 A1 | 1/2010 | Miodownik et al. |
| 2010/0058409 A1 | 3/2010 | Chapman et al. |
| 2010/0137693 A1 | 6/2010 | Porras et al. |
| 2010/0223071 A1 | 9/2010 | Kland et al. |
| 2010/0235782 A1 | 9/2010 | Powell et al. |
| 2011/0054924 A1 | 3/2011 | Mitchell et al. |
| 2011/0054946 A1 | 3/2011 | Coulter et al. |
| 2011/0246235 A1 | 10/2011 | Powell et al. |
| 2011/0295621 A1 | 12/2011 | Farooq et al. |
| 2011/0302408 A1 | 12/2011 | McDermott et al. |
| 2011/0302957 A1 | 12/2011 | Hatem |
| 2012/0075674 A1 | 3/2012 | Sweeney |
| 2012/0095779 A1* | 4/2012 | Wengrovitz ........... G16H 40/67 705/3 |
| 2012/0101847 A1 | 4/2012 | Johnson et al. |
| 2012/0169467 A1* | 7/2012 | Condra ............... G16H 40/20 340/8.1 |
| 2012/0194520 A1 | 8/2012 | Nordfelth et al. |
| 2012/0208522 A1 | 8/2012 | Marklund et al. |
| 2012/0209649 A1 | 8/2012 | Ovenden et al. |
| 2012/0284040 A1 | 11/2012 | Dupin |
| 2013/0014058 A1* | 1/2013 | Scothern ............... G06F 3/0481 715/835 |
| 2013/0015967 A1* | 1/2013 | Nagathil ............ G05B 23/0272 340/506 |
| 2013/0074198 A1 | 3/2013 | More et al. |
| 2013/0085765 A1 | 4/2013 | Tuchinda et al. |
| 2013/0085798 A1 | 4/2013 | Spatola et al. |
| 2013/0096953 A1 | 4/2013 | Beverly et al. |
| 2013/0103768 A1 | 4/2013 | Freebeck |
| 2013/0183923 A1 | 7/2013 | Brackett et al. |
| 2013/0271469 A1 | 10/2013 | Moore et al. |
| 2013/0275145 A1 | 10/2013 | Moore et al. |
| 2013/0275151 A1 | 10/2013 | Moore et al. |
| 2013/0275152 A1 | 10/2013 | Moore et al. |
| 2014/0019901 A1 | 1/2014 | Powell et al. |
| 2014/0039351 A1 | 2/2014 | Mix et al. |
| 2014/0051399 A1 | 2/2014 | Walker et al. |
| 2014/0056143 A1 | 2/2014 | Hedlund et al. |
| 2014/0056157 A1 | 2/2014 | Hedlund et al. |
| 2014/0056159 A1 | 2/2014 | Hedlund et al. |
| 2014/0056234 A1 | 2/2014 | Hedlund et al. |
| 2014/0070939 A1 | 3/2014 | Halverson et al. |
| 2014/0097961 A1* | 4/2014 | Vaglio ............... H04W 4/16 340/691.6 |
| 2014/0100873 A1 | 4/2014 | Vaglio et al. |
| 2014/0129255 A1 | 5/2014 | Woodson et al. |
| 2014/0142963 A1* | 5/2014 | Hill ................ G16H 10/60 705/2 |
| 2014/0172996 A1 | 6/2014 | Deeter et al. |
| 2014/0184408 A1* | 7/2014 | Herbst ............ G08B 27/006 340/539.12 |
| 2014/0222450 A1 | 8/2014 | Gray et al. |
| 2014/0249854 A1 | 9/2014 | Moore et al. |
| 2014/0249855 A1 | 9/2014 | Moore |
| 2014/0249857 A1 | 9/2014 | Moore |
| 2014/0278486 A1 | 9/2014 | Moore et al. |
| 2014/0278488 A1 | 9/2014 | Moore |
| 2014/0358585 A1 | 12/2014 | Reiner |
| 2015/0025329 A1 | 1/2015 | Amarasingham et al. |
| 2015/0081339 A1 | 3/2015 | Vaglio et al. |
| 2015/0088549 A1 | 3/2015 | Moore et al. |
| 2015/0106121 A1* | 4/2015 | Muhsin ............ G16H 50/30 705/3 |
| 2015/0137968 A1* | 5/2015 | Rusin ............... G08B 25/001 340/506 |
| 2015/0148617 A1 | 5/2015 | Friedman |
| 2015/0180663 A1 | 6/2015 | Kang et al. |
| 2015/0205919 A1 | 7/2015 | Robertson et al. |
| 2015/0269503 A1 | 9/2015 | Ahari et al. |
| 2015/0302539 A1* | 10/2015 | Mazar ............... G08B 21/02 705/3 |
| 2016/0014099 A1 | 1/2016 | Fishkov |
| 2016/0027289 A1 | 1/2016 | Hargis |
| 2016/0044505 A1 | 2/2016 | Nishi et al. |
| 2016/0055299 A1 | 2/2016 | Yarnell |
| 2016/0110040 A1 | 4/2016 | Vaglio et al. |
| 2016/0173503 A1 | 6/2016 | Knight et al. |
| 2016/0180325 A1* | 6/2016 | Davis ............... G06Q 20/10 705/44 |
| 2016/0180681 A1 | 6/2016 | Halverson et al. |
| 2016/0267236 A1 | 9/2016 | Traughber et al. |
| 2016/0284202 A1 | 9/2016 | Traughber et al. |
| 2016/0315898 A1* | 10/2016 | Kaplan ............ G06Q 10/10 |
| 2016/0360160 A1 | 12/2016 | Eizenberg |
| 2017/0004273 A1* | 1/2017 | Mbanefo ........... G16H 80/00 |
| 2017/0024091 A1 | 1/2017 | Hosier, Jr. |
| 2017/0027787 A1 | 2/2017 | Huster et al. |
| 2017/0032093 A1 | 2/2017 | Norton et al. |
| 2017/0039839 A1 | 2/2017 | Halverson |
| 2017/0048323 A1 | 2/2017 | Schlapfer et al. |
| 2017/0098037 A1 | 4/2017 | Agassi et al. |
| 2017/0109018 A1 | 4/2017 | Vaglio et al. |
| 2017/0116385 A1 | 4/2017 | Lauderdale et al. |
| 2017/0139485 A1 | 5/2017 | Fogelmark et al. |
| 2017/0199973 A1 | 7/2017 | Walton et al. |
| 2017/0214701 A1 | 7/2017 | Hasan |
| 2017/0228682 A1 | 8/2017 | Nilsson et al. |
| 2017/0238172 A1 | 8/2017 | Benoit et al. |
| 2017/0249435 A1 | 8/2017 | Lancelot |
| 2017/0265819 A1 | 9/2017 | Colman et al. |
| 2017/0287300 A1* | 10/2017 | Herbst ............ G16H 40/67 |
| 2017/0308650 A1 | 10/2017 | Brill et al. |
| 2017/0329919 A1* | 11/2017 | Govro ............ G16H 40/63 |
| 2017/0343355 A1 | 11/2017 | Tengfjord et al. |
| 2017/0372219 A1 | 12/2017 | Crawford et al. |
| 2018/0102036 A1 | 4/2018 | Herbst et al. |
| 2018/0125414 A1 | 5/2018 | Lafleche et al. |
| 2018/0144814 A1 | 5/2018 | Bright |
| 2018/0153455 A1 | 6/2018 | Guazzi et al. |
| 2018/0261133 A1 | 9/2018 | Hamada et al. |
| 2018/0295186 A1 | 10/2018 | Schlapfer et al. |
| 2018/0351745 A1 | 12/2018 | Hamada et al. |
| 2019/0108908 A1* | 4/2019 | Faulks ............ G16H 80/00 |
| 2020/0099646 A1* | 3/2020 | Kaplan ............ G16H 80/00 |
| 2021/0174948 A1 | 6/2021 | Faulks et al. |

OTHER PUBLICATIONS

Voalté One for iPhone™ User Manual v2.0; 2012; © Voalte, Inc.; 50 pages.

Voalté One User Manual v1.x; 2009; For use with Version 1.4; 46 pages.

User Manual Ascom 175 VoWiFi Handset; TD 92319GB; 2008-11-10/Ver. D; 67 pages.

"A Model for Presence and Instant Messaging," Network Working Group, Request for Comments: 2778, Category: Informational; Day et al.; Feb. 2000; © The Internet Society (2000); 17 pages.

(56) References Cited

OTHER PUBLICATIONS

Extended European Search Report for European Patent Application No. 18198845.2, dated Feb. 18, 2019; 8 pages.

* cited by examiner

CAREGIVER AND STAFF INFORMATION SYSTEM

The present application is a continuation of U.S. application Ser. No. 17/176,234, filed Feb. 16, 2021, now U.S. Pat. No. 11,257,588, which is a continuation of U.S. application Ser. No. 16/143,971, filed Sep. 27, 2018, now U.S. Pat. No. 10,957,445, which claims the benefit, under 35 U.S.C. § 119(e), of U.S. Provisional Application No. 62/568,671, filed Oct. 5, 2017, and U.S. Provisional Application No. 62/660,576, filed Apr. 20, 2018, each of which is hereby incorporated by reference herein in its entirety.

BACKGROUND

The present disclosure relates to healthcare information systems and particularly, to caregiver and staff information systems. More particularly, the present disclosure relates to a system that provides information to wireless handheld devices of caregivers and staff relating to alerts originating from patients in a healthcare facility and that permit secure communications between groups of caregivers, staff, and patients.

Caregivers, such as nurses and other clinicians, are typically assigned to multiple patients during their shifts. Various alerts or nurse calls generated by patients are communicated to the caregivers who must prioritize and manage their responses to the incoming alerts. Sometimes an alert is escalated to a secondary caregiver if the alert is not responded to within a threshold amount of time. Alerts and calls may be categorized as normal calls or high priority calls. Other staff members such as those in housekeeping, food service, and patient transporting, also respond to various alerts and calls originating from multiple patients. The terms "caregiver" and "staff" are used interchangeably herein.

Healthcare facilities sometimes provide to caregivers and staff during their shifts wireless communication devices, such as pagers or telephone handsets that have screens that show incoming patient calls and alerts. At the end of their shifts, the caregivers and staff may return these wireless communication devices back to the healthcare facility such as for recharging or for use by other caregivers and staff on subsequent shifts. Thus, these prior art wireless communication devices are dedicated devices used mostly for limited types of communications relating to patient healthcare.

In more recent times, it is common for caregivers and staff to bring their own smart phones to work. Caregivers and staff may call each other or text each other using their own smart phones while at work for purposes of coordinating patient care. Of course, the smart phones have their regular, unrestricted communications capability as well such that calls and texts can be transmitted by caregivers and staff via public infrastructure to their friends and family, for example. This raises various concerns regarding patient privacy and confidentiality. What is needed is an application that can be downloaded to the personal smart phones of caregivers and staff, that has functionality for managing calls and alerts within the healthcare facility, and that has secure communications capability between caregivers and staff in a healthcare facility.

SUMMARY

An apparatus, system, method, or computer-storage medium may comprise one or more of the features recited in the appended claims and/or the following features which, alone or in any combination, may comprise patentable subject matter:

A machine readable medium for managing patient calls and alerts at a healthcare facility may be provided. The machine readable medium may be non-transitory and may comprise a plurality of instructions that, in response to being executed, may result in a mobile device of a caregiver receiving at the mobile device multiple alerts that may relate to multiple patients that may be assigned to the caregiver; displaying on a display screen of the mobile device a first list of accepted alerts that the caregiver may have accepted and that may not have been escalated to another caregiver; and displaying on the display screen of the mobile device a second list of escalated alerts that may have been escalated to the caregiver from another caregiver.

In some embodiments, the accepted alerts and the escalated alerts may be displayed simultaneously on the display screen of the mobile device. Optionally, displaying the first list of accepted alerts may include displaying whether each accepted alert is either a high priority alert or a normal priority alert. Alternatively or additionally, displaying the first list of accepted alerts may include displaying for each accepted alert a name of a patient and a room location of the patient from which the alert may have originated. Further optionally, displaying the first list of accepted alerts may include displaying for each accepted alert an amount of time that may have elapsed since the respective accepted alert may have been originated.

In some embodiments, displaying the second list of escalated alerts may include displaying whether each escalated alert is either a high priority alert or a normal priority alert. Optionally, displaying the second list of escalated alerts may include displaying for each escalated alert a name of a patient and a room location of the patient from which the alert may have originated. Alternatively or additionally, displaying the second list of escalated alerts may include displaying for each escalated alert an amount of time that may have elapsed since the respective escalated alert may have been originated.

If desired, displaying each of the accepted alerts and the escalated alerts may include displaying a type of each of the accepted alerts and escalated alerts. For example, the types of accepted and escalated alerts may include one or more of the following: Fall, Bathroom, Room Service or Juice.

In some embodiments, the machine readable medium may be configured to result in displaying a name of the caregiver of the mobile device and a location of the caregiver. A first icon indicating the caregiver's availability status for accepting more alerts may be displayed. Optionally, a second icon that may be selectable by the caregiver to change the availability status may also be displayed. In response to selection of the second icon by the caregiver, a menu of availability status choices may be displayed. For example, the availability status choices may include two or more of the following: All, Available, Busy, or Unavailable. It is contemplated by this disclosure that the display screen of the mobile device may display an accept icon that may be selectable by the caregiver to accept another escalated alert from another caregiver.

In some embodiments, a menu bar including selectable icons that may include a Patients icon, a Staff icon, a first Messages icon, and a Me icon may be displayed. In response to selection of the Patients icon by the caregiver, a list of patients that may be assigned to the caregiver may be displayed. Displaying the list of patients that may be assigned to the caregiver may include displaying a name of each assigned patient and a room location of each assigned patient. In response to selection of the Staff icon by the caregiver, a default staff screen that may show a list of staff members that are assigned to a same unit as the caregiver may be displayed.

According to some embodiments of the present disclosure, a Unit icon may be displayed on the default staff screen. The Unit icon may be selectable by the caregiver to display a list of staff members that may be assigned to other units. Alternatively or additionally, a Filter icon may be displayed on the default staff screen. The Filter icon may be selectable by the caregiver to display a list of staff roles that may be selectable by the caregiver. If desired, a list of staff members that may have the one or more selected staff roles may also be displayed. Examples of the staff roles on the list may include one or more of the following: All, ANEST, Clergy, CMA, CN, CNA, HN, HUC, LPN, MD, MGR, NA, None, QB Tech, PCA, RN, Vol, Unit Sec, or CRNA.

In some embodiments, in response to selection of the Filter icon, an availability menu may be provided and may be usable by the caregiver to filter staff members for display based on an availability status of the staff members. A My Team icon that may be selectable by the caregiver to display a list of staff members that are on a same team as the caregiver may be displayed on the default staff screen.

In response to selection of the first Messages icon by the caregiver, a messages menu including a Device icon, a Video icon, a second Messages icon, and a Mobile icon may be displayed. In response to selection of the Video icon, the caregiver may be provided with the ability to establish a secure video communications link with another caregiver. For example, a Session Initiation Protocol (SIP) stack may be implemented in connection with the video communications link. In response to selection of the second Messages icon, the caregiver may be provided with the ability to send a secure text message to another caregiver. For example, a Session Initiation Protocol (SIP) stack may be implemented in connection with sending secure text messages. In response to selection of the Mobile icon, the caregiver may be provided with the ability to place a telephone call.

In some embodiments, the plurality of instructions, in response to being executed, may result in the mobile device of the caregiver determining at the mobile device received signal strength indicators (RSSI's) for communications from a plurality of other mobile devices of other caregivers and may display a rank ordered list of the other caregivers on the mobile device of the caregiver based on the RSSI's. For example, the rank ordered list may be displayed so as to list the other caregivers from closest to farthest in distance from the mobile device based on the received signal strengths.

Optionally, the plurality of instructions, in response to being executed, may result in the mobile device of the caregiver displaying on the display screen of the mobile device a first selectable icon that, in response to being selected, may result in the caregiver's availability status being set to an automatic mode in which the caregiver's availability may be changed automatically as the caregiver moves throughout the healthcare facility. Alternatively or additionally, the plurality of instructions, in response to being executed, may result in the mobile device of the caregiver displaying on the display screen of the mobile device a second selectable icon that, in response to being selected, may result in the caregiver's availability being set to a do not disturb mode in which the caregiver is unavailable. The mobile device may be configured to not receive alerts when the caregiver's availability is set to the do not disturb mode.

In some embodiments, a Busy screen may be displayed on the mobile device and the caregiver's availability may be set to busy in response to the caregiver entering a patient room. If desired, the Busy screen may include a selectable icon that, in response to being selected, may result in the caregiver's availability being set to a do not disturb mode in which the caregiver may be unavailable. In some embodiments, an Available screen may be displayed on the mobile device and the caregiver's availability may be set to available in response to the caregiver being located in a common area of the healthcare facility outside of patient rooms. Optionally, the Available screen may include a selectable icon that, in response to being selected, may result in the caregiver's availability being set to a do not disturb mode in which the caregiver is unavailable.

It is contemplated by this disclosure that the plurality of instructions, in response to being executed, may result in the mobile device of the caregiver displaying on the display screen of the mobile device a first selectable icon that, in response to being selected, may result in the caregiver's availability being set to a do not disturb mode in which the caregiver is unavailable. The mobile device may be configured to not receive alerts when the caregiver's availability is set to the do not disturb mode. The do not disturb mode may last for a threshold period of time and then automatically may expire after the threshold period of time unless action is taken to terminate the do not disturb mode early or extend the do not disturb mode for additional time.

If desired, the plurality of instructions, in response to being executed, may result in the mobile device of the caregiver displaying a graphical end icon that, in response to being selected, may terminate the do not disturb mode and may set the caregiver's availability to available. Alternatively or additionally, the plurality of instructions, in response to being executed, may result in the mobile device of the caregiver displaying a graphical add time icon that, in response to being selected, may add a predetermined amount of time to the threshold period of time to establish a new threshold period of time. For example, the predetermined amount of time may be five minutes.

According to another aspect of the present disclosure, a system may include a plurality of mobile devices that may be carried by caregivers, at least one server for sending alert messages to the plurality of mobile devices; and at least one patient device in a patient room. The at least one patient device may be configured to generate a first alert message of the alert messages in response to an interaction with a patient in the patient room. The system may also have a processor located at the patient room. The processor may receive the first alert message and may determine a message priority designation from a first priority designation or a second priority designation. The processor may forward the alert message along with the message priority designation for receipt by the server which then may forward the alert message and the priority designation to at least one mobile device of a caregiver assigned to the patient. The plurality of mobile devices may be configured to permit the caregivers to accept responsibility for responding to respective alert messages or to re-route respective alert messages to one or more other caregivers.

In some embodiments, the system further may include an audio station that may be located in the patient room and that may be coupled to the processor. Each mobile device of the plurality of mobile devices may be configured to display an icon for each respective alert message that may be selectable by the respective caregiver to open up a communications channel with the audio station so that the caregiver can speak with the patient.

According to a further aspect of the present disclosure, a system may include a plurality of mobile devices that may be carried by caregivers, at least one server for sending alert messages to the plurality of mobile devices, and a plurality of patient devices in a patient room. The plurality of patient devices may be configured to generate the alert messages in response to interactions with a patient in the patient room. The plurality of patient devices may include a patient bed, a pillow speaker unit, and a patient tablet, for example.

In some embodiments, the system may further include a processor located at the patient room. The processor may receive the alert messages and may determine for each alert message a message priority designation from a first priority designation or a second priority designation. The processor may forward each alert message along with its respective message priority designation for receipt by the server which then may forward the respective alert message and the respective priority designation to at least one mobile device of a caregiver assigned to the patient. If desired, the plurality of mobile devices may be configured to permit the caregivers to accept responsibility for responding to respective alert messages or to re-route respective alert messages to other caregivers.

In some embodiments, the system may further include a desktop computer that may have a display on which a Past Conversation screen may be displayed. The Past Conversation screen may be usable to view a past text message conversation between other caregivers about a selected patient. Optionally, the Past Conversation screen also may display a current availability status of each of the caregivers involved in the past text message conversation.

In some embodiments, the system may further include a desktop computer that may have a display on which a Create Conversation screen is displayed. The Create Conversation screen may be usable to start a text message conversation between a user of the desktop computer and one or more other caregivers about a selected patient. The Create Conversation screen may permit selection of the patient about which the text message conversation pertains by using a first drop down menu that may list all patients admitted in a unit or by using a second drop down menu that may appear on the Create Conversation screen in response typing a portion of a patient name. Alternatively or additionally, the Create Conversation screen may permit selection of the one or more other caregivers to participate in the text message conversation by using a first drop down menu that may list all caregivers on duty in a unit or by using a second drop down menu that may appear on the Create Conversation screen in response typing a portion of a caregiver name. If desired, the Create Conversation screen may include an icon that may be selectable to designate all caregivers on duty in the unit as participants in the text message conversation. Optionally, the Create Conversation screen may display an availability status of each of the caregivers involved in the text message conversation.

According to yet another aspect of the present disclosure, a system may include a plurality of mobile devices that may be carried by caregivers, a messaging server for sending alert messages to the plurality of mobile devices, and a first nurse call server in communication with a first plurality of patient devices in a first patient room. The first plurality of patient devices may be configured to generate first alert messages in response to interactions with a first patient in the first patient room. The first alert messages may be communicated in a first format according to a first protocol to the messaging server which, in turn, may provide first notifications to one or more mobile devices of the plurality of mobile devices. The system also may include a second nurse call server in communication with a second plurality of patient devices in a second patient room. The second plurality of patient devices may be configured to generate second alert messages in response to interactions with a second patient in the second patient room. The system further may include a configuration server in communication with the second nurse call server. The second alert messages may be communicated in a second format according to a second protocol, different than the first format and first protocol, respectively, to the messaging server which, in turn, may convert the second alert messages into third alert messages having the first format according to the first protocol. The third alert messages may be communicated to the messaging server which, in turn, may provide second notifications to one or more mobile devices of the plurality of mobile devices.

In some embodiments, the system may further include a Session Initiation Protocol (SIP) server and a private branch exchange (PBX) voice bridge. Voice communications from the plurality of mobile phones may be communicated to the first nurse call server via the SIP server without involving the PBX voice bridge, and voice communications from the plurality of mobile phones may be communicated to the second nurse call server via the SIP server and the PBX voice bridge. Alternatively or additionally, the system may further include a publish/subscribe server that may manage which mobile phones of the plurality of mobile phones are to receive each alert message of the first and third alert messages. The first alert messages from the first nurse call server and the third alert messages from the configuration server may be provided to the publish/subscribe server as inputs and the publish/subscribe server may send outputs to the messaging server.

It is contemplated by this disclosure that the first plurality of patient devices may include a first patient bed, a first pillow speaker unit, and a first patient tablet. Alternatively or additionally, the second plurality of patient devices may include a second patient bed, a second pillow speaker unit, and a second patient tablet. At least one mobile device of the plurality of mobile devices may stores and may execute a machine readable medium having any one or more of the features or functions discussed above and discussed elsewhere herein.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
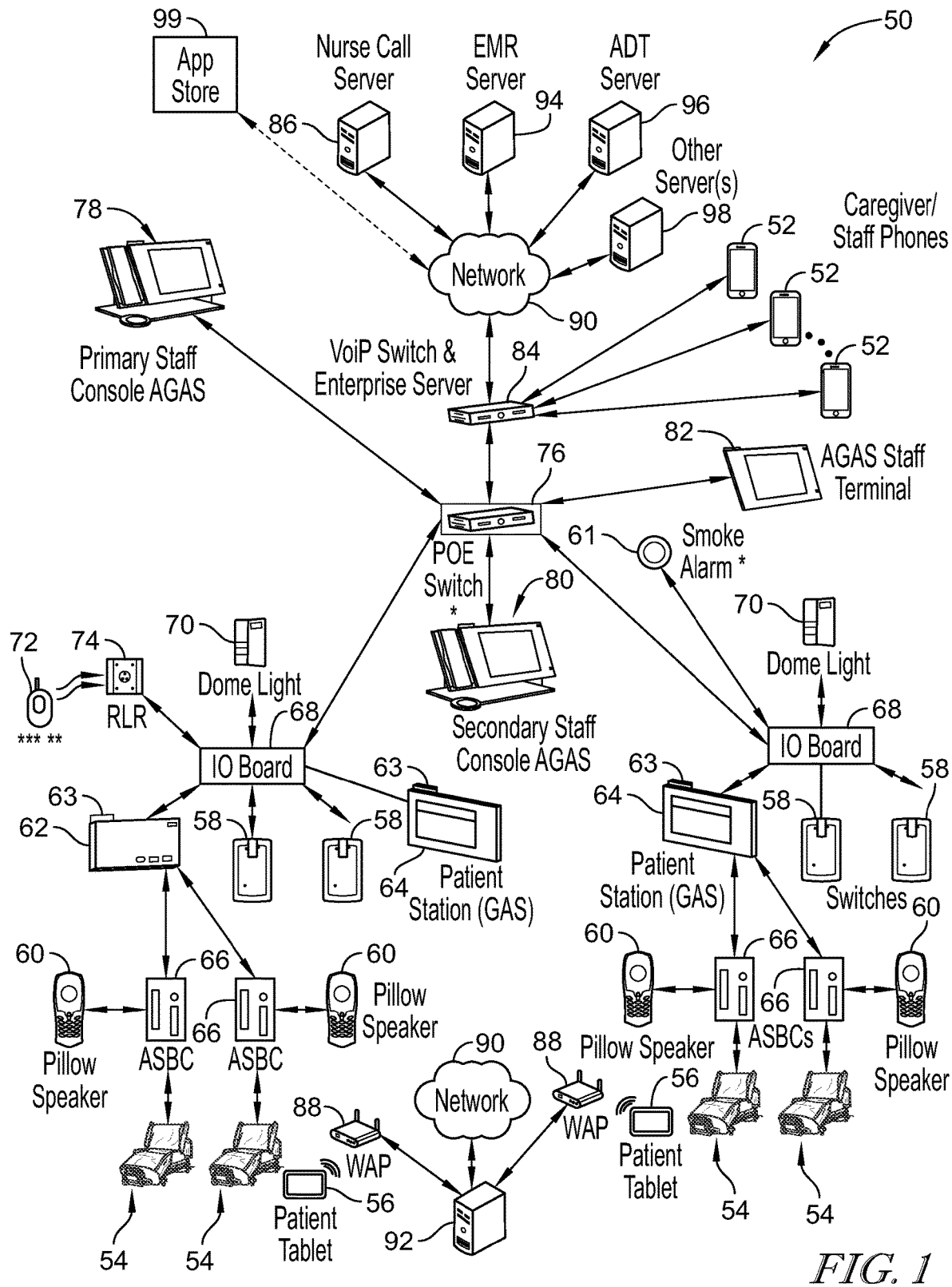
FIG. 1 is block diagram of a caregiver and staff information system showing a number of caregiver and staff phones that operate a caregiver and staff communication software application for use in monitoring patient calls and alerts originating from assigned patients and various hospital equipment including patient beds, patient tablets, call switches, and pillow speaker units.

A caregiver and staff information system 50 has a number of mobile devices 52, illustratively caregiver and staff phones, that each operate a caregiver and staff communication software application for use in monitoring patient calls and alerts originating from assigned patients and various hospital equipment located in a room of the patient, including patient beds 54, patient tablets 56, call switches 58, and handheld pillow speaker units 60 as shown in FIG. 1. In the illustrative example, alerts may also originate from a smoke alarm 61, for example. The features and functions of the caregiver and staff communication software application of mobile devices 52 are discussed in detail below in connection with FIGS. 2-46. The caregiver and staff communication software application is sometimes referred to herein as the mobile caregiver application.

In contemplated embodiments, the mobile caregiver application is configured to allow caregivers in an acute care setting to use their mobile phones 52 for monitoring alerts and calls from patients; for conducting voice, video, and text messaging between caregivers; and for permitting voice communications to audio stations (e.g., standard audio stations 62 and/or graphical audio stations 64) mounted in patient rooms adjacent to respective patient beds 54. The mobile caregiver application is also configured to act as a secondary notification system that supplements the nurse call system portion of system 50.

In the illustrative example, beds 54 and pillow speaker units 60 are coupled with appropriate cables, well known in the art, to respective audio station bed connectors (ASBC's) 66 as shown diagrammatically in FIG. 1. In other embodiments, one or more network interface units (NIU's) or wireless interface units (WIU's) provide the connectivity between beds 54 and respective audio stations 62, 64 in lieu of ASBC's 66. Further details of ASBC's and NIU's are shown and described in U.S. Pat. Nos. 7,538,659 and 7,319,386 and in U.S. Patent Application Publication Nos. 2009/0217080 A1, 2009/0212925 A1 and 2009/0212926 A1, each of which is hereby expressly incorporated by reference herein. Further details of WIU's are shown and described in U.S. Patent Application Publication No. 2007/0210917 A1 which is hereby expressly incorporated by reference herein.

Each of audio stations 62, 64 includes a code blue call lever 63 which is pulled by a caregiver in an emergency such as when a patient in the room is having a heart attack. Call switches 58, smoke alarm 61, and audio stations 62, 64 are each communicatively coupled to a respective input/output (I/O) circuit board 68 as shown diagrammatically in FIG. 1. Circuit boards 68 are sometimes referred to herein as I/O board or I/O circuitry. Each I/O board 68 includes a processor, such as a microprocessor, microcontroller, etc., that receives various alerts and calls, sometimes referred to herein as "alert messages," from beds 54, pillow speaker units 60, smoke alarms 61, and audio stations 62, 64 in response to the code blue lever 63 being pulled. The processor of I/O circuitry 68 determines an alert message priority designation for each of the incoming alert messages. For example, in the illustrative embodiment, alert messages are designated as either Normal alert messages or High Priority alert messages. However, in other embodiments, more than two alert message priority designations may be used.

The I/O board 68 and therefore, the processor of I/O board 68, is located at the respective patient room. Thus, the alert message priority designation is made at each patient room for the alert messages being communicated to the I/O board 68. As such, a central server is not needed for determining message priority for the messages received by I/O board 68. The I/O board 68 forwards each alert message and its respective priority designation to the remainder of system 50.

Each I/O board 68 is coupled to a respective dome light 70 which really includes multiple lights that are illuminated to indicate room status. The illumination of the various lights of dome light 70 is controlled by the I/O board 68 based on alert conditions occurring in the respective patient room and based on caregiver presence in, or absence from, the respective patient room. Dome lights 70 are mounted outside each of the patient rooms, typically near a doorway to the respective room. In some embodiments, I/O boards 68 are situated in a housing to which the dome lights 70 are mounted. Thus, the I/O boards 68 are located outside the patient rooms adjacent the dome lights 70 in such embodiments. In other embodiments, I/O boards 68 are located inside the patient rooms. In either case, the I/O boards are considered to be "at" the patient room according to this disclosure.

In the illustrative example, a locating badge 72 is shown in wireless communication with a remote locator receiver (RLR) 74 which, in turn, is communicatively coupled with the respective patient room in which the RLR 74 is located. It should be appreciated that system 50 includes a multitude of badges 72 that are worn by respective caregivers and a multitude of RLR's 74 located throughout the respective healthcare facility, including being located in the various patient rooms. In response to an RLR 74 detecting one or more badges 72 in any particular room, a signal or message is communicated to the respective I/O board 68 and the lighting of the associated dome light 70 is updated accordingly. In the illustrative example, badges 72 transmit infrared (IR) signals to RLR's 74 but alternative embodiments in which radio frequency (RF) transmissions, including ultra-wideband (UWB) transmissions, are made by badges 72 and/or RLR's 74 are within the scope of this disclosure.

Still referring to the diagrammatic example of FIG. 1, each I/O board 68 is communicatively coupled to a Power over Ethernet (PoE) switch 76 which is, in turn, communicatively coupled to a primary staff console 78 (sometimes referred to as a "master nurse station"), a secondary staff console 80, and a staff terminal 82. PoE switch 76 is communicatively coupled to a voice over Internet protocol (VoW) Switch and Enterprise server 84 which is, in turn, coupled to a nurse call server 86 via Ethernet infrastructure, illustrated diagrammatically as network 90 in FIG. 1. It should be appreciated that devices 58, 60, 62, 64, 66, 68, 70, 76, 78, 70, 82, 84, 86 are illustrative of a diagrammatic nurse call system portion of the overall system 50 and that nurse call system architecture will vary from one healthcare facility to the next. Other examples of nurse call system architecture and the various types of equipment included in various embodiments of a nurse call system (as well as network 50, in general) can be found in U.S. Pat. Nos. 7,746,218; 7,538,659; 7,319,386; 7,242,308; 6,897,780; 6,362,725; 6,147,592; 5,838,223; 5,699,038 and 5,561,412 and in U.S. Patent Application Publication Nos. 2009/0217080; 2009/0214009; 2009/0212956; and 2009/0212925, each of which is hereby incorporated by reference herein in its entirety for all that it teaches to the extent not inconsistent with the present disclosure which shall control as to any inconsistencies.

In the illustrative example, patient tablets 56 are also included as part of the nurse call system portion of overall system 50. Tablets 56 are used by patients to send specific patient requests such as requests for pain medication, requests for bathroom assistance, food requests, drink requests, ice chips requests, requests for assistance with personal care, etc. For additional details of the functionality of tablets 56 see FIGS. 2-5 and the related discussion found in U.S. Patent Application Publication No. 2016/0055299 which is hereby incorporated by reference herein in its entirety for all that it teaches to the extent not inconsistent with the present disclosure which shall control as to any inconsistencies. In the illustrative example, tablets 56 communicate wirelessly with wireless access points (WAP's) 84 which, in turn, communicate with a patient tablet communications server 92. Server 92 communicates the patient requests, which are also considered to be alert messages according to this disclosure, to nurse call server 86 via network infrastructure 90.

In connection with alert messages originating from beds 54, these include alert messages relating to one or more of the following: bed exit of the patient from the respective bed 54, patient position on the respective bed 54 exceeding a threshold, patient movement on the respective bed 54 exceeding a threshold or falling below a threshold, siderail position (e.g., siderail down) of the respective bed 54, casters of the respective bed 54 not being braked, angle of a head section of the respective bed 54 being below a threshold angle (e.g., 30 degrees), an upper frame of the respective bed 54 not being in its lowest position relative to a base frame of the respective bed 54, a bed component exceeding a threshold temperature, a mattress bladder of the respective bed 54 falling below a threshold pressure, a pneumatic system error or failure of the respective bed 54, an actuator error or failure of the respective bed 54, an overcurrent condition of a component of the respective bed 54, a power system error or failure of the respective bed 54, and power is disconnected from the respective bed 54.

Still referring to FIG. 1, system 50 includes an electronic medical records (EMR) server 94 and an admission/discharge/transfer (ADT) server 96. System 50 includes various other servers 98 as well. Other servers 98 includes, for example, a real time locating system (RTLS) server that is communicatively coupled to receivers 74. In such embodiments, receivers 74 are not communicatively coupled to I/O boards 68. The badges 72, receivers 74, and RTLS server form a real time locating system portion of overall system 50. Staff locating information is communicated from the RTLS server 98 to nurse call server 86 via network 90 in such embodiments.

In some embodiments, another of the other servers 98 is a server that manages the routing of alert messages and related staff information to the various mobile devices 52. In general, alert messages relating to particular patients or particular rooms assigned to particular caregivers are sent to the mobile device 52 of that particular caregiver. The alert messages may originate from beds 54, pillow speaker units 60, and patient tablets 56 in the illustrative example. However, it is contemplated by this disclosure that alert messages originating from other types of equipment may be communicated to the mobile devices 52 of assigned caregivers as well.

In some embodiments, the mobile caregiver application is available to each caregiver from an Application ("App") Store 99 which is accessible via the Internet as indicated by the dashed double headed arrow in FIG. 1. In other embodiments, the mobile caregiver application is provided to caregivers internally by a systems administrator of system 50. Thus, in some embodiments the mobile caregiver application is stored in one or more of servers 86, 92, 94, 96, 98 and is uploaded to the mobile devices 52 of caregivers or downloaded by the caregivers to their respective mobile devices 52.

The features and functions of the mobile caregiver application are described below in connection with FIGS. 2-46 which comprise screen shots that appear on the user interface screens or display screens of mobile devices 52. By seeing the functionality represented in each of the screen shots and by considering the following description of the screen shots of FIGS. 2-46, those skilled in the art will be enabled to make and use the mobile caregiver application, and its variant embodiments, contemplated herein. It should be appreciated that the screen shots of this disclosure are exemplary in nature and are provided to give a general sense of the type of information that may appear on the display screen of any given mobile device 52 during use of the contemplated mobile caregiver application. Thus, the screen shots are merely individual examples from a practically unlimited number of possibilities. That is, the information such as alert messages, staff names, staff locations, room name formats, unit names, etc. is dynamic and varies from healthcare facility to healthcare facility and, in fact, varies in any given healthcare facility throughout any given day in response to the various incoming alert messages, for example.

Figure 2:
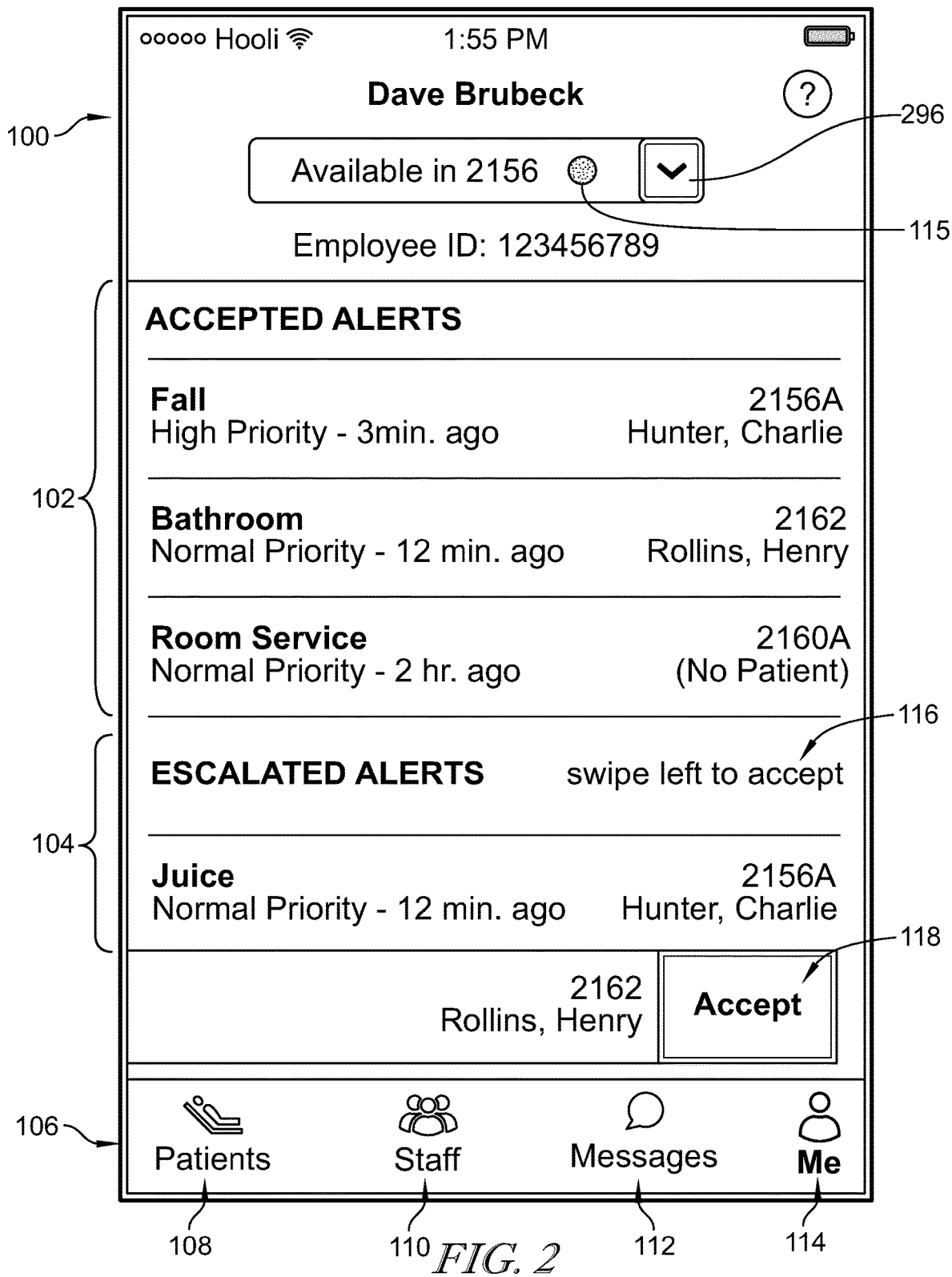
FIG. 2 is a screen shot of a Staff Detail screen showing a list of accepted alerts and escalated alerts of an individual caregiver, the Staff Detail screen being shown in response to a Me icon being selected on a main menu at a bottom of the screen.

Referring now to FIG. 2, a Staff Detail screen 100 includes a list of accepted alerts 102 and escalated alerts 104 of an individual caregiver. A main menu 106 is provided at the bottom of screen 100 and includes a Patients icon 108, a Staff icon 110, a Messages icon 112, and a Me icon 114. The Staff Detail screen 100 is shown on the respective mobile device 52 in response to the Me icon 114 being selected on the main menu 106. Icons are sometimes referred to as buttons herein. Thus, these terms are used interchangeably. Icons or buttons are considered to be selected or selectable, herein, in that a user touches or taps the icon on the display screen of the respective mobile device 52 to navigate to additional functionality of the mobile caregiver application associated with the respective icon or button.

In the upper section of screen 100 of FIG. 2, the caregiver's name, location and employee identification (ID) number is shown. In the illustrative example, the employee's name is Dave Brubeck who is located in room 2156 and is available for answering voice calls, phone messages, and alerts. A circle 115 is provided to the right of the text "Available in 2156" which appears in a text box. The circle 115 is color coded green if the caregiver is available and is color coded red if the caregiver is not available. The accepted alerts 102 of illustrative screen 100 includes a Fall alert, a Bathroom alert, and a Room Service alert. The Fall alert is designated as a High Priority alert and was generated three minutes ago in room 2156A by a patient named Charlie Hunter. The Bathroom alert is designated as a Normal Priority alert and was generated twelve minutes ago in room 2162 by a patient named Henry Rollins. The Room Service alert is designated as a Normal Priority alert and was generated two hours ago in room 2160A. No patient is assigned to room 2160A in the given example.

The Fall alert of the accepted alerts 102 is based on bed status information from the bed 54 in room 2156A assigned to Charlie Hunter. For example, a Falls Protocol, when enabled, may require that a patient remain in the bed 54 as monitored by a bed exit/patient position monitoring system of the bed 54, that certain siderails of the bed 54 be in their raised positions, that the casters of bed 54 be braked, and that the upper frame of the bed 54 be in its lowest position relative to the base frame of the bed 54. If any of those Falls Protocol conditions are violated as detected by nurse call server 86, then a Fall alert is considered to exist and an appropriate message is sent via the appropriate portions of system 50 (network 90 and server 84 in the illustrative example) to the mobile device 52 of the caregiver assigned to the patient of the particular bed 54. In the illustrative embodiment, the Fall alert does not specify which particular bed condition of the Falls Protocol is violated. In other embodiments, the particular bed condition may be specified on screen 100 such as indicating siderail down, patient exiting the bed, or brake not set, for example, in lieu of or in addition to the text Fall.

The Bathroom alert of the accepted alerts 102 is based on an input from the patient in room 2162 using the respective patient tablet 56. The Room Service alert of the accepted alerts 102 is generated by another staff member in some embodiments. For example, a staff member may use their mobile device 52 to generate the Room Service alert or may use the room station 64 in the room to be serviced which is rom 2160A in the given example. In other embodiments, the ADT system of which server 96 is a part may generate the Room Service alert in response to the patient previously assigned to the room being discharged from the healthcare facility. Thus, this disclosure contemplates that alert messages may also be generated by other staff members and other portions of system 50.

The Juice alert of the escalated alerts 104 is based on an input from the patient in room 2156A using the respective patient tablet 56. However, the primary caregiver, who is a caregiver other than Dave Brubeck in the given example, was not able to respond to this particular alert message and so the alert was escalated from that other caregiver to Dave Brubeck for possible response. Dave Brubeck is sometimes referred to as a secondary caregiver in this scenario. The secondary caregiver is the caregiver designated for escalation of any alerts to which a primary caregiver is unable to respond. It is contemplated by this disclosure that escalation of alerts may occur in various ways such as after a preset period of time has elapsed without acceptance by the primary caregiver and/or if the primary caregiver has a status of unavailable and/or if the primary caregiver uses their mobile device 52 to manually escalate an alert to a secondary caregiver. A "swipe left to accept" icon 116 is provided on screen 100 and is used by the caregiver to accept any incoming escalated alerts by swiping left on the icon 116 or by swiping left on the escalated alert information. In the illustrative example, another alert is originating from room 2162 of patient Henry Rollins and can be accepted by the caregiver by selecting the Accept button 118.

Figure 3:
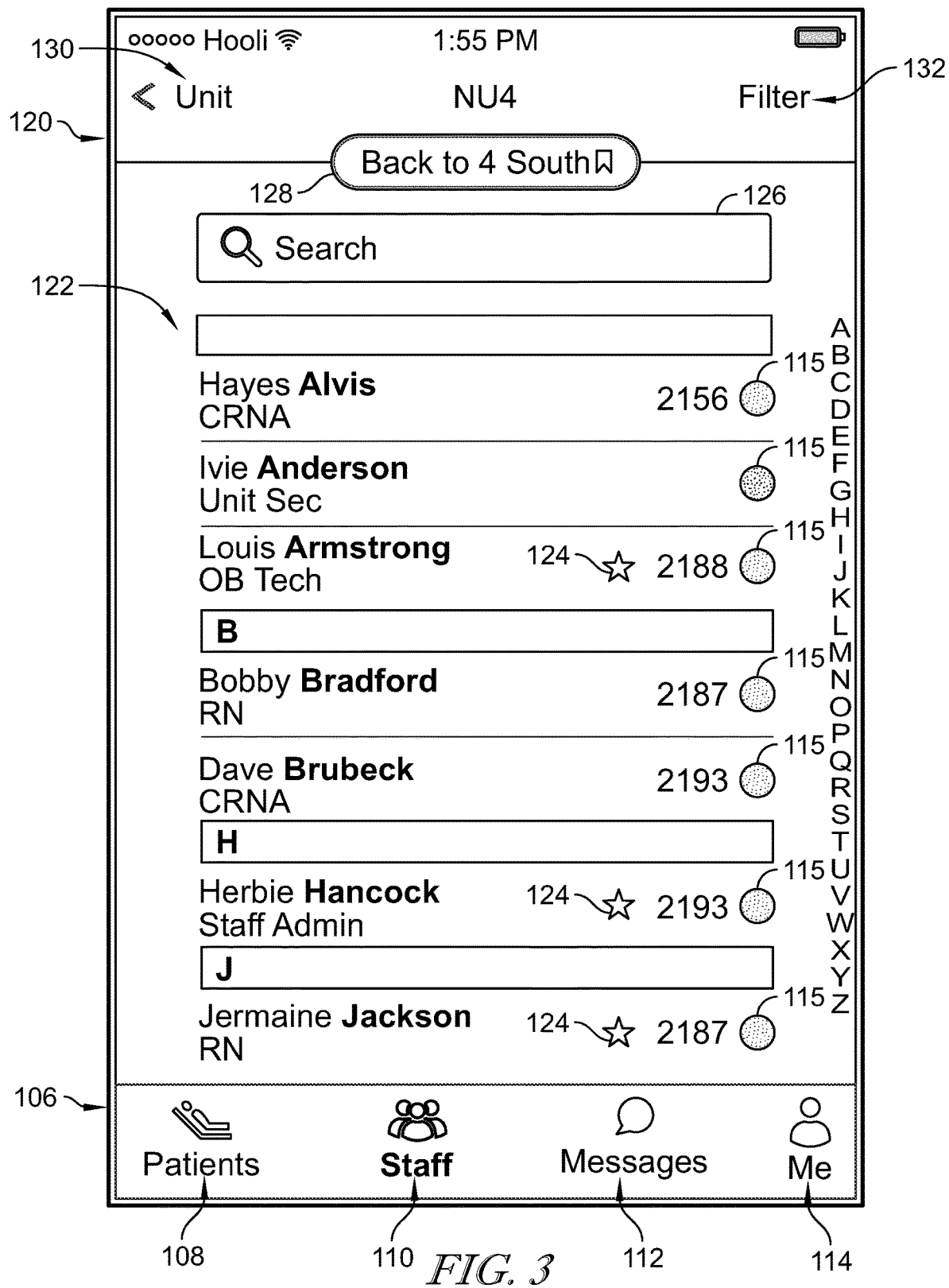
FIG. 3 is a screen shot of a Staff Detail screen showing a list of staff assigned to nursing unit four (NU4) with green and red circles indicating the availability status for each listed caregiver, the Staff Detail screen being shown in response to a Staff icon being selected on the main menu at the bottom of the screen.

Referring now to FIG. 3, a Staff Detail screen 120 has a list 122 of staff assigned to nursing unit four (NU4) in the given example because NU4 is the unit to which caregiver Dave Brubeck is assigned. Screen 120 is shown on the respective mobile device 52 in response to the Staff icon 110 being selected on the main menu 106. List 122 has staff members of the caregiver's unit arranged in alphabetical order from top to bottom. Letters of the alphabet are provided to the right of list 112 with each letter serving as a selectable button to navigate to other portions of the list 122 which are not able to be seen on screen 120 in FIG. 3.

Beneath each staff member's name on list 122 is the staff member's role or title (e.g., CRNA, Unit Secretary, OB Tech, RN, just to give a few). If the caregivers appearing on list 122 are wearing badges 72 and are detected by receivers 74 in a particular room or other location, such location information is shown to the right of the staff member's name on list 122. Also to the right of each caregiver's name on list 122 is a corresponding circle 115 that is color coded green or red, as discussed above, depending upon whether the particular staff member is available or unavailable, respectively. The darker circle 115 next to Ivie Anderson's name indicates a red circle and the other circles 115 in FIG. 3 are color coded green. Finally, star indicia 124 is provided to the right of any staff members on list 122 who have been designated as "favorites" by the caregiver of the associated mobile device 52.

Screen 120 includes a search field or box 126 in which a staff member's name can be typed to search for that particular caregiver. By tapping in box 126, a keyboard appears on screen 120 and is used to type the desired name, or portion thereof, to be searched. Above search box 126 is a "Back to 4 South" button 128 that is selectable to navigate back to a list of staff members assigned to 4 South. For example, NU4 may be a subset of all of the units assigned to 4 South such other nursing units of 4 South may include NU1, NU2, NU3, NU5, etc. Screen 120 further includes a Unit icon 130 and a Filter icon 132. Selection of Unit icon 130 by the caregiver on screen 120 results in a menu being shown of all units of the associated healthcare facility that the caregiver can select to obtain a list, similar to list 122, of staff members assigned to the selected Unit. Selection of Filter icon 132 by the caregiver on screen 120 results in a menu being shown having an Availability filter and a Staff Title filter being shown as will be described below in connection with FIGS. 4 and 5.

Figure 4:
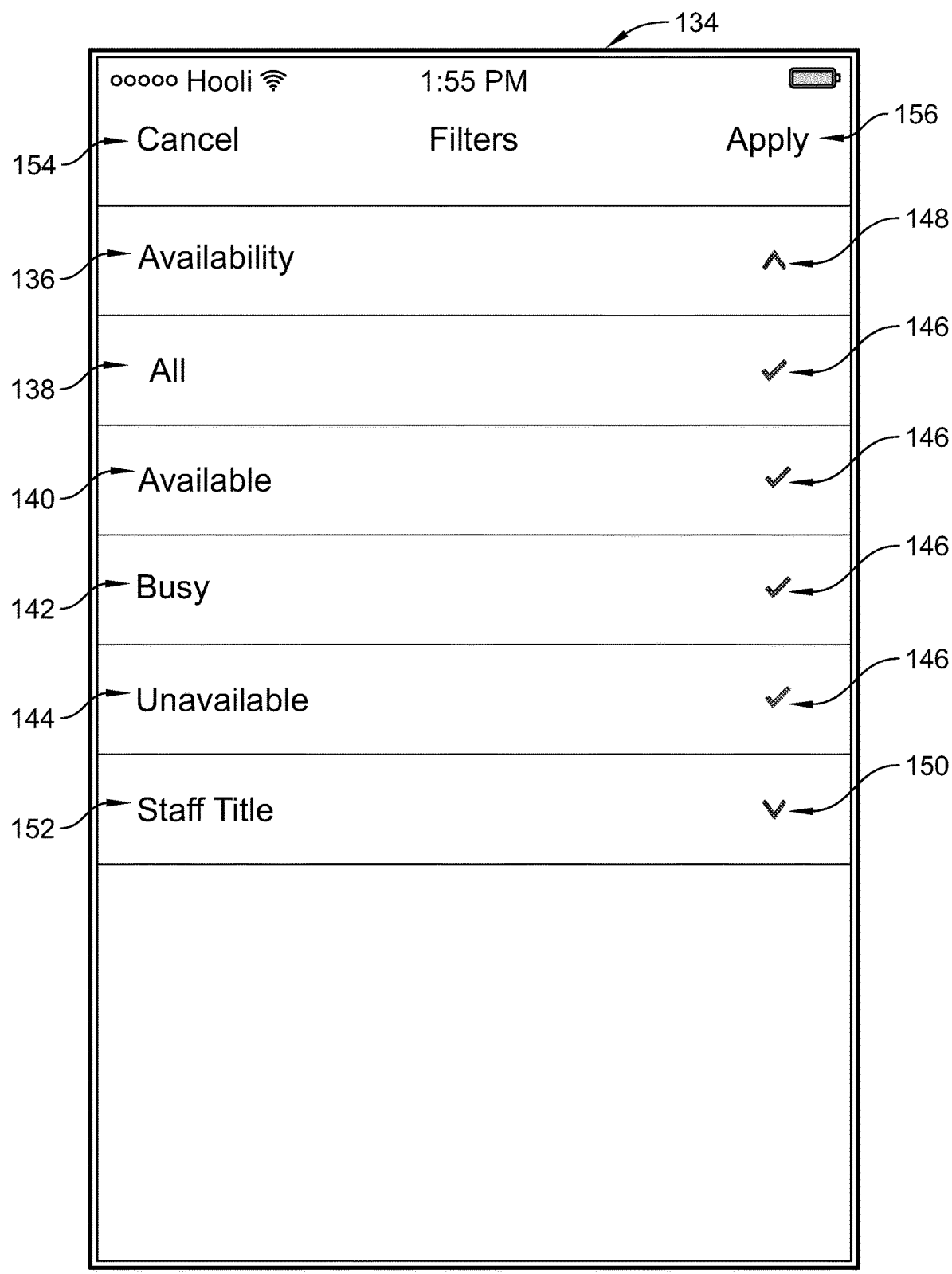
FIG. 4 is a screen shot of a first Filter screen having an Availability filter expanded to show availability filter options that can be selected by the caregiver.

Referring now to FIG. 4, a first Filter screen 134 has an Availability filter expanded in response to selection of an Availability menu option icon 136 to show a menu of availability filter options icons that can be selected by the caregiver. The Availability filter options include an All icon 138, Available icon 140, a Busy icon 142, and an Unavailable icon 144. In the illustrative example of FIG. 4, the All icon 138 has been selected resulting in check marks 146 being shown in each button 138, 140, 142, 144. In some embodiments, a caregiver or staff member availability status of busy results in the respective circle 115 for that caregiver being color coded yellow. Assuming All icon 138 is not selected, then individual icons 140, 142, 144 can be selected or not selected at the option of the caregiver. Subsequent touches or taps of icons 138, 140, 142, 144 toggle the associated filter between active (e.g., on) and inactive (e.g., off) states.

If the All icon is selected on screen 134, then list 122 of screen 120 of FIG. 3 will show all staff members of a selected unit regardless of their availability status. If only Available icon 140 is selected on screen 134, then only available staff members will appear in list 122 of screen 120. If only Busy icon 142 is selected on screen 134, then only busy staff members will appear in list 122 of screen 120. If Unavailable icon 144 is selected on screen 134, then only unavailable staff members will appear in list 122 of screen 120. If combinations of two icons 140, 142, 144 are selected on screen 134, then the staff members having the availability status corresponding to the two selected icons 140, 142, 144 will appear in list 122 of screen 120.

An up arrow indicia 148 is provided in the Availability menu option icon 136 to indicate that a subsequent tap of icon 136 will collapse the menu of availability filter options. Thus, selection of icon 136 when indicia 148 is present results in icons 138, 140, 142, 144 disappearing from screen 134 and then up arrow indicia 148 is replaced in icon 136 with a down arrow indicia similar to a down arrow indicia 150 shown in a Staff Title menu option icon 152. Down arrow indicia 150 indicates that icon 152 is selectable to expand the associated menu options of icon 152 (or icon 136 when down arrow 150 appears in icon 136). A Cancel button 154 is provided at the top left side of screen 134 and is selected if the caregiver does not wish to implement the filter selections that have been made on screen 134. An Apply button 156 is provided at the top right side of screen 134 and is selected if the caregiver wishes to proceed with applying or implementing the filter selections that have been made on screen 134.

Figure 5:
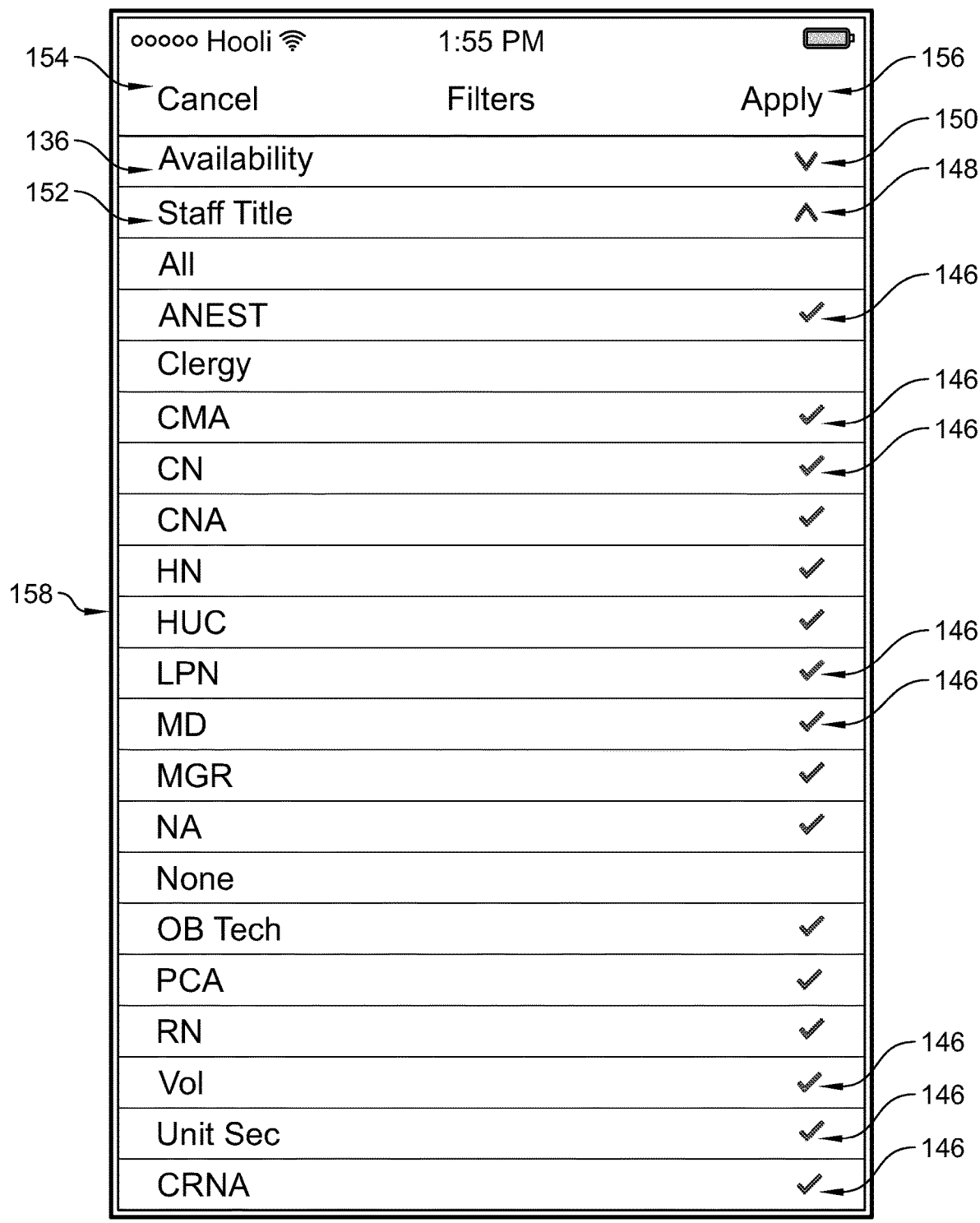
FIG. 5 is a screen shot of a second Filter screen having a Staff Title filter expanded to show staff title filter options that can be selected by the caregiver.

Referring now to FIG. 5, a second Filter screen 158 has a Staff Title filter expanded in response to selection of the Staff Title menu option icon 152 to show a menu of staff title filter option icons that can selected by the caregiver. Basically, each staff title filter option icon relates to a particular staff title and due to the large number of such icons in FIG. 5, these icons have not been identified with reference numerals but instead, the staff filtered by selection of each icon of screen 158 is indicated by its associated staff name. In the illustrative example, the staff filter icons are named, from top to bottom, All, ANEST, Clergy, CMA, CN, CAN, HN, HUC, LPN, MD, MGR, NA, None, OB Tech, PCA, RN, Vol, Unit Sec and CRNA. These acronyms are generally known in the healthcare field. Other healthcare facilities may have staff titles that are different than those shown in connection with screen 158 of FIG. 5. Also, the menu of staff title menu option icons shown in FIG. 5 is larger than can be seen on the user interface screen of the associated mobile device. Thus, the caregiver will scroll up or down on the mobile device display to see these various menu options. Selection and deselection of the menu option icons, with check marks 146 appearing for selected options, is done in the same manner as described above in connection with FIG. 4. The same goes for the functionality of buttons 154, 156. Thus, the descriptions do not need to be repeated.

Figure 6:
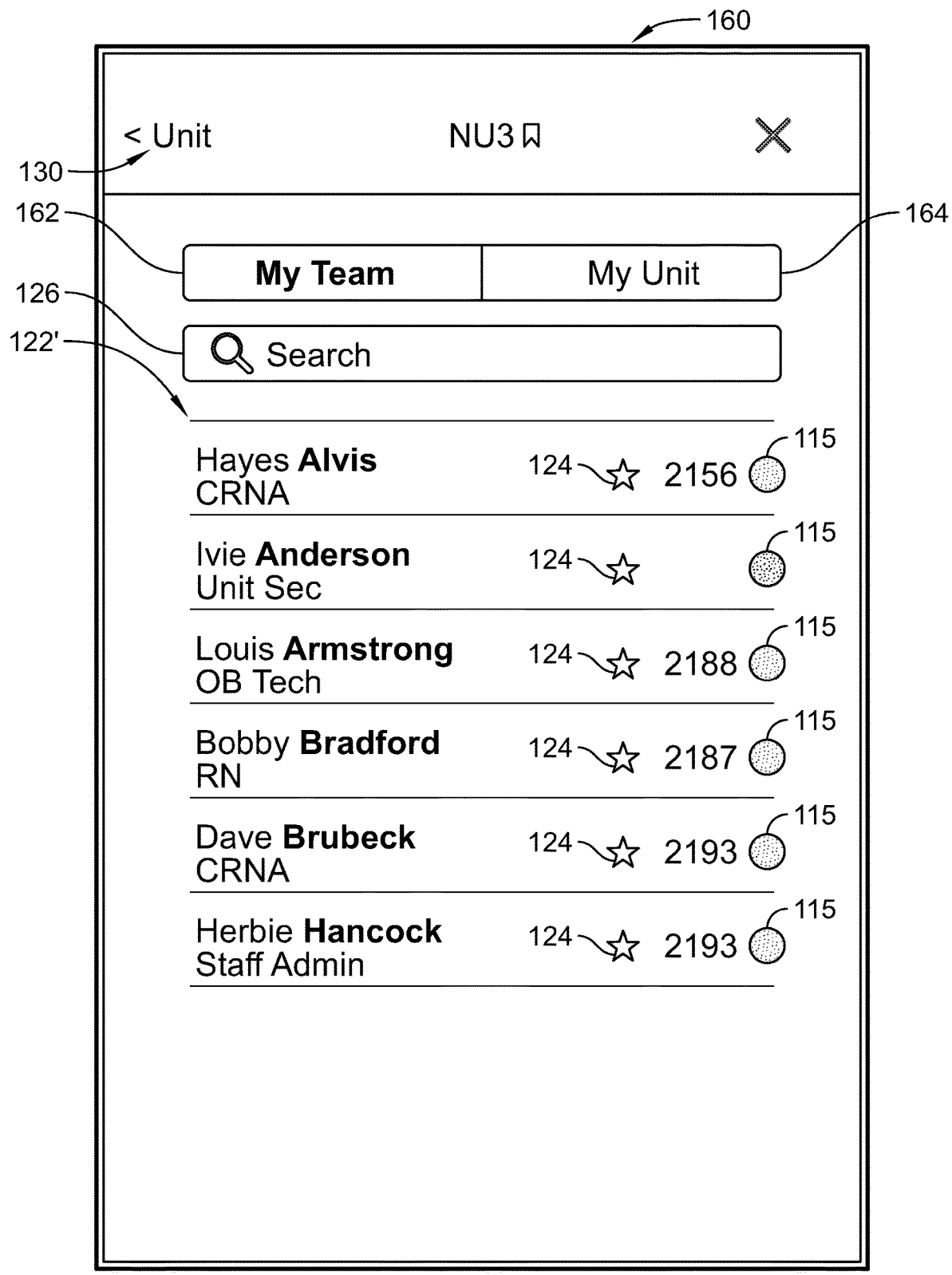
FIG. 6 is a screen shot of a My Team screen showing a list of staff assigned to the same team as the caregiver.

Referring now to FIG. 6, a My Team screen 160 is shown and is an alternative screen that appears on a display screen of a mobile device 52 in response to Staff icon 110 of main menu 106 being selected. Screen 160 is similar to screen 120 of FIG. 4 and so only pertinent differences will be noted, otherwise like reference numbers are used to denote like features and the descriptions will not be repeated. Screen 160 includes a My Team icon 162 and an adjacent My Unit icon 164. Icons 162, 164 are located above search field 126 in the illustrative example. The My Team icon 162 is highlighted to indicate that a list 122' of staff members on screen 160 is the caregiver's team. In the illustrative embodiment, each staff member on the caregiver's team is automatically designated by the caregiver mobile application as being one of the caregiver's "favorites" as indicated by the respective star 124 appearing to the right of each team member's name. Selection of My Unit icon 164 results in screen 160 showing the list of staff members in the caregiver's unit in basically the same manner as shown in list 122 of screen 120 of FIG. 3. In some embodiments, main menu 106 is included at the bottom of screen 160.

Figure 7:
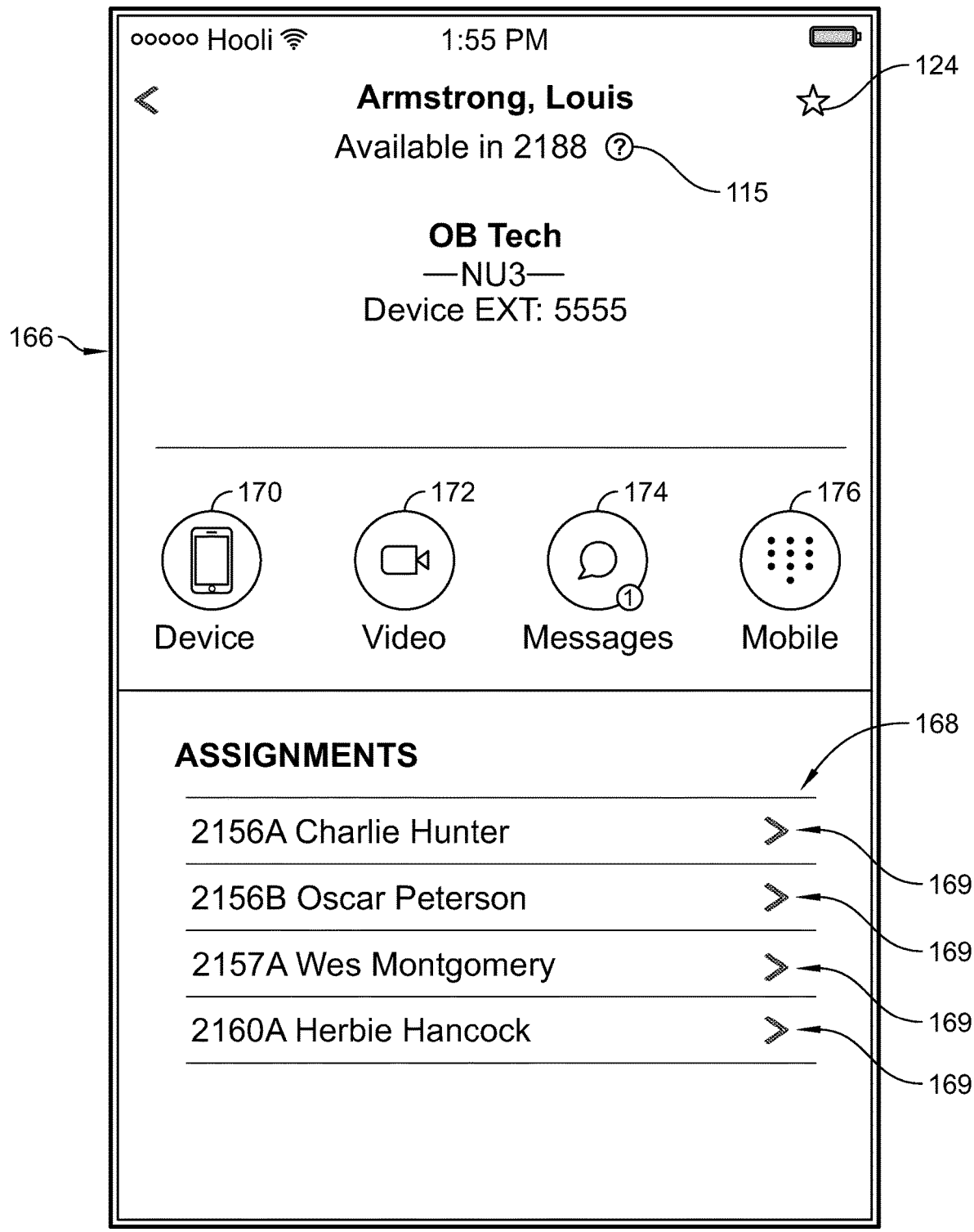
FIG. 7 is a screen shot of a Staff Detail screen that results in response to a staff member being selected on the My Team screen, the Staff Detail screen showing a list of patients assigned to the selected staff member and a set of communication icons that are selectable to communicate with the selected staff member via different communication methods.

Referring now to FIG. 7, a Staff Detail screen 166 appears on the display screen of the caregiver's mobile device 52 in response to a staff member name being selected on screen 120 of FIG. 3 or screen 160 of FIG. 6. A top section of Staff Detail screen 166 includes information about the selected staff member. In the illustrative example, Louis Armstrong is the selected caregiver's name. The selected caregiver is located in room 2188 and is available. The selected caregiver is an OB Tech of nursing unit NU3 and has a mobile device extension of 5555. A bottom section of Staff Detail screen 166 shows a list 168 of patients assigned to the selected staff member. For each line on list 168, a patient name is provided, the patient's assigned room is provided to the left of the patient's name, and a right arrow 169 is provided to the right of the patient's name. Each right arrow 169 is selectable to navigate to additional information about the respective patient.

Above the list 168 of assigned patients on screen 166 is a set of communication icons that are selectable to communicate with the selected staff member or, in one instance other caregivers, via different communication methods. In the illustrative example, the communication icons include a Device icon 170, a Video icon 172, a Messages icon 174, and a Mobile icon 176. Device icon 170 is selected to place a call directly to the mobile device 52 of the selected caregiver (e.g., Louis Armstrong in the given example). Video icon 172 is selected to record a video message to be sent to the selected caregiver. Messages icon 174 is selected to send a text message to the selected caregiver. Selection of Mobile icon 176 results in a telephone keypad being shown on the caregiver's mobile device 52 for dialing any desired phone number.

Figure 8:
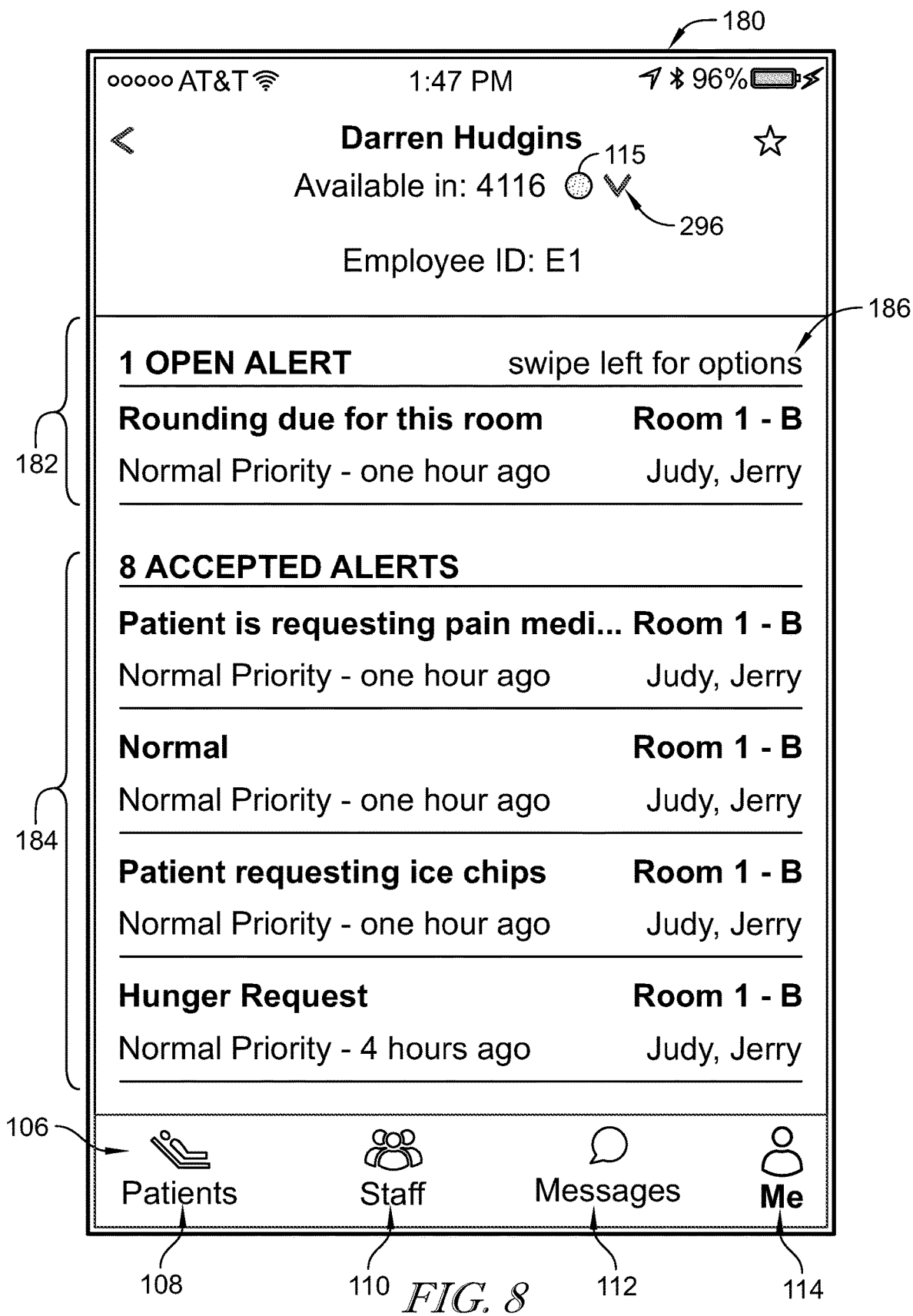
FIG. 8 is a screen shot of an Alert History screen that appears on the caregiver's mobile device in response to selection of a Me icon, the Alert History screen showing a list of open alerts and a list of accepted alerts for the caregiver.

Referring now to FIG. 8, an alternative Staff Detail screen 180 appears on the display screen of the caregiver's mobile device 52 in response to Me icon 114 of main menu 106 being selected. Screen 180 is an alternative to screen 100 of FIG. 2. The upper section of screen 180 of FIG. 8 is substantially the same as the upper section of screen 100 of FIG. 2 in that it includes the caregiver's name, location and employee identification (ID) number. In the illustrative example of FIG. 8, the employee's name is Darren Hudgins who is located in room 4116 and is available for answering voice calls, phone messages, and alerts as indicated by circle 115 being color coded green. Screen 180 includes a list of open alerts 182 and a list of accepted alerts 184 beneath the upper section.

In the illustrative example, there is one open alert 182 which states "Rounding due for this room" in connection with Room 1-B to which patient Jerry Judy is assigned. The illustrative open alert is designated as a Normal Priority alert and originated about one hour ago. A "swipe left for options" icon 186 is shown to the right of the text "1 OPEN ALERT" and is used by the caregiver to pull up an options menu by swiping left on the icon 186 or by swiping left on the open alert 182 itself. The options menu provides the caregiver with buttons for accepting the open alert or escalating the open alert to another caregiver. In some embodiments, the options menu associated with icon 186 also includes a button for accepting the alert and calling the patient room (see the discussion below of FIG. 16 regarding the "Accept & Call" option). The rounding alert message is originated from one or more of servers 86, 94, 98 according to this disclosure.

Still referring to FIG. 8, a heading at the top of the accepted calls 184 indicates that there are eight accepted alerts. However, only four of them can be seen on screen 180. Thus, the caregiver will need to scroll up or down on the display screen of the mobile device 52 to see the other accepted calls. The accepted calls that can be seen in FIG. 8 include calls indicating the following: "Patient is requesting pain medication," "Normal," "Patient is requesting ice chips," and "Hunger Request." All of these alert messages except for "Normal" originate in response to inputs by the patient, in this example Jerry Judy of room 1-B, on the respective patient tablet 56. The alert messages originated by the patient using tablet 56 are self-explanatory in this example. The "Normal" alert message may be initiated by the patient pressing a generic nurse call button provided on a siderail of the respective bed 54 or on the respective handheld pillow speaker unit 60, for example.

Figure 9:
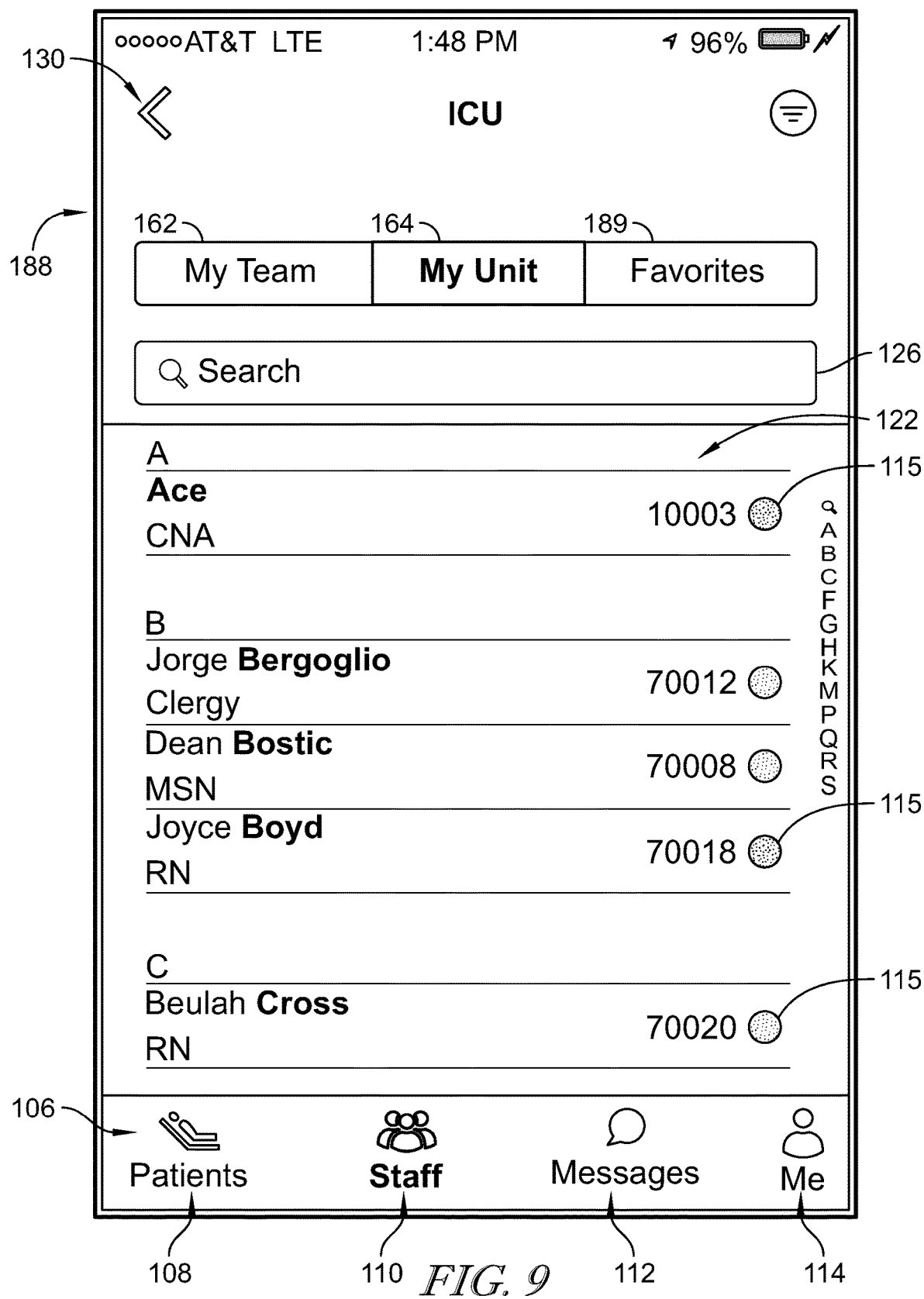
FIG. 9 is a screen shot of a My Unit screen showing a list of staff assigned to the same unit as the caregiver.

Referring now to FIG. 9, a My Unit screen 188 appears on the display screen of the caregiver's mobile device 52 in some embodiments in response to Staff icon 110 of main menu 106 being selected. Screen 188 is another alternative to screen 120 of FIG. 3 and screen 160 of FIG. 6. Thus, like reference numbers are used to indicate aspects of screen 188 that are the same or substantially similar to those of screens 120, 160. Thus, like screen 120 of FIG. 3, screen 188 of FIG. 9 shows a list of staff assigned to the same unit as the caregiver. The primary difference between screen 188 of FIG. 9 and screens 120, 160 is the inclusion of a Favorites icon 189 which is selectable to have a list of staff members that the caregiver and/or the mobile caregiver application has designated as "favorites" displayed on the display screen of the respective mobile device 52.

Figure 10:
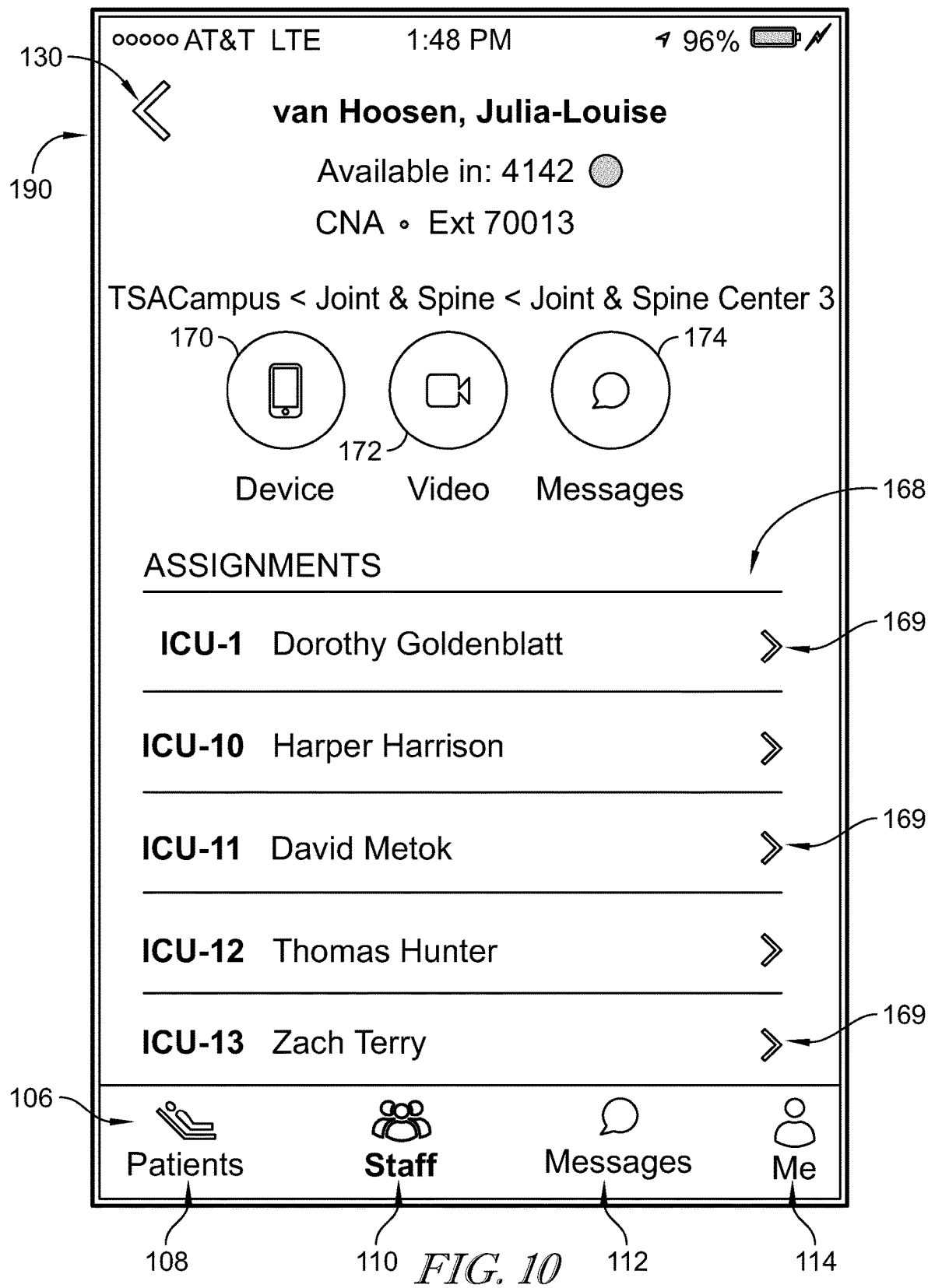
FIG. 10 is a screen shot, similar to FIG. 7, of an alternative Staff Detail screen that results in response to a staff member being selected on the My Unit screen of FIG. 9, the alternative Staff Detail screen showing a list of patients assigned to the selected staff member and a set of communication icons that are selectable to communicate with the selected staff member via different communication methods.
Figure 11:
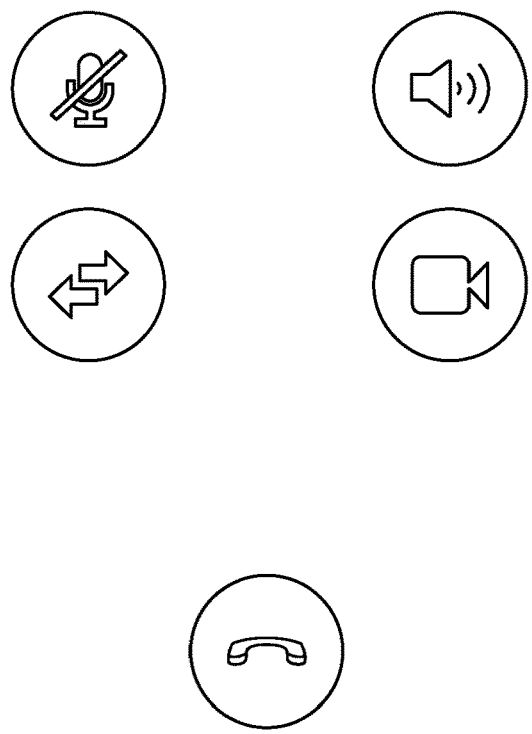
FIG. 11 is a screen shot of a Call screen that results when a Device icon is selected on the alternative Staff Detail screen of FIG. 10 to call the mobile device of the selected staff member.

Referring now to FIG. 10, which is similar to FIG. 7, an alternative Staff Detail screen 190 appears on the display screen of the caregiver's mobile device 52 in response to a staff member being selected on the My Unit screen 188 of FIG. 9. In the illustrative example, Julia-Louise van Hoosen is the staff member that was selected on screen 188 of FIG. 9 after the caregiver scrolled down to her name. Like screen 166 of FIG. 7, the alternative Staff Detail screen 190 of FIG. 10 shows a list 168 of patients assigned to the selected staff member and the set of communication icons 170, 172, 174 (icon 176 is omitted from the screen 190) that are selectable to communicate with the selected staff member via different communication methods as described above. Screen 190 also has a text string stating "TSACampus<Joint & Spine<Joint & Spine Center 3" which indicates further information about the unit to with the selected caregiver is assigned. In response to Device icon 170 being selected on screen 190 of FIG. 10, a voice call is placed directly to the mobile device 52 of the selected caregiver as shown by the Call screen 192 of FIG. 11. This voice call is a secure voice call and involves only equipment included in system 50 such as VoIP switch and Enterprise server 84. The voice call from the caregiver to the selected caregiver is not routed through any equipment included in public infrastructure outside of system 50 of the healthcare facility. This is in contrast to any calls placed using the phone keypad associated with Mobile icon 176 of screen 166 of FIG. 7 which places a regular phone call over the public telephone infrastructure that is external to system 50.

Figure 12:
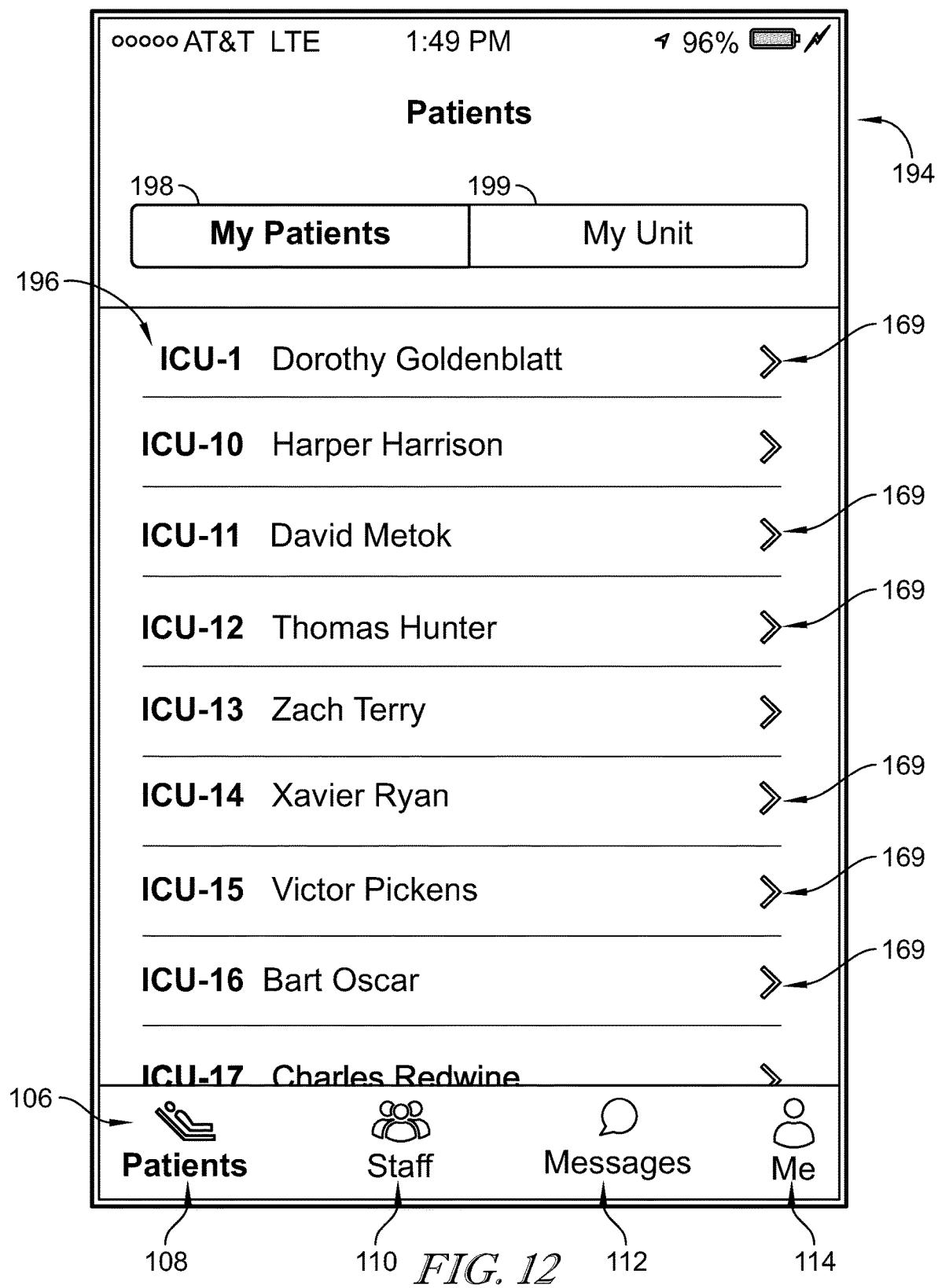
FIG. 12 is a screen shot of a My Patients List screen showing a list of patients assigned to the caregiver, the My Patients List screen being shown in response to a Patients icon being selected on the main menu at the bottom of the screen.

Referring now to FIG. 12, a My Patients List screen 194 appears on the caregiver's mobile device 52 in response to the Patients icon 108 being selected on main menu 106. Screen 194 includes a list 196 of patients assigned to the caregiver. The room assignment for each patient is shown to the left of the patient's name in each row of list 196 and right arrows 169 are shown to the right of the patient's name in each row to indicate that selection of the row, the icon 169, or the patient's name results in more information about the selected patient being displayed on the display screen of the mobile device 52. Screen 194 includes a My Patients button 198 and an adjacent My Unit button 199 located above list 196. In the illustrative example, button 198 is highlighted to indicate that list 196 includes the name of the patients assigned to the caregiver. In response to selection of button 199 all patients in the caregiver's unit are included in list 196.

Figure 13:
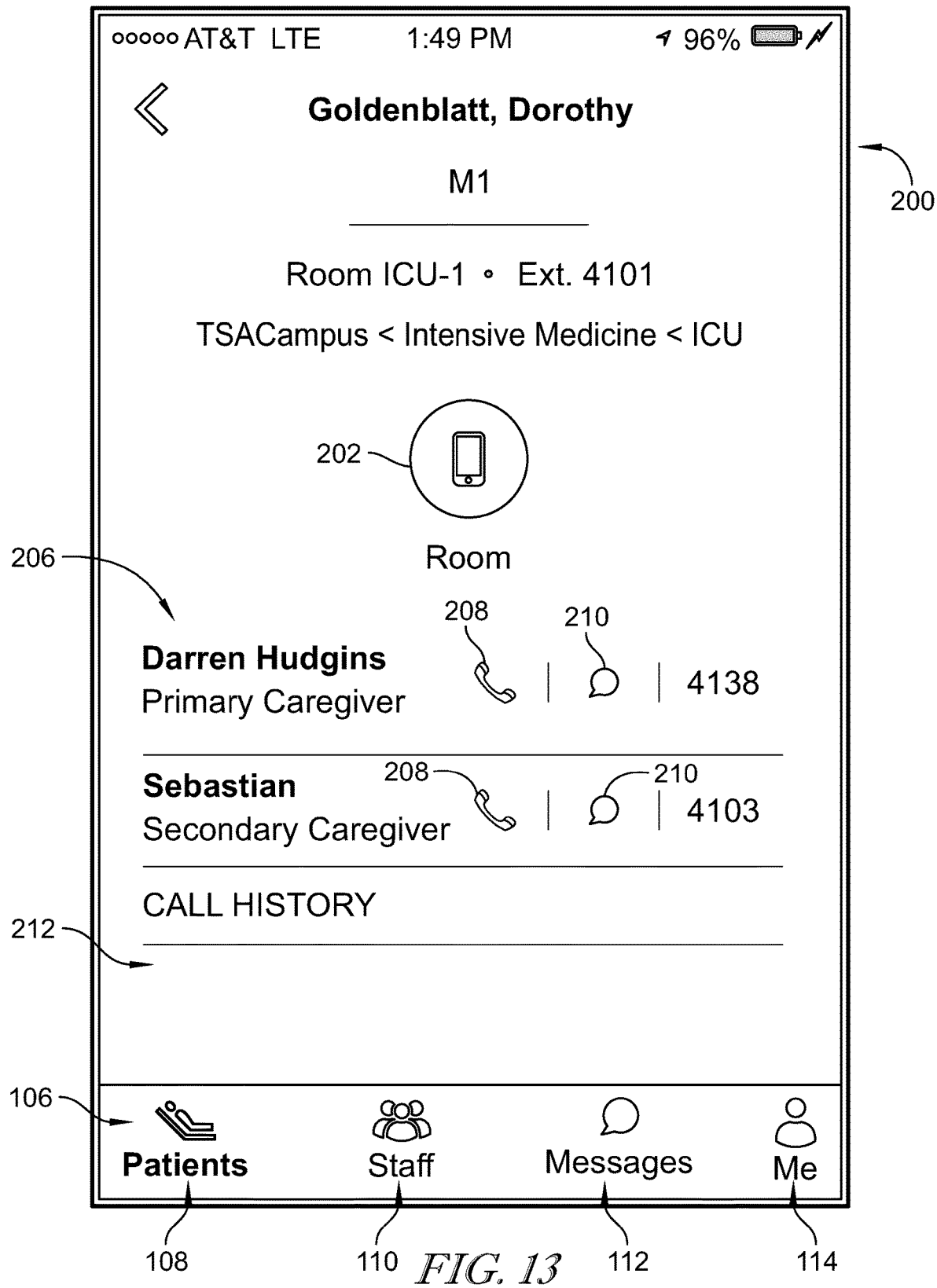
FIG. 13 is a screen shot of a Patient Details screen showing a list of caregivers assigned to a patient selected on the My Patients List screen of FIG. 12 and showing a Room icon that can be selected to call the room in which the patient is assigned.
Figure 14:
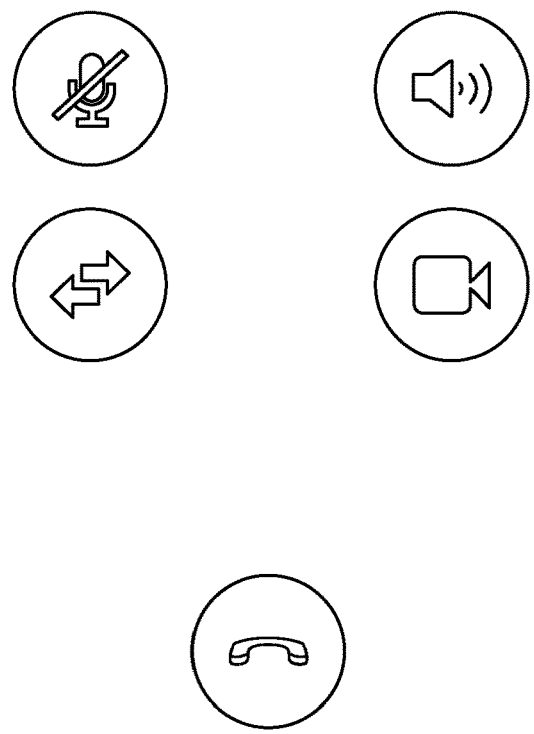
FIG. 14 is a screen shot of a Call screen that results when the Device icon of FIG. 13 is selected to call the patient's room.

Referring now to FIG. 13, a Patient Details screen 200 appears on the display screen of the caregiver's mobile device 52 in response to selection of the row, the icon 169, or the patient's name on list 196 of screen 194 of FIG. 12. The upper section of screen 200 includes the patient's name, room assignment, room extension, medical records number (MRN) or other patient identification number, and the patient's unit information. In the illustrative example of FIG. 13, the patient's name is Dorothy Goldenblatt having MRN M1. The patient is assigned to room ICU-1 which has an extension of 4101. The patient's unit information is shown as "TSACampus<Intensive Medicine<ICU."

Beneath the patient information at the top section of screen 200 is a Room icon 202 that is selectable by the caregiver to place a call to the patient's assigned room. In response to icon 202 of screen 200 being selected, a communications channel is opened within system 50 between the caregiver's mobile device 52 and the respective audio station 62, 64 in the patient's assigned room location. Thus, the extension number of the patient's room refers to the extension number associate with the audio station 62, 64 of the room location to which the patient is assigned. The communications channel includes the equipment of system 50 that is used to route voice packets between the mobile device 52 and the audio station 62, 64. Thus, the equipment involved in such a communication channel includes, for example, VoIP Switch and Enterprise Server 84, PoE switch 76, and I/O Board 68. In response to Room icon 202 being selected on screen 200 of FIG. 13, a Call screen 204 shown in FIG. 14 appears on the display screen of the caregiver's mobile device.

Still referring to FIG. 13, screen 200 includes a list 206 of caregivers that are assigned to the selected patient. In the illustrative example, Darren Hudgins is the primary caregiver assigned to the selected patient and Sebastian is the secondary caregiver assigned to the selected patient. To the right of each of the assigned caregiver's name in list 206 are a phone icon 208, a message icon 210, and the caregiver's mobile device extension number. Selection of icon 208 results in a secure voice call being placed to the mobile phone 52 of the respective caregiver and selection of icon 210 results in a screen appearing on the caregiver's mobile device 52 for sending a text message to the respective caregiver. Illustrative screen 200 includes a Call History window 212 beneath list 206. In the given example, window 212 is blank. However, it should be understood that window 212 becomes populated with the various calls (aka alerts or alert messages) generated in system 50 in connection with the selected patient as they occur during the selected patient's stay in the healthcare facility.

Figure 15:
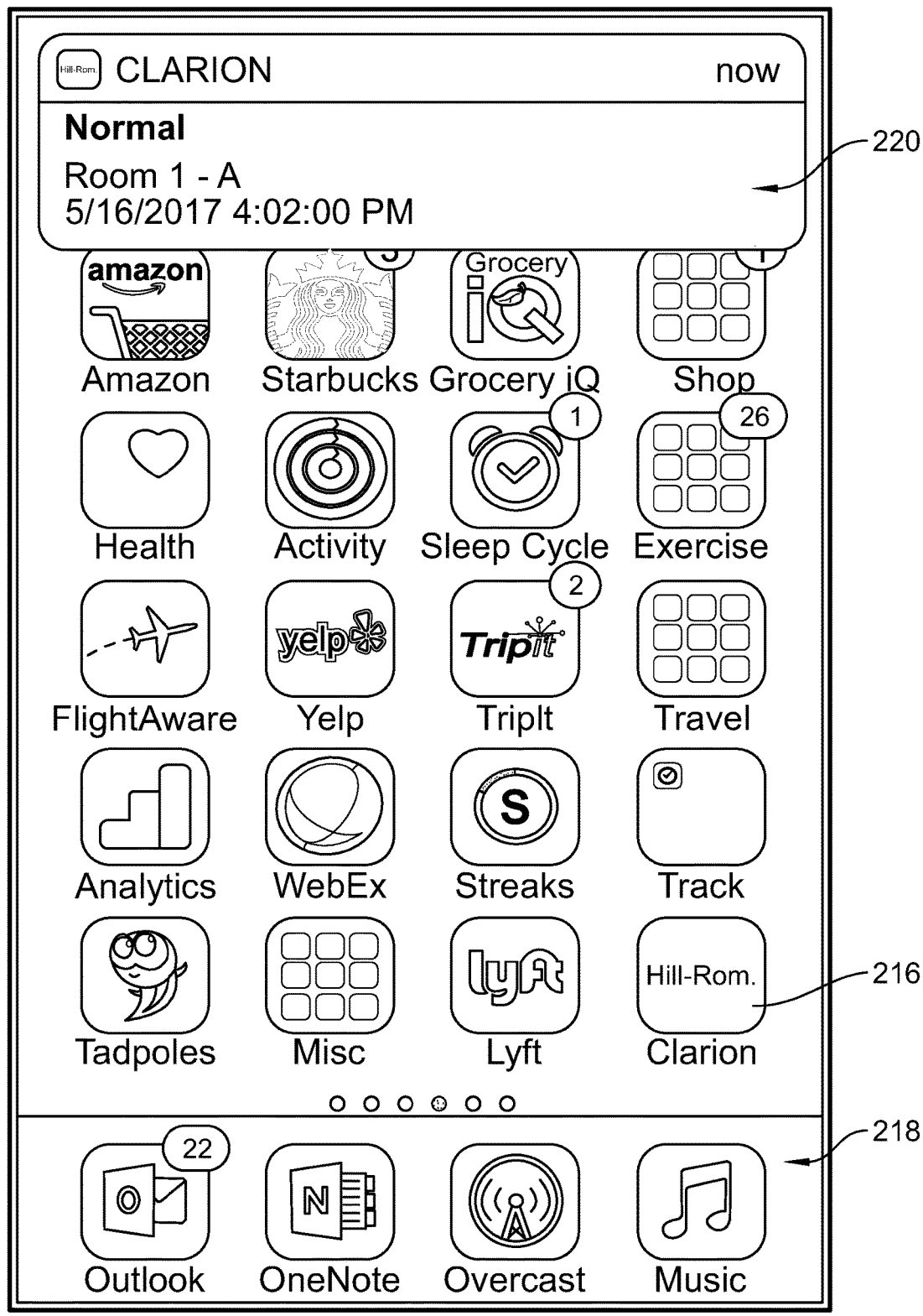
FIG. 15 is a screen shot of a Home screen of the caregiver's mobile device showing an icon or tile in the in the lower right corner, but above the main menu bar at the bottom of the screen, to indicate that the caregiver and staff communication software application has been downloaded (or uploaded) to the caregiver's mobile device and showing an incoming alert message at the top of the screen.

Referring now to FIG. 15, an example of a Home screen 214 of the caregiver's mobile device 52 is provided. Home screen 214 has an icon or tile 216 in the in the lower right corner (but above a main menu bar 218 at the bottom of the screen 214). The presence of tile 216 on screen 214 indicates that the mobile software application described herein has been successfully downloaded (or uploaded) to the caregiver's mobile device 52. In the illustrative example, screen 214 of FIG. 15 has a window 220 which displays information about an incoming alert message at the top of the screen 214. Thus, window 220 appears on the Home screen 214 of the caregiver's mobile device 214 in those instances in which an incoming alert message for the caregiver has been generated within system 50 when the mobile caregiver application has not yet been opened on the mobile device 52 by selection of tile 216. In the illustrative example, window 220 includes text indicating that a Normal alert originated from Room 1-A. A date and time at which the alert message was generated is also shown in window 220.

Figure 16:
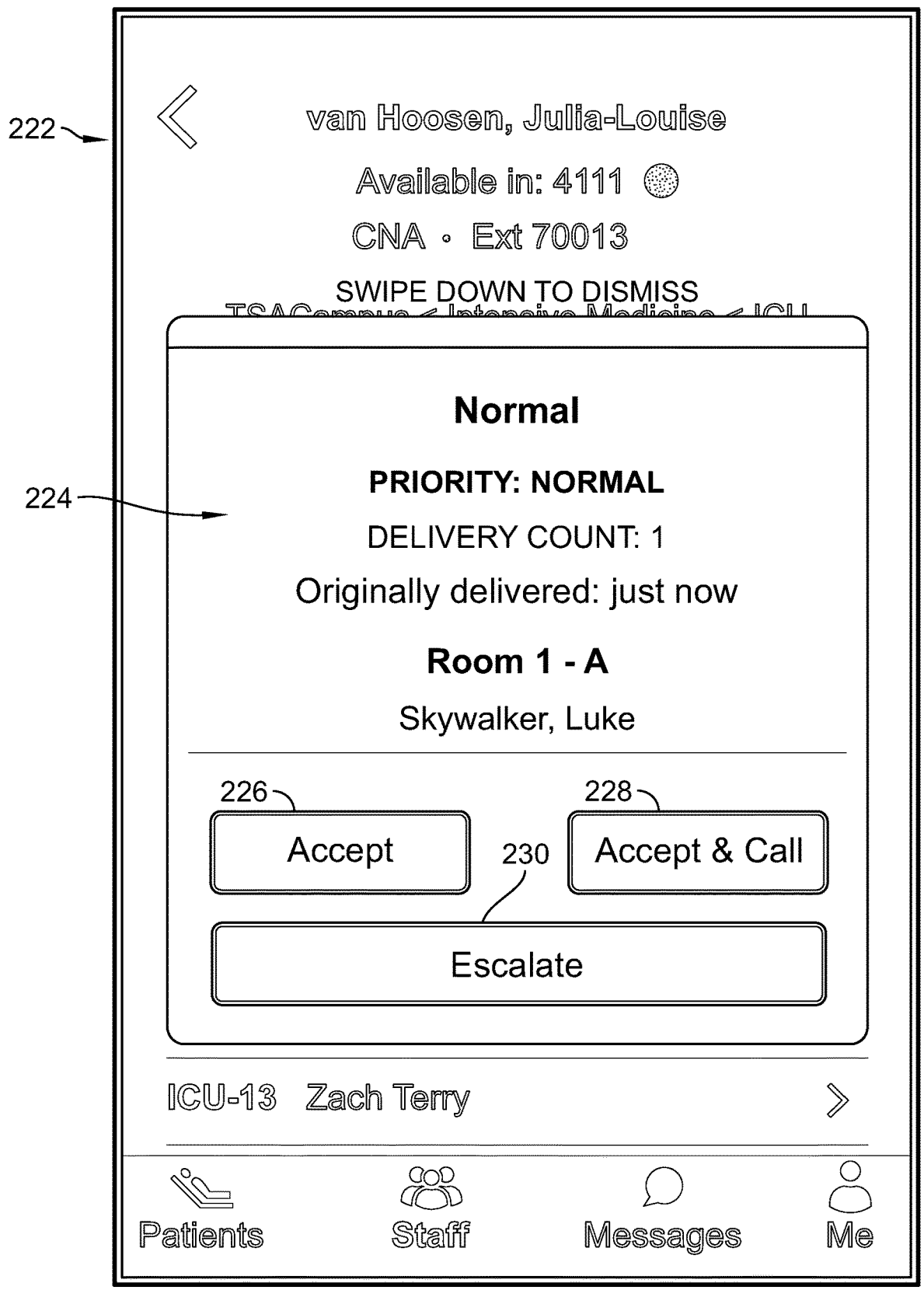
FIG. 16 is a screen shot of a Call Details screen that appears on the caregiver's mobile device in response to the incoming alert message of FIG. 15 being selected by the caregiver, the Call Details screen including buttons or icons that are selectable by the caregiver to accept responsibility for responding to the alert message, to accept responsibility for responding to the alert message and to place a call to the room of the patient from which the alert message originated, or to escalate the alert message to another caregiver.

Referring now to FIG. 16, a Call Details screen 222 appears on the caregiver's mobile device 52 in response to the incoming alert message shown of window 220 of FIG. 15 being selected by the caregiver. The Call Details screen 222 includes a window 224 having further information about the incoming alert message. For example, the patient's name (Luke Skywalker in the given example) is included in window 224 along with the alert type, alert priority, delivery count and original delivery time. Beneath the alert information, window 224 includes an Accept icon 226, an Accept & Call icon 228, and an Escalate icon 230. In response to selection of icon 226, the caregiver accepts responsibility for responding to the alert message and the alert message of window 224 is added to the list of the caregiver's accepted alerts. In response to selection of icon 228, the caregiver accepts responsibility for responding to the alert message, which is added to the list of the caregiver's accepted alerts, and a voice call is placed to the audio station 62, 64 of the room of the patient from which the alert message originated. In response to selection of icon 230, the alert message is escalated to another caregiver such as the assigned secondary caregiver for the patient.

Figure 17:
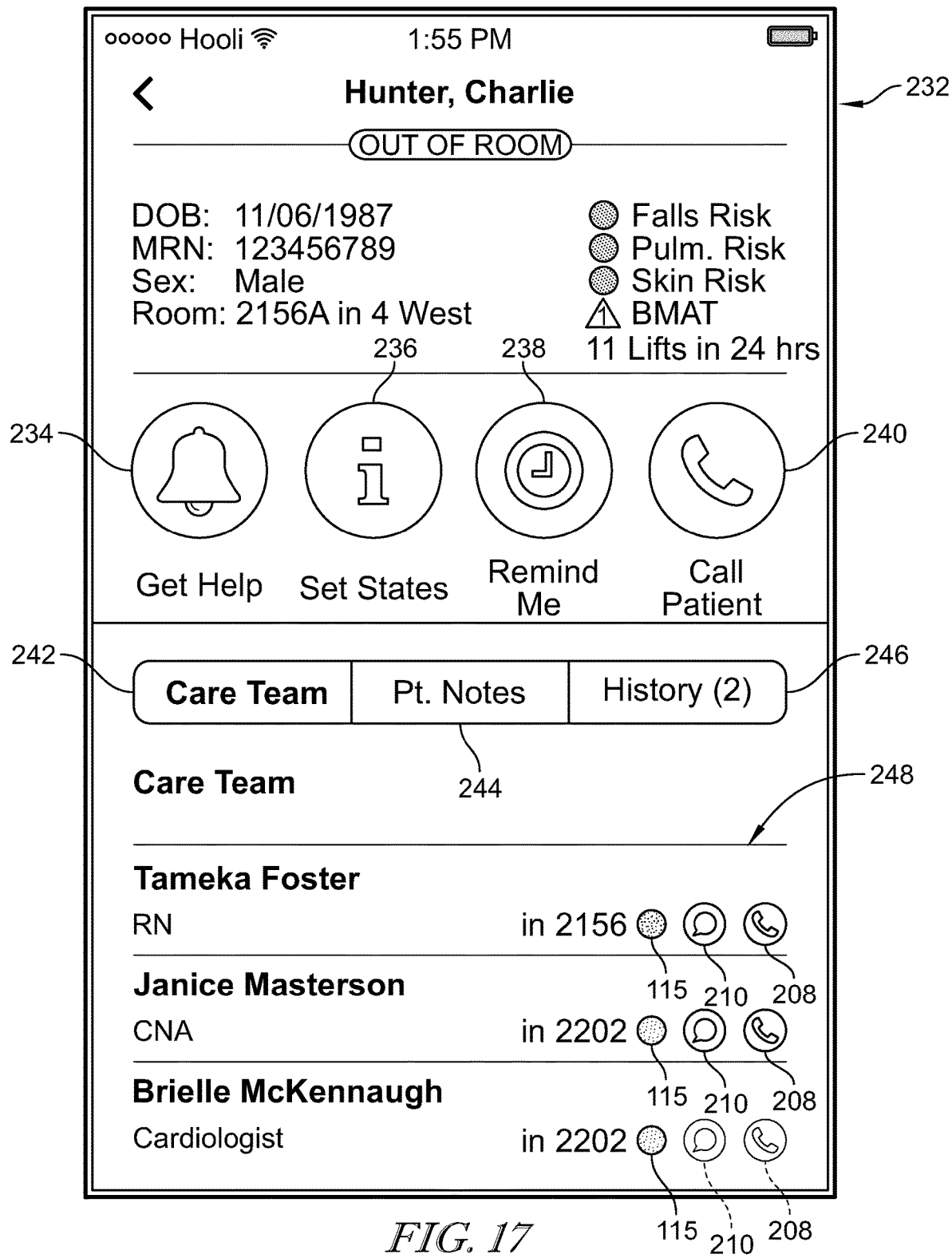
FIG. 17 is a screen shot of a Patient Detail screen that appears on the caregiver's mobile device in response to a patient name being selected on the Staff Detail screen of FIG. 7, the Patient Detail screen including an upper section having information indicating the patient's location, date of birth, sex, and medical risks, and having a set of icons including one that permits the caregiver to call into the patient's room and the Patient Detail screen having a bottom section including icons for selecting a Care Team list, patient notes, and call history.

Referring now to FIG. 17, a Patient Detail screen 232 appears on the caregiver's mobile device 52 in response to a patient name being selected on the Staff Detail screen 166 of FIG. 7. The Patient Detail screen 232 includes an upper section having information indicating the patient's name, the patient's location, date of birth, MRN, sex, assigned room, and medical risks. In the illustrative example, the patient's name is Charlie Hunter (the first patient on list 168 in FIG. 7) who is indicated as being located "OUT OF ROOM." Also in the illustrative example, the patient has been indicated as having a Falls Risk, a Pulmonary Risk, and a Skin Risk. The patient also has a BMAT of one and there have been 11 lifts of the patient in the preceding 24 hours for the patient.

Beneath the patient information and medical risk information, screen 232 includes a Get Help icon 234, a Set States icon 236, a Remind Me icon 238, and a Call Patient icon 240. Selection of icon 234 results in a message being sent to the master nurse station 78 to request one or more additional caregivers come to the caregiver's location and provide assistance. Selection of icon 238 results in a screen that permits the caregiver to set up one or more reminders to be displayed on the display screen of the caregiver's mobile device 52 at a selected future time. Selection of icon 240 results in a voice call being placed to the audio station 62, 64 in the patient's assigned room (Room 2156A in the given example of FIG. 17). Selection of icon 236 results in a screen that is discussed below in connection with FIG. 18.

Still referring to FIG. 17, screen 2323 has a bottom section including a Care Team button 242, a Pt. Notes button 244, and a History button 246. In the illustrative example, icon 242 has been selected and is highlighted. In response to selection of icon 242, a Care Team list 248 is shown in the bottom section of screen 232. Care Team list 248 lists the team of caregivers assigned to the patient. Each row in list 248 includes the staff members name, staff title beneath the name, the current location of the caregiver as determined by the RTLS, circle icon 115 with color coding to indicate availability status, message icon 210, and phone icon 208. The descriptions above of icons 115, 208, 210 is equally applicable to FIG. 17 and does not need to be repeated. In the illustrative example, icons 208, 210 for Cardiologist Brielle McKennaugh are greyed out to indicate that voice calls and text messaging are not currently possible for that staff member.

Selection of icon 244 results in a patient notes window appearing in the bottom section of screen 232 for the caregiver to enter patient notes. Selection of icon 246 results in a call history window, similar to window 212 of FIG. 13, appearing in the bottom section of screen 232. The call history window shows the previous calls (e.g., alert message information) for the patient. In the illustrative example, the number "(2)" appears next to "History" within button 246 to indicate there are two previous calls that will appear in the call history window in response to button 246 being selected.

Figure 18:
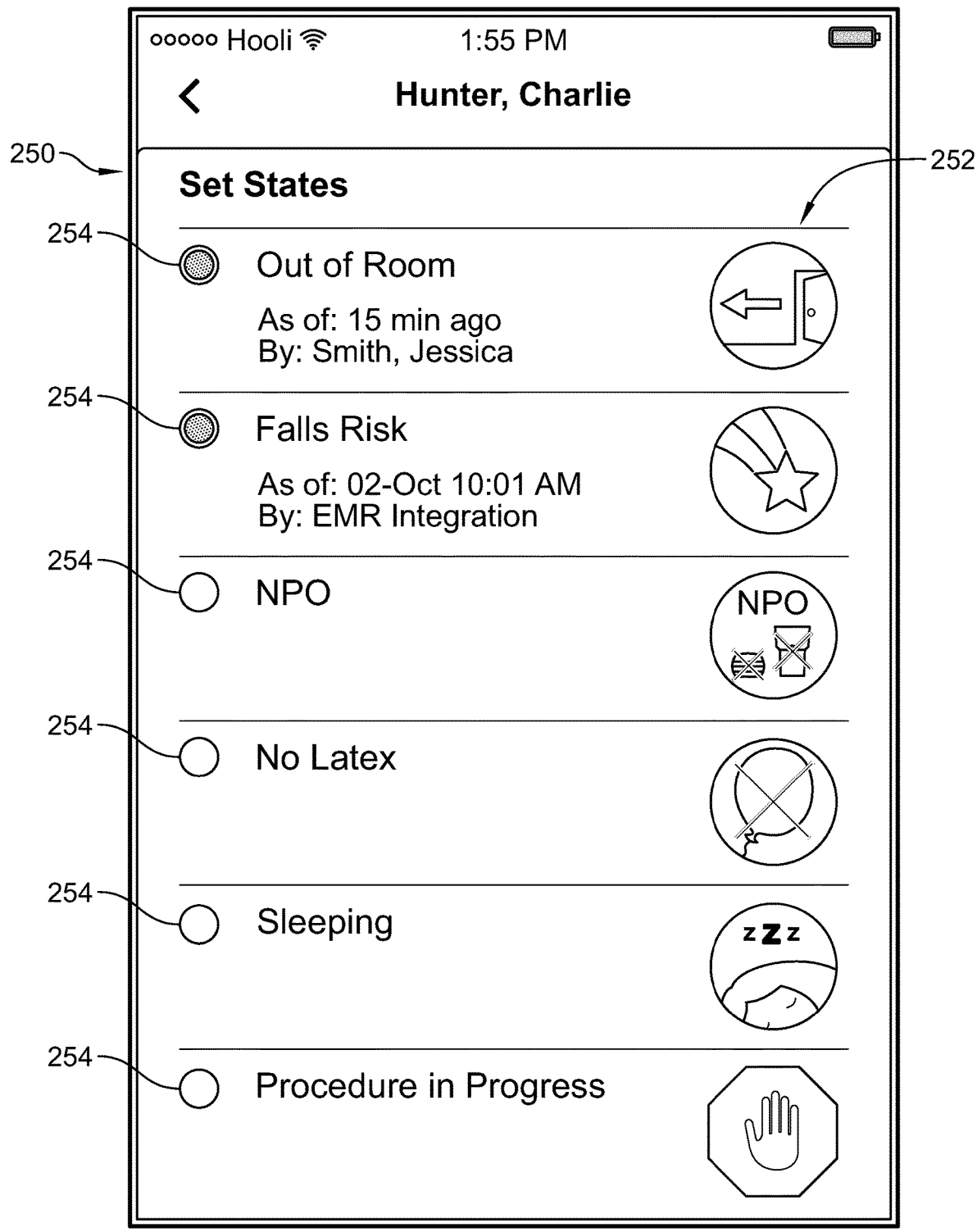
FIG. 18 is a screen shot of a Set States screen that appears on the caregiver's mobile device in response to a Set States icon being selected on the Patient Detail screen of FIG. 17, the Set States screen including a menu having selections for Out of Room, Falls Risk, NPO, No Latex, Sleeping, and Procedure in Progress.

Referring now to FIG. 18, a Set States screen 250 appears on the caregiver's mobile device 52 in response to the Set States icon 236 being selected on the screen 232 of FIG. 17. The Set States screen 250 includes a menu 252 of states that are selectable for the patient. In the illustrative example of FIG. 18, the following states are shown on menu 252 from top to bottom: Out of Room, Falls Risk, NPO, No Latex, Sleeping, and Procedure in Progress. These states are self-explanatory except for, perhaps, NPO which is an abbreviation for the Latin phrase "nil per os" which means nothing by mouth. Other states of menu 252, such as Pulmonary Risk and Skin Risk, can be viewed by scrolling up or down in the menu 252. Each state includes a radio button 254 that is filled in if the state is selected and that is empty if the state is not selected. In the illustrative example, radio buttons 254 in the Out of Room and Falls Risk rows of menu 252 have been selected and each of the others have not.

Still referring to FIG. 18, in the Out of Room row of menu 252, information is provided to indicate that the Out of Room selection was made 15 minutes ago by Jessica Smith who is a different caregiver than the one viewing menu 252 on their mobile device 52. In the Falls Risk row of menu 252, information is provided to indicate that the Falls Risk selection was made October 2, at 10:01 am by EMR Integration (e.g., the EMR system portion of overall system 50 including EMR server 94). Thus, it is contemplated by this disclosure patient states may be selected using various equipment of system 50 other than each individual caregiver's mobile device 52. It is also contemplated by this disclosure that each caregiver can select and de-select patient states on menu 252 using their individual mobile devices. Subsequent taps of the state names in each row of menu 252 or respective radio buttons 254 or graphical icons at the right of each row in menu 252 result in selection and de-selection of the respective patient states.

Figure 19:
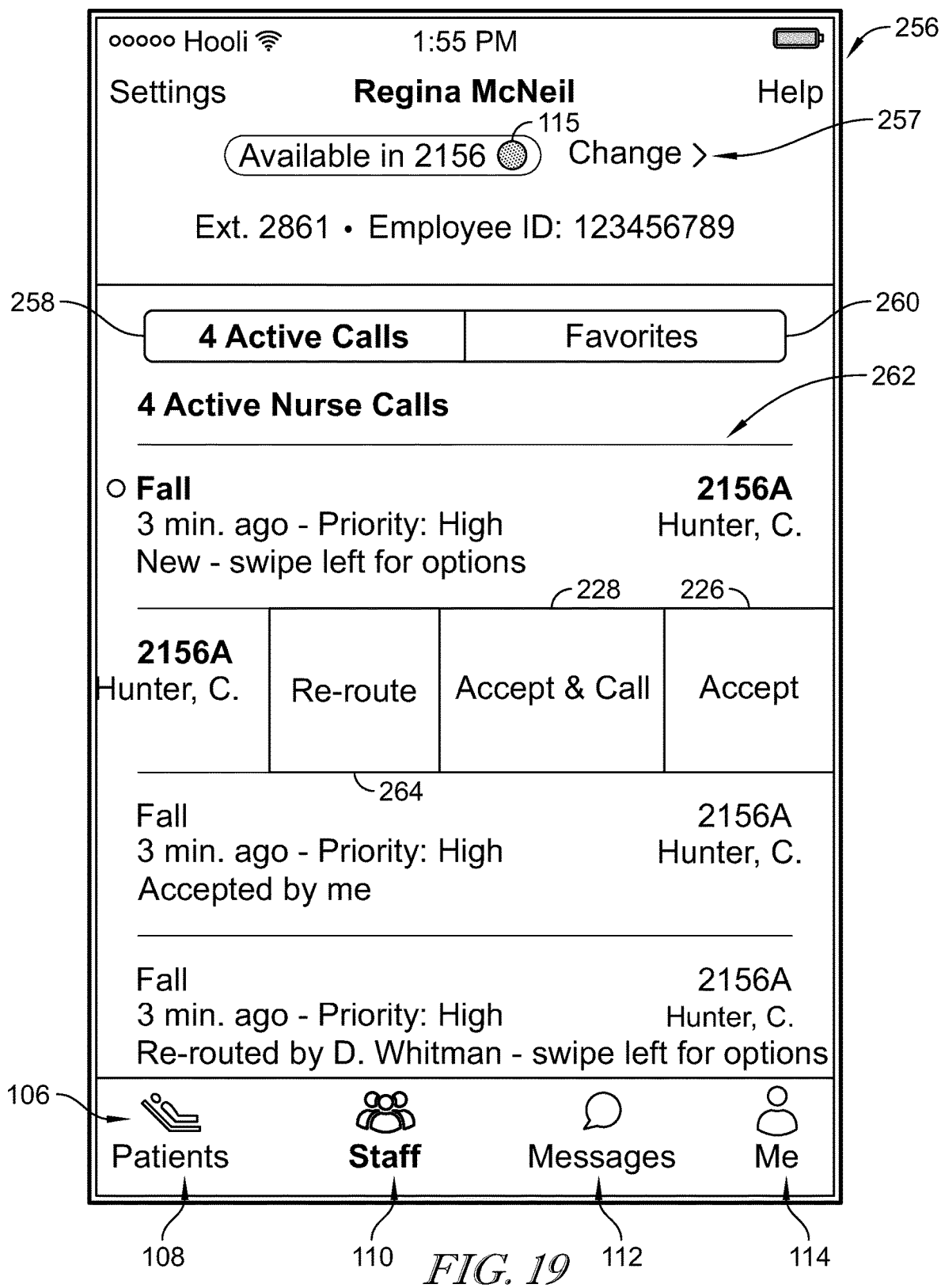
FIG. 19 is screen shot of a Staff Member Detail screen that appears on the caregiver's mobile device in response to selection of a staff member's name on any screen having a list of staff members such as the screens of FIGS. 3, 6 and 9, the Staff Member Detail screen having a list of active calls for the selected staff member.

Referring now to FIG. 19, a Staff Member Detail screen 256 appears on the caregiver's mobile device 52 in response to selection of a staff member's name on any screen having a list of staff members such as the screens 120, 160, 188 of FIGS. 3, 6 and 9, respectively. The top section of screen 256 includes information about the selected caregiver such as the selected caregiver's name, location, availability status, mobile device 52 extension, and employee ID. A Change icon 257 is also provided in the top section of screen 257 for selection by the caregiver to return back to the previous screen having a list of staff members from which to select. Beneath the selected caregiver information, the Staff Member Detail screen 256 has an Active Calls button 258 and a Favorites button 260. In the give example, button 258 is selected resulting in a list 262 of active calls for the selected staff member appearing on the display screen of the caregiver's mobile device 52.

In the illustrative example of FIG. 19, the first row of list 262 represents a new or incoming call. In particular, the call is a Fall alert message that originated three minutes ago and that has high priority. In connection with the incoming call on screen 256, Accept button 226 and Accept & Call button 228 are provided. The description above buttons 226, 228 in connection with FIG. 16 is equally applicable to these same buttons on screen 256 of FIG. 19. To the left of button 228 on screen 256 is a Re-Route button 264. Button 264 is similar to Escalate button 230 but instead of escalating to the secondary caregiver, selection of Re-Route button 264 allows the caregiver to designate a particular caregiver, such as one who has not been designated as the secondary caregiver, to which the call is to be re-routed. At the bottom of list 262 is a call that has been re-routed to the caregiver by D. Whitman.

Figure 20:
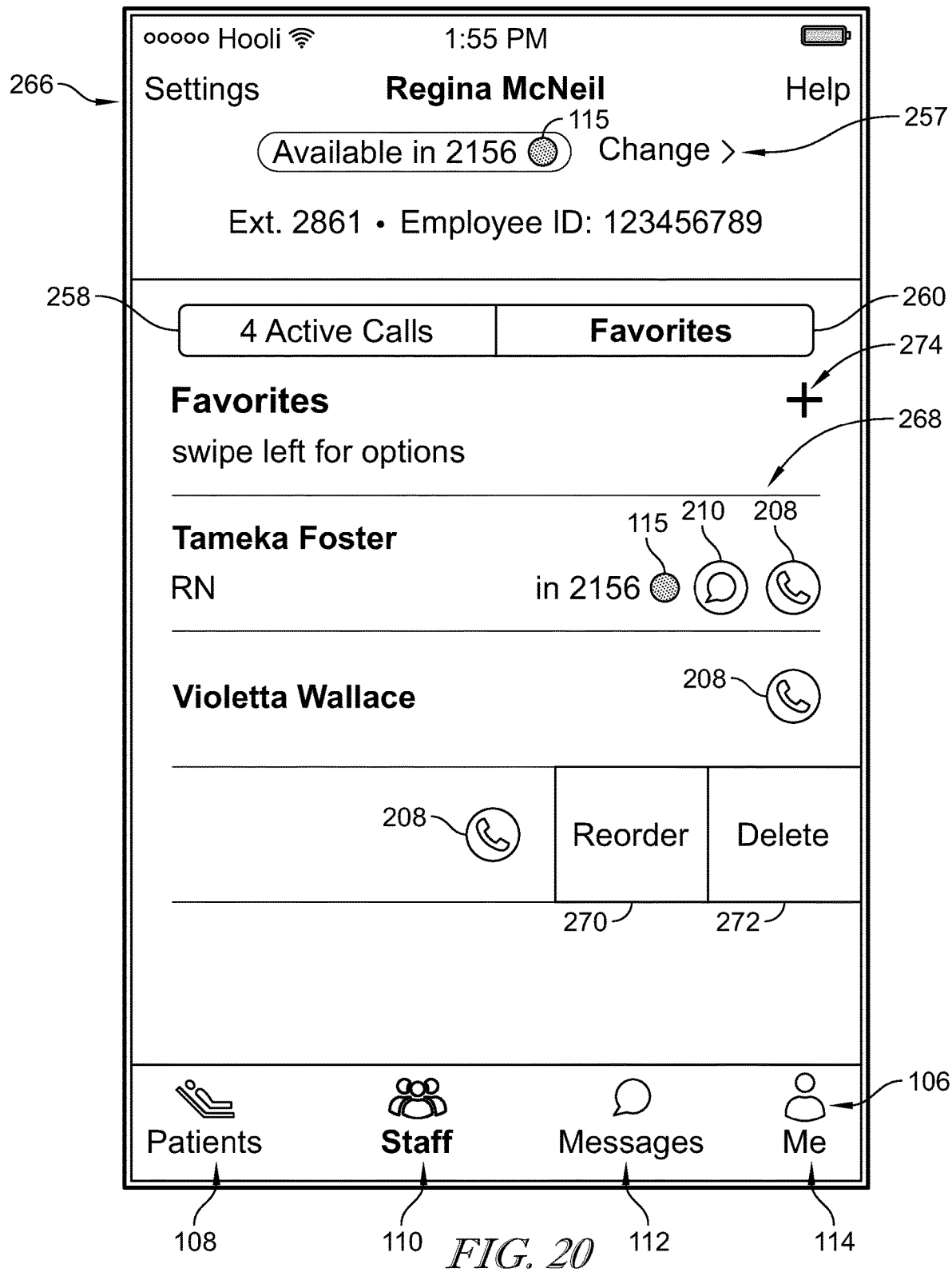
FIG. 20 is screen shot of a Favorites screen that appears on the caregiver's mobile device in response to a Favorites icon being selected on the Staff Member Detail screen of FIG. 19, the Favorites screen including a list of favorite contacts for the selected caregiver.

Referring now to FIG. 20, a Favorites screen 266 appears on the caregiver's mobile device 52 in response to the Favorites icon 260 being selected on the Staff Member Detail screen 256 of FIG. 19. The Favorites screen 266 includes a list 268 of favorite contacts for the selected caregiver. The features and functions of icons 115, 208, 210 appearing on screen 266 are the same as previously described herein. Screen 266 includes a Reorder button 270 and a Delete button 272. Selection of button 270 results in various options for reordering the staff names on list 268 being presented on the display screen of the caregiver's mobile device 52. For example, the names may be sorted by unit, staff title, alphabetically, availability, and so forth. Selection of button 272 permits the caregiver to select names on the list 268 for deletion from the list 268. Screen 266 also has a "+" icon 274 (aka an Add icon 274) which can be selected to add new staff members to the list 268.

Figure 21:
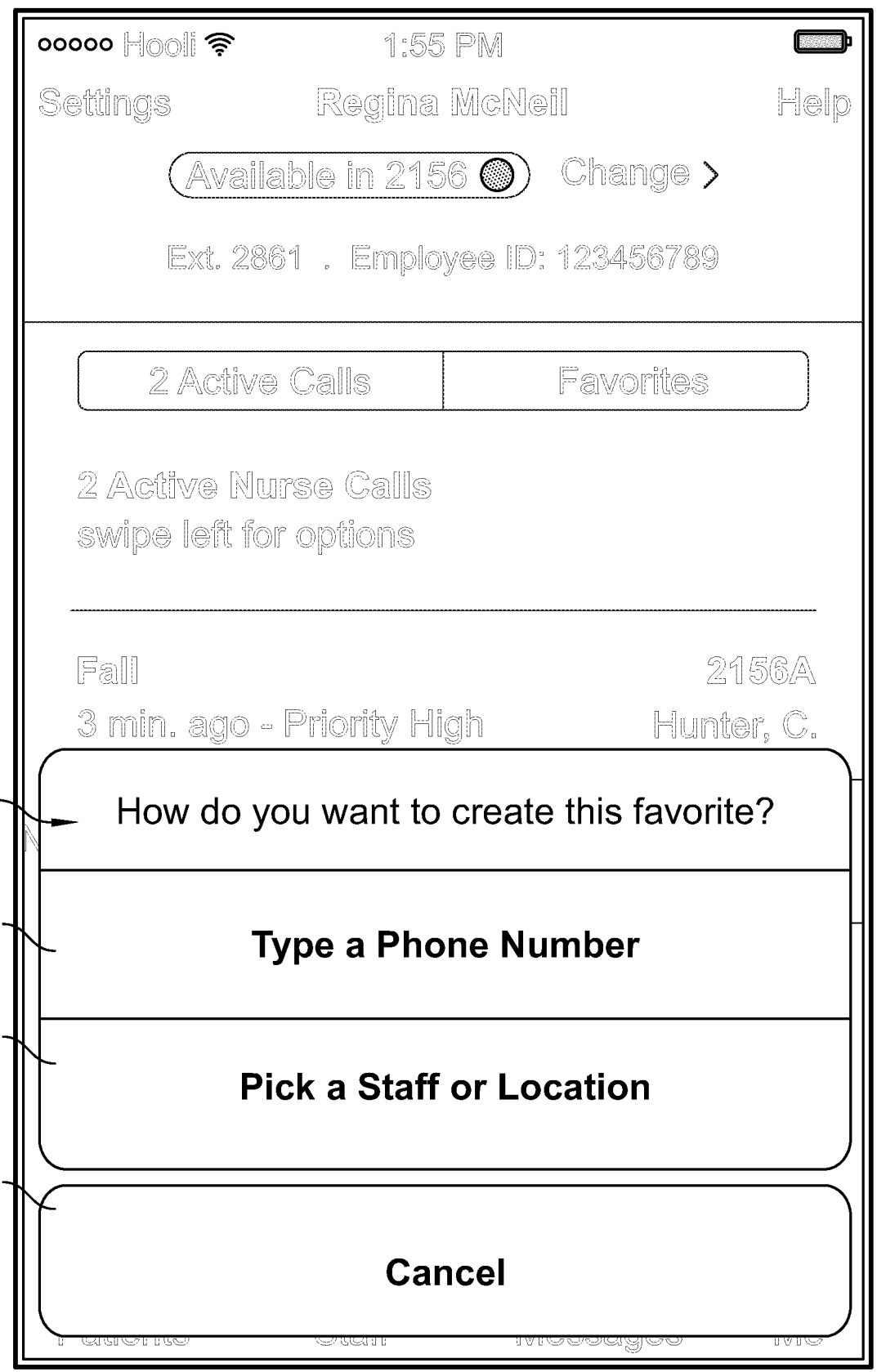
FIG. 21 is a screen shot of an Add Favorites screen that appears on the caregiver's mobile device in response to an Add icon being selected on the Favorites screen of FIG. 20, the Add Favorites screen including a window for selecting whether a favorite is to be added by typing a phone number or by picking a staff or location.

Referring now to FIG. 21, an Add Favorites screen 276 appears on the caregiver's mobile device 52 in response to the Add icon 274 being selected on the Favorites screen 266 of FIG. 20. The Add Favorites screen 276 including a window 278 having a first button 280 which is selected if the caregiver wishes to add a favorite by typing a phone number and having a second button 282 which is selected if the caregiver wishes to add a favorite by picking a staff or location. A Cancel button 284 is provided on screen 276 beneath the window 278 and is selected by the caregiver if the caregiver no longer wishes to add a favorite to list 268 of screen 266.

Figure 22:
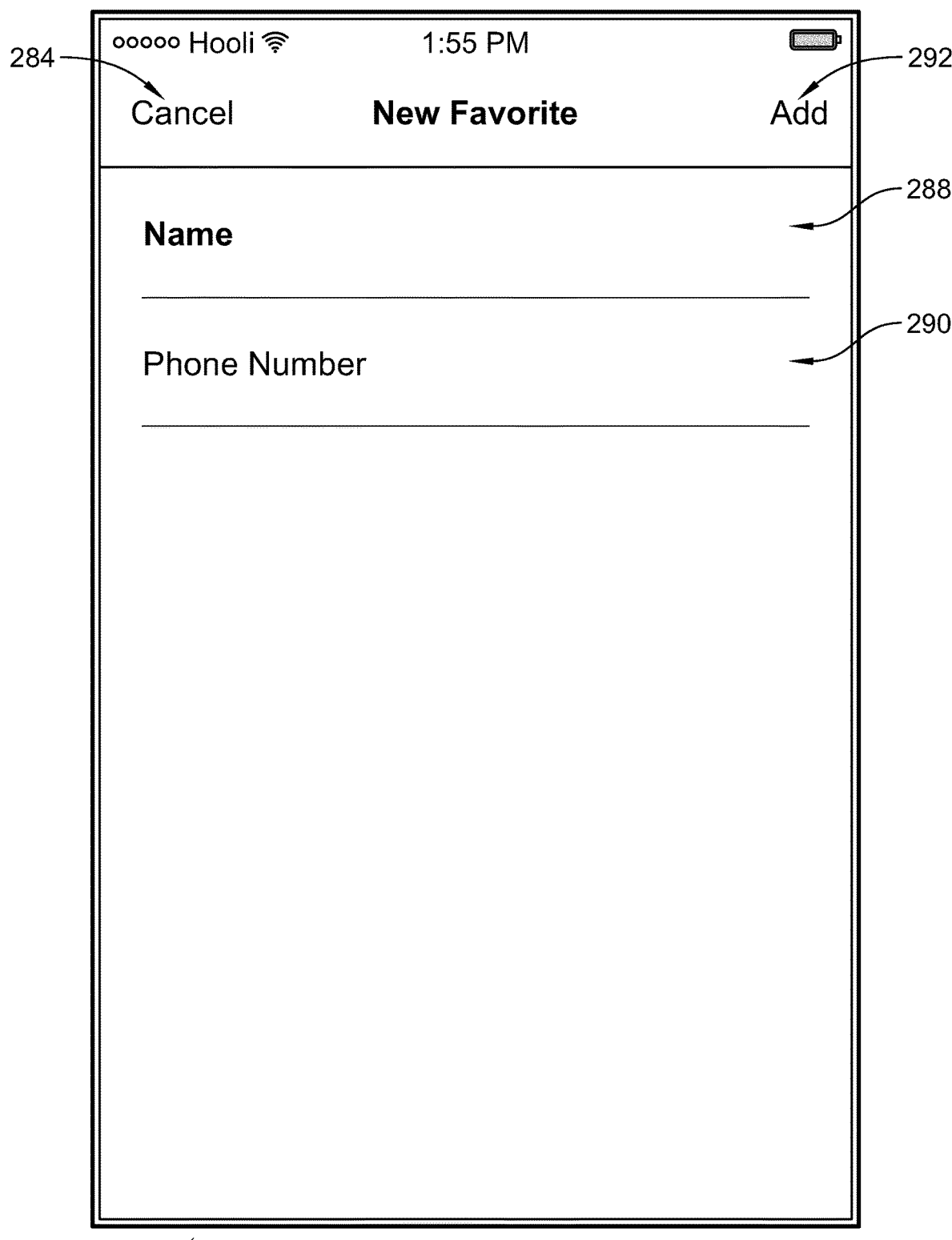
FIG. 22 is a screen shot of a New Favorites screen that appears on the caregiver's mobile device in response to a Type a Phone Number icon being selected on the Add Favorites screen of FIG. 21, the New Favorites screen including fields for typing a Name and Phone Number of the staff member to be added as a new favorite.

Referring now to FIG. 22, a New Favorites screen 286 appears on the caregiver's mobile device 52 in response to the Type a Phone Number icon 280 being selected on the Add Favorites screen 276 of FIG. 21. The New Favorites screen 286 includes first and second fields 288, 290 for typing a Name and Phone Number, respectively, of the staff member to be added as a new favorite. An Add icon 292 is provided at the top right of screen 286 and is selected by the caregiver to add the staff member designated in fields 288, 290 to the list 268 of favorites. Cancel button 284 is provided at the top left of screen 286 and is selected by the caregiver if the if the caregiver no longer wishes to add a favorite to list 268.

Figure 23:
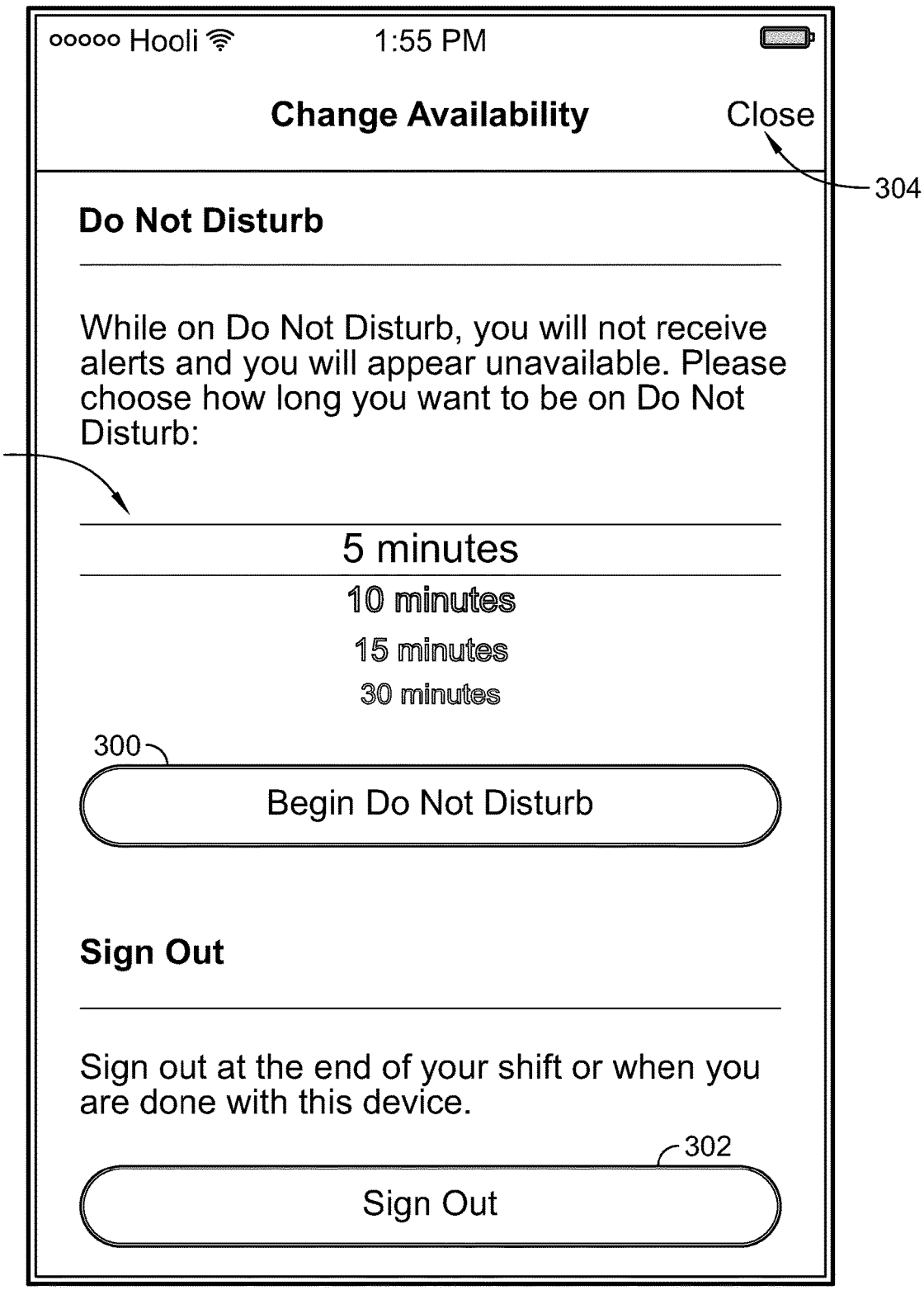
FIG. 23 is a screen shot of a first Change Availability screen that appears on the caregiver's mobile device in response to selection of a down arrow icon that appears on the screens of FIGS. 2 and 8, the first Change Availability screen permits the caregiver to select a Do Not Disturb time interval during which no new incoming alerts will be received and during which the caregiver will be designated as unavailable, the Change availability screen also having a Sign Out icon that is selected by the caregiver to sign out at the end of their shift.

Referring now to FIG. 23, a first Change Availability screen 294 appears on the caregiver's mobile device 52 in response to selection of a down arrow icon 296 that appears on the screens 100, 180 of FIGS. 2 and 8, respectively. The first Change Availability screen 294 permits the caregiver to select a Do Not Disturb time interval 298 during which no new incoming alerts will be received and during which the caregiver will be designated as unavailable. In the illustrative example, the time interval 298 can be selected by scrolling in 5 minute increments up to 15 minutes at which point the increments increase by 15 minutes each. A "Begin Do Not Disturb" button 300 is provided on screen 294 and is selected by the caregiver to activate or initiate the Do Not Disturb time interval. The Change availability screen 294 also has a Sign Out icon 302 that is selected by the caregiver to sign out at the end of their shift. After sign out, the caregiver is no longer available to receive alert messages occurring within system 50. A Close icon 304 is provided on screen 294 and is selected by the caregiver to close out of screen 294 and return to the previous screen.

Figure 24:
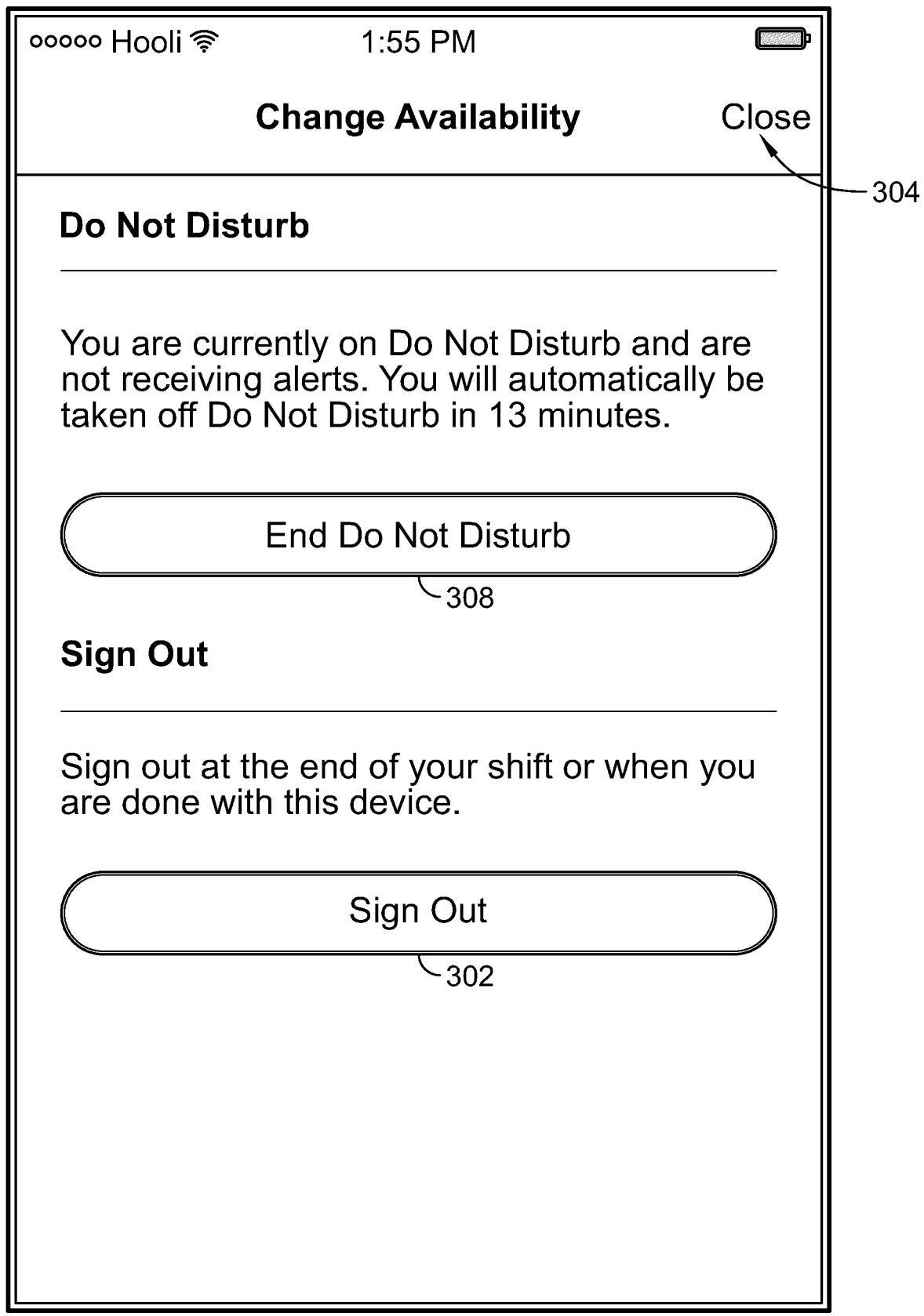
FIG. 24 is a screen shot of a second Change Availability screen that appears on the caregiver's mobile device in response to selection of a Change icon that appears on the screens of FIGS. 19 and 20 if a Do Not Disturb time interval has been previously set, the second Change Availability screen permits the caregiver to end the Do Not Disturb time interval and also has the Sign Out icon that is selected by the caregiver to sign out at the end of their shift.

Referring now to FIG. 24, a second Change Availability screen 306 appears on the caregiver's mobile device 52 in response to selection of the down arrow icon 294 on the screens 100, 180 of FIGS. 2 and 8, respectively, if a Do Not Disturb time interval 298 has been previously set and is active. The second Change Availability screen 306 has an "End Do Not Disturb" icon 308 that is selected by the caregiver to end the Do Not Disturb time interval 298. Icons 302, 304 appearing on screen 306 have been described previously and the same description applies.

Figure 25:
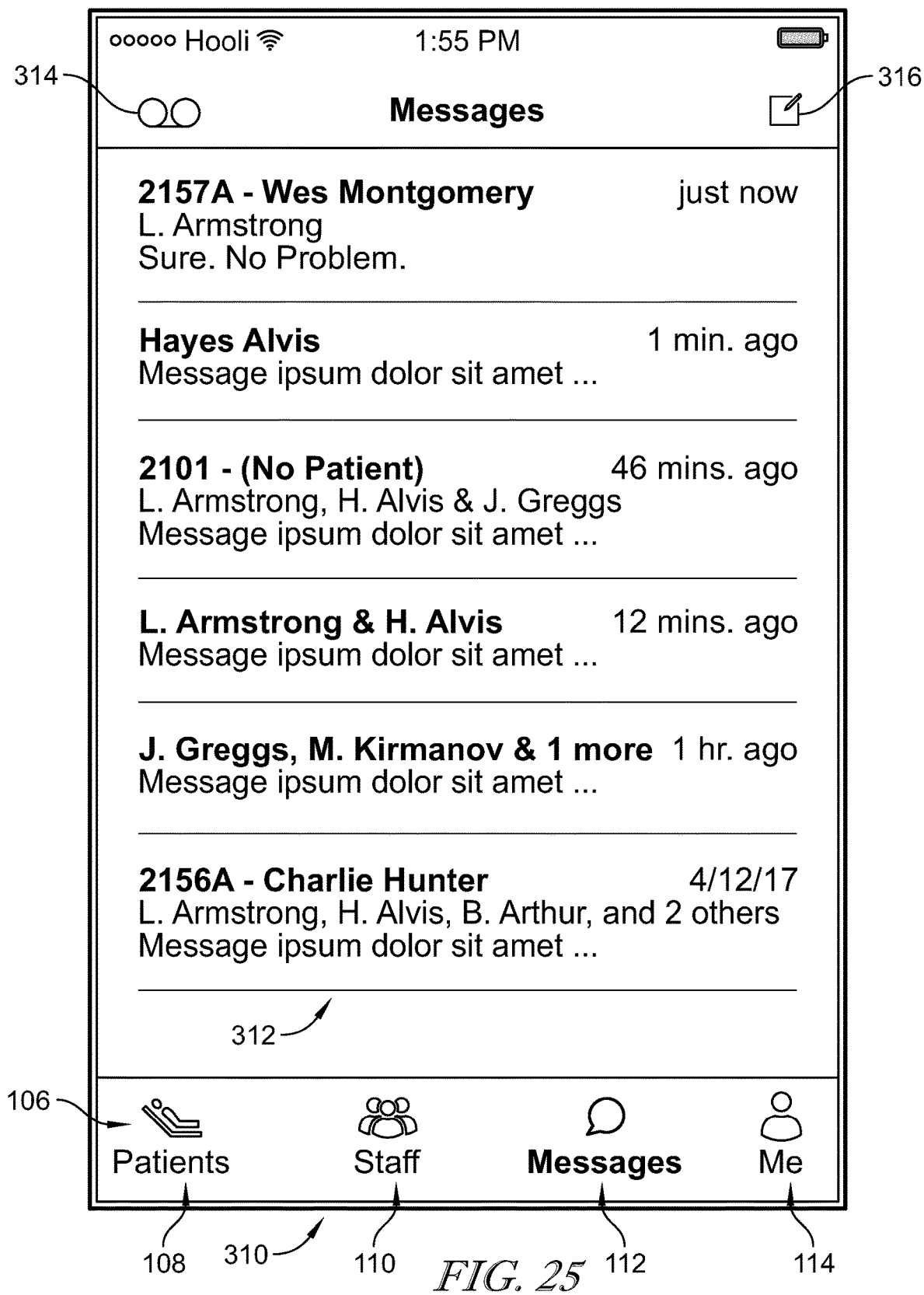
FIG. 25 is a screen shot of a Messages screen that appears on the caregiver's mobile device in response to selection of a Messages icon of the main menu shown at the bottom of the mobile device, the Message screen having a list of message strings in which the caregiver has been involved in the past.

Referring now to FIG. 25, a Messages screen 310 appears on the caregiver's mobile device 52 in response to selection of the Messages icon 112 of the main menu 106. The Message screen 310 has a list 312 of message strings in which the caregiver has been involved in the past. Some message strings are group messages sent or received to multiple caregivers and some are individual messages sent to individual caregivers. The time of the most recent message in the string is indicated at the right side of each row in list 312. Screen 312 has a New Voice Message icon 314 that the caregiver selects to send a voice message to one or more selected caregivers. Screen 312 also has a New Message icon 316 that the caregiver selects to send a text message to one or more selected caregivers.

Figure 26:
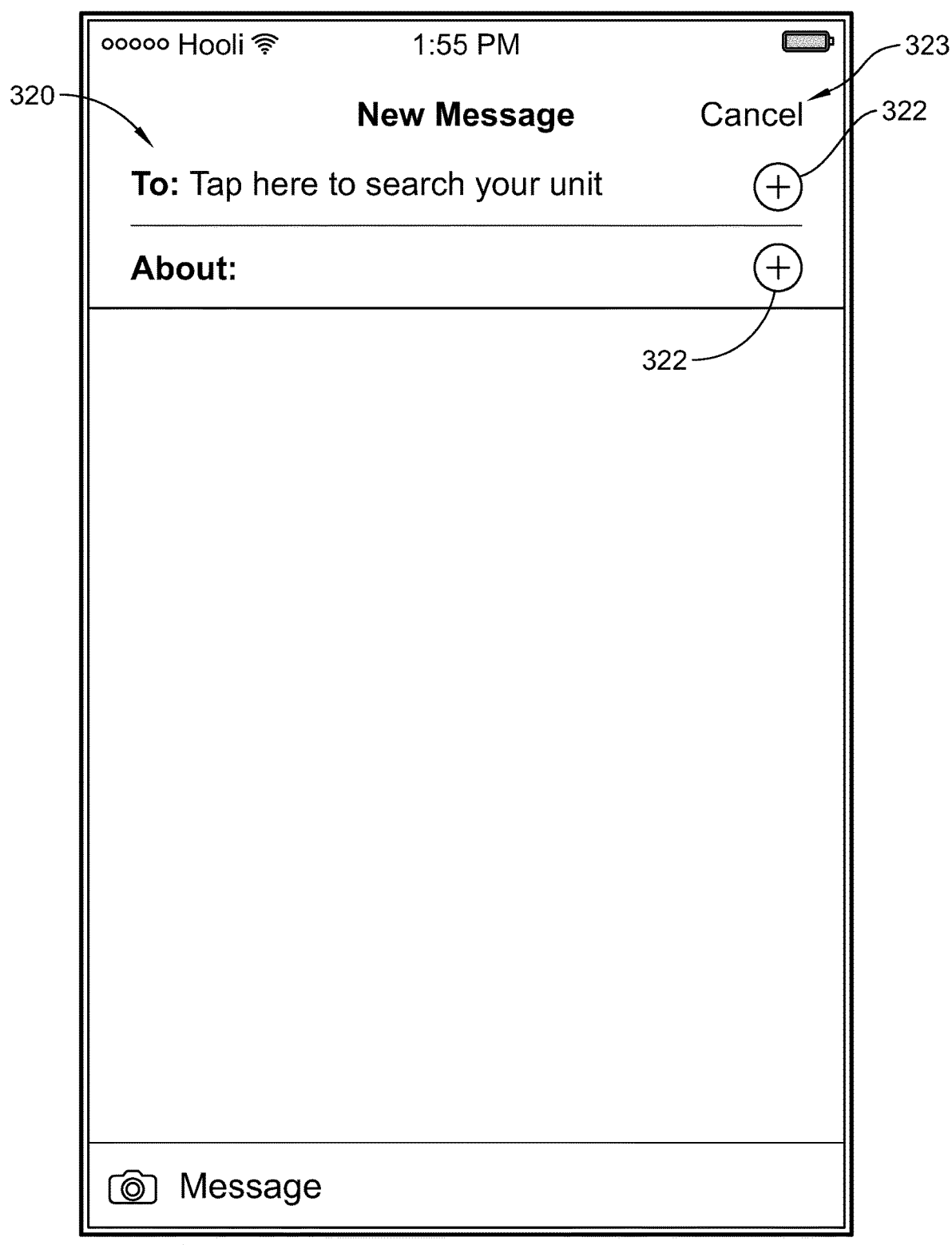
FIG. 26 is a screen shot of a New Message screen that appears on the caregiver's mobile device in response to a New Message icon being selected on the Messages screen of FIG. 25, the New Message screen having a "Tap here to search your unit" icon in the To field and having plus sign ("+") icons in the To filed and the About field.

Referring now to FIG. 26, a New Message screen 318 appears on the caregiver's mobile device 52 in response to icon 316 being selected on the Messages screen 310 of FIG. 25. The New Message screen has a "Tap here to search your unit" icon 320 in the To field. Screen 318 also has "+" icons 322 (aka Add icons 322) at the right side of each of the To fields and About fields. A Cancel icon 323 is provided on screen 318 and is selected by the caregiver to return to the previous screen.

Figure 27:
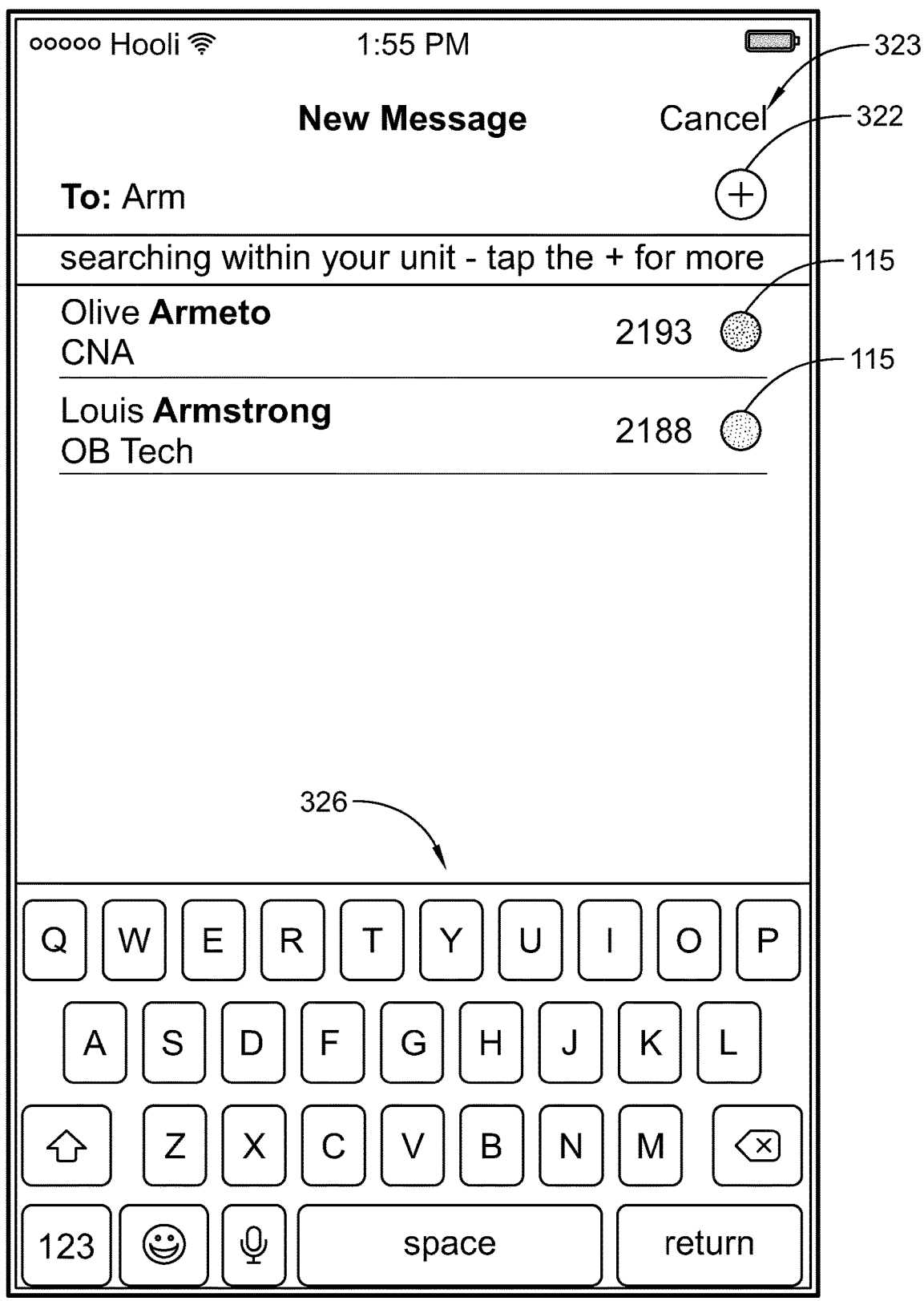
FIG. 27 is a screen shot of a first Search Results screen that appears on the caregiver's mobile device after selection of the plus sign ("+") icon in the To field of FIG. 26 and after the search string "Arm" has been entered into the search string as search criteria, the first Search Results screen listing two caregivers that met the search criteria and having a keyboard at the bottom of the screen for typing a message.

Referring now to FIG. 27, a first Search Results screen 324 appears on the caregiver's mobile device 52 after selection of the Add icon 322 in the To field of FIG. 26 and after the search string "Arm" has been entered into the To field as a search string or search criteria. The first Search Results screen 324 lists two caregivers that met the search criteria and also has a keyboard 326 at the bottom of the screen 324 for typing a message.

Figure 28:
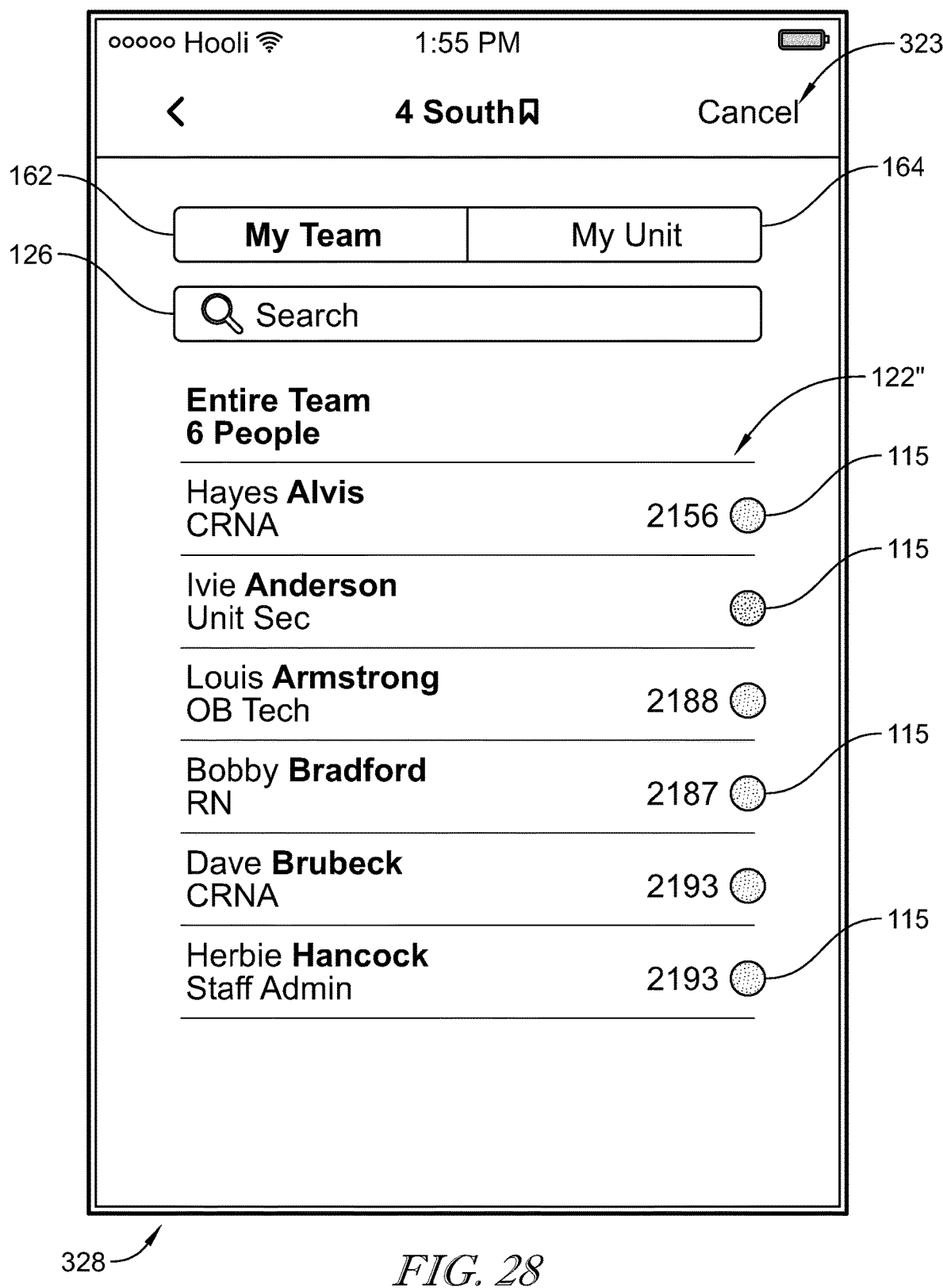
FIG. 28 is a screen shot of a My Team screen that appears on the caregiver's mobile device in response to selection of the "Tap here to search your unit" icon on the screen of FIG. 26, the My Team screen having a list of the caregiver's team members to whom messages can be sent and having a My Unit icon which can be selected to display a list of staff members in the caregiver's unit rather than the team members.

Referring now to FIG. 28, a My Team screen 328, similar to screen 160 of FIG. 6, appears on the caregiver's mobile device 52 in response to selection of the "Tap here to search your unit" icon 320 on screen 318 of FIG. 26. Icons 115, 126, 162, 164, 323 of screen 328 have been described above and the same description is applicable to screen 328. In the illustrative example of FIG. 28, icon 162 is highlighted and so the My Team screen 328 has a list 122" of the caregiver's team members to whom messages can be sent. Selection of icon 164 results in a list of staff members in the caregiver's unit being displayed in list 122" rather than the team members. Selection of staff members names on list 122" results in the names being added to the To field of screen 318 of FIG. 26.

Figure 29:
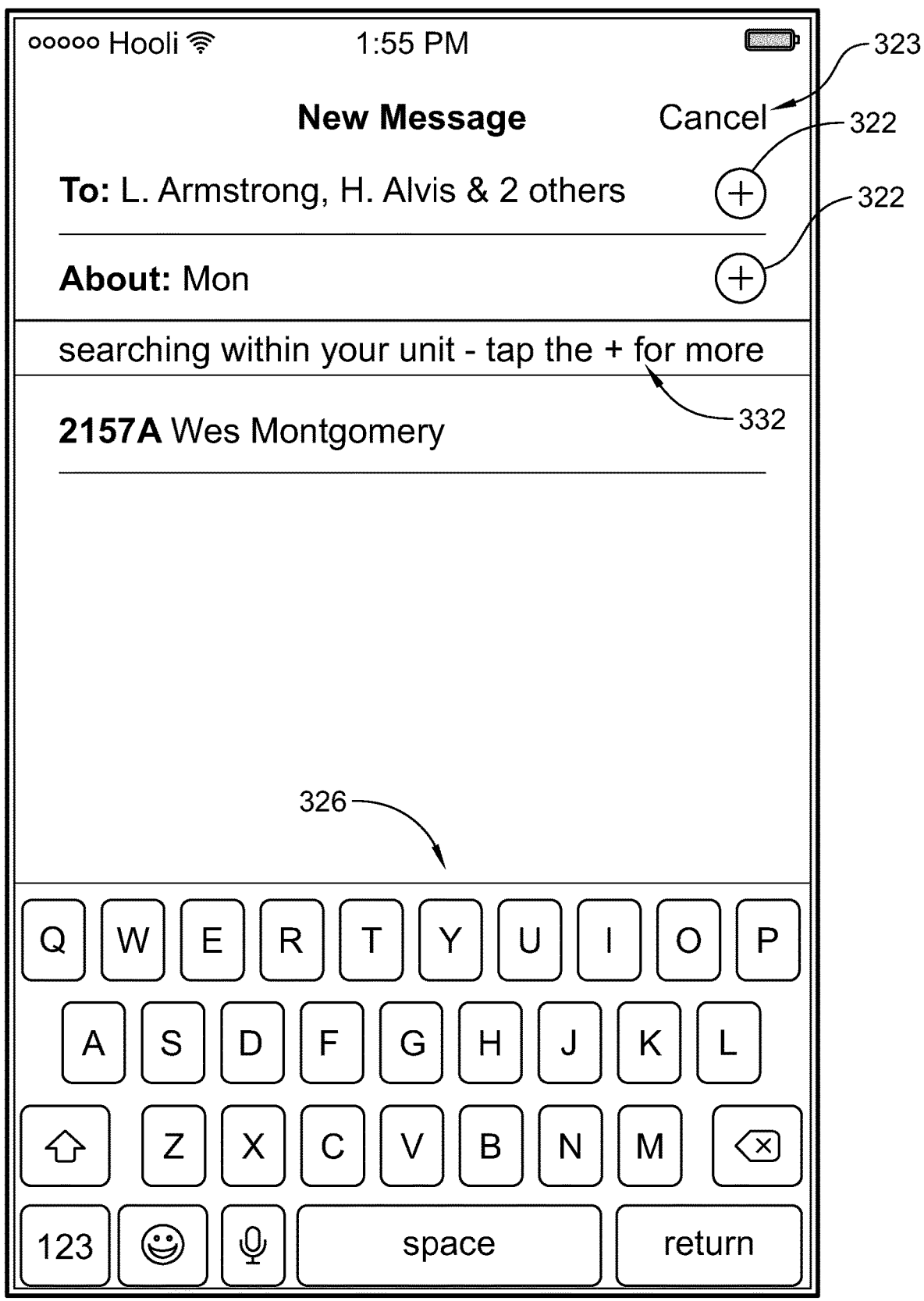
FIG. 29 is a screen shot of a second Search Results screen that appears on the caregiver's mobile device after selection of the plus sign ("+") icon in the About field of FIG. 26 and after the search string "Mon" has been entered into About field as search criteria, the second Search Results screen listing one patient that met the search criteria and having a keyboard at the bottom of the screen for typing a message.

Referring now to FIG. 29, a second Search Results screen 330 appears on the caregiver's mobile device 52 after selection of the Add icon in the About field of FIG. 26 and after the search string "Mon" has been entered into About field as a search criteria. The second Search Results screen 330 lists one patient that met the search criteria and has the keyboard at the bottom of the screen 330 for typing a message. In FIG. 29, a "searching within your unit—tap the + for more" message 332 appears beneath the About field.

Figure 30:
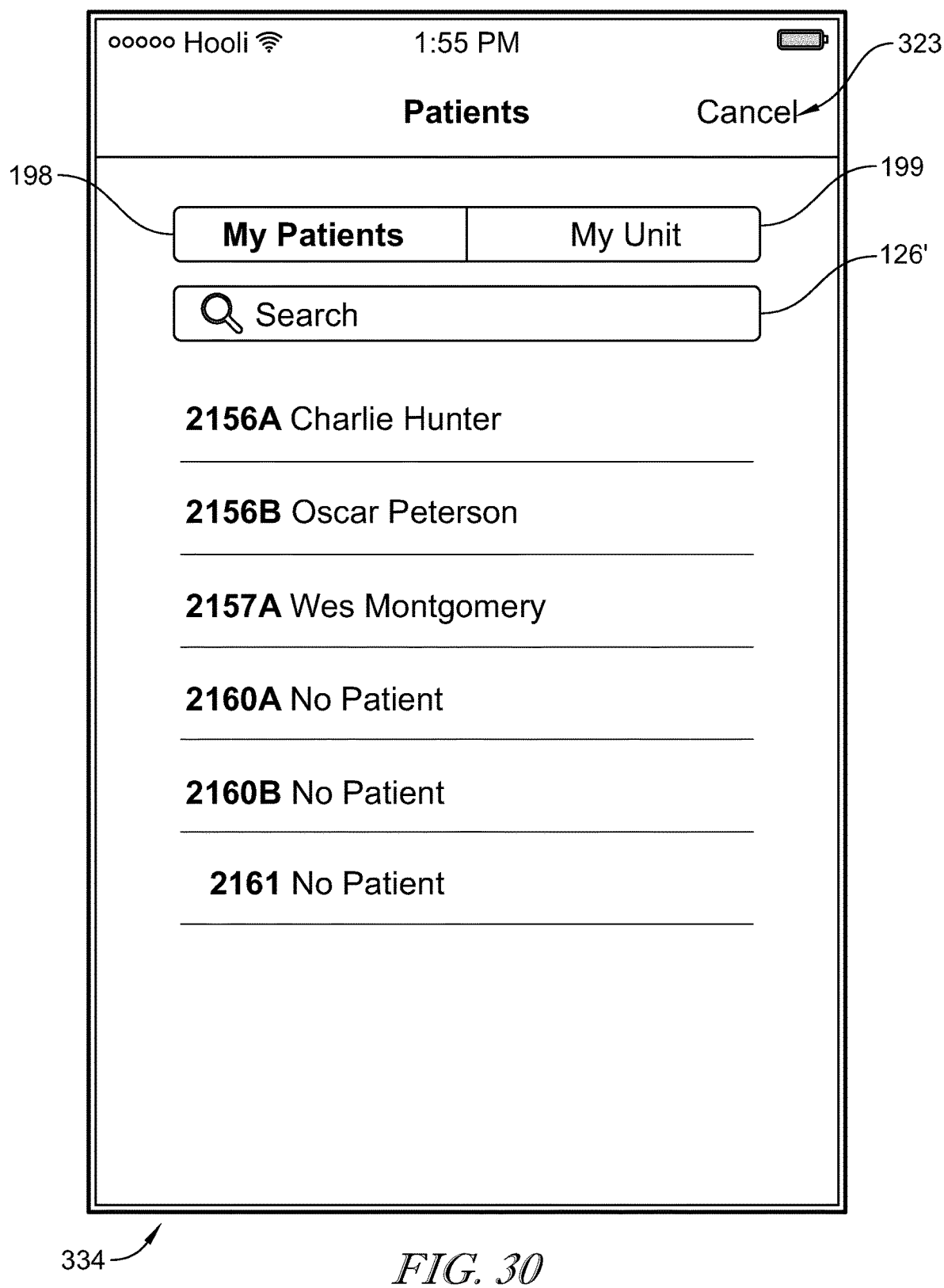
FIG. 30 is a screen shot of a My Patients screen that appears on the caregiver's mobile device in response to selection of a plus sign ("+") icon on the screen of FIG. 29 in the About field, the My Patients screen having a list of the patients assigned to the caregiver to whom messages can be sent and having a My Unit icon which can be selected to display a list of patients in the caregiver's unit rather than just the caregiver's assigned patients.

Referring now to FIG. 30, a My Patients screen 334 appears on the caregiver's mobile device 52 in response to selection of a Add icon 322 on the screen 330 of FIG. 29 in the About field. Icons 198, 199, 323 of screen 334 have been described above and the same description is applicable to screen 334. Icon 126' is similar to icons 126 of FIGS. 3, 6, 9 and 28 except that patients are searched in connection with icon 126' rather than staff members. In the illustrative example of FIG. 30, icon 198 is highlighted and so the My Patients screen 334 has a list of the patients assigned to the caregiver to whom messages can be sent. Selection of icon 199 on screen 334 results in a list of patients from the caregiver's unit being displayed rather than just the patients assigned to the caregiver.

Figure 31:
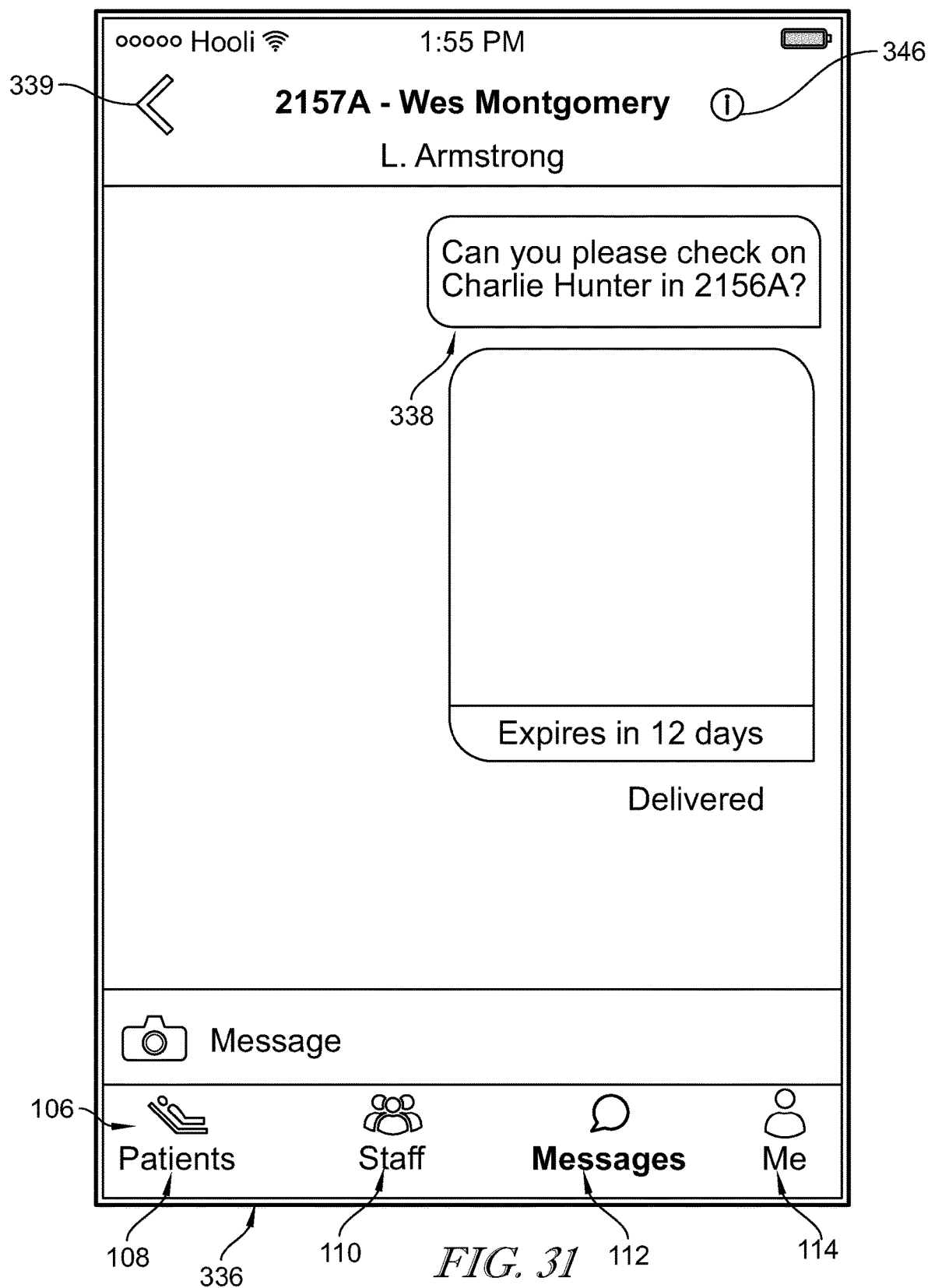
FIG. 31 is a screen shot of a Sent Message screen showing an example of a message that has been sent by the caregiver using their mobile device.
Figure 32:
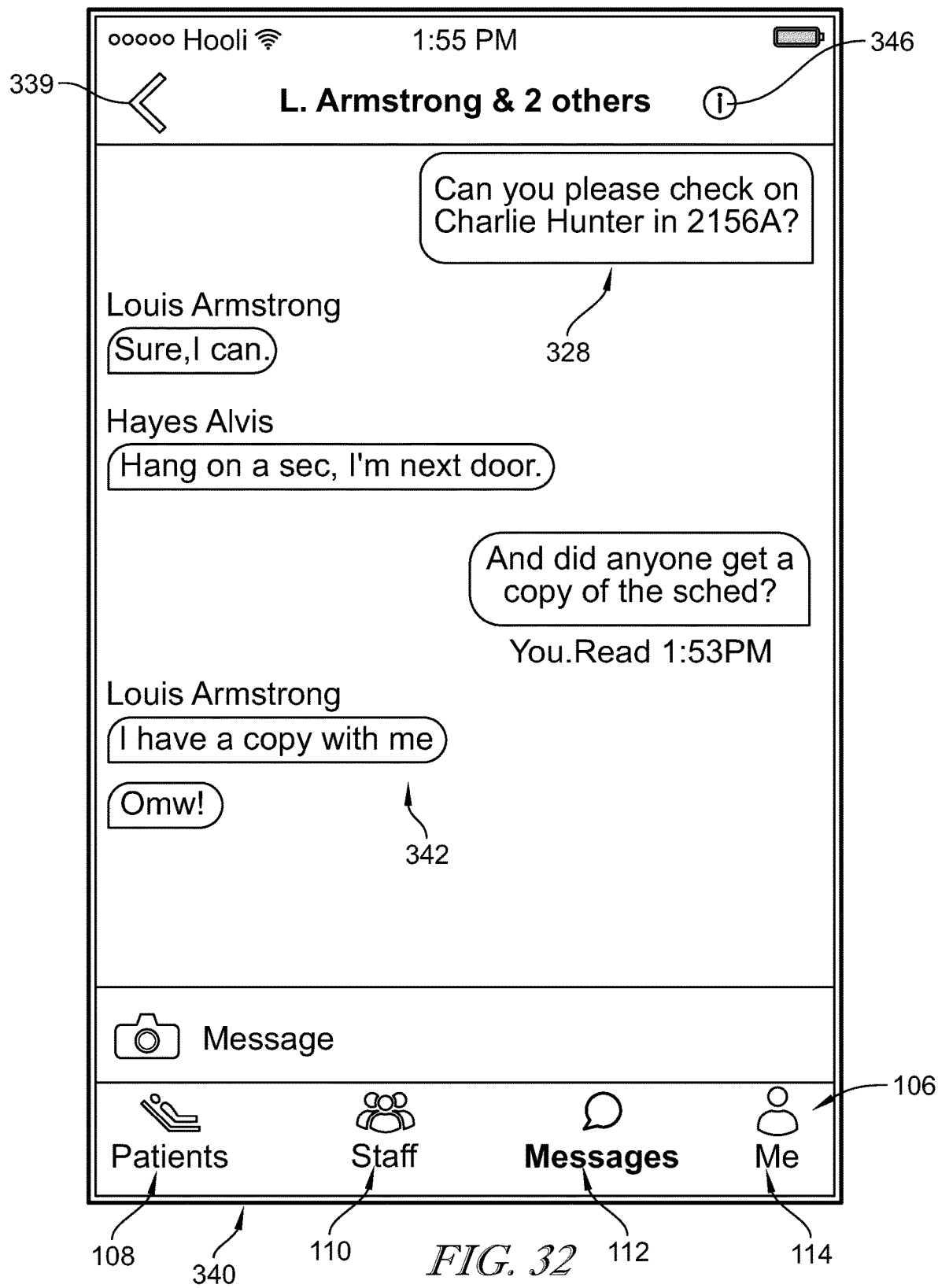
FIG. 32 is a screen shot of a Message String screen showing examples of a message string between the caregiver and two other caregivers.

Referring now to FIG. 31, a Sent Message screen 336 shows an example of a message 338 that has been sent by the caregiver using the caregiver's mobile device 52. A back arrow 339 appears at the top left of screen 336 and is selected by the caregiver to return back to screen 310 of FIG. 25 or to some other default screen. Referring to FIG. 32, a Message String screen 340 shows an example of a message string 342 between the caregiver and two other caregivers. The two other caregivers are Louis Armstrong and Hayes Alvis in the given example.

Figure 33:
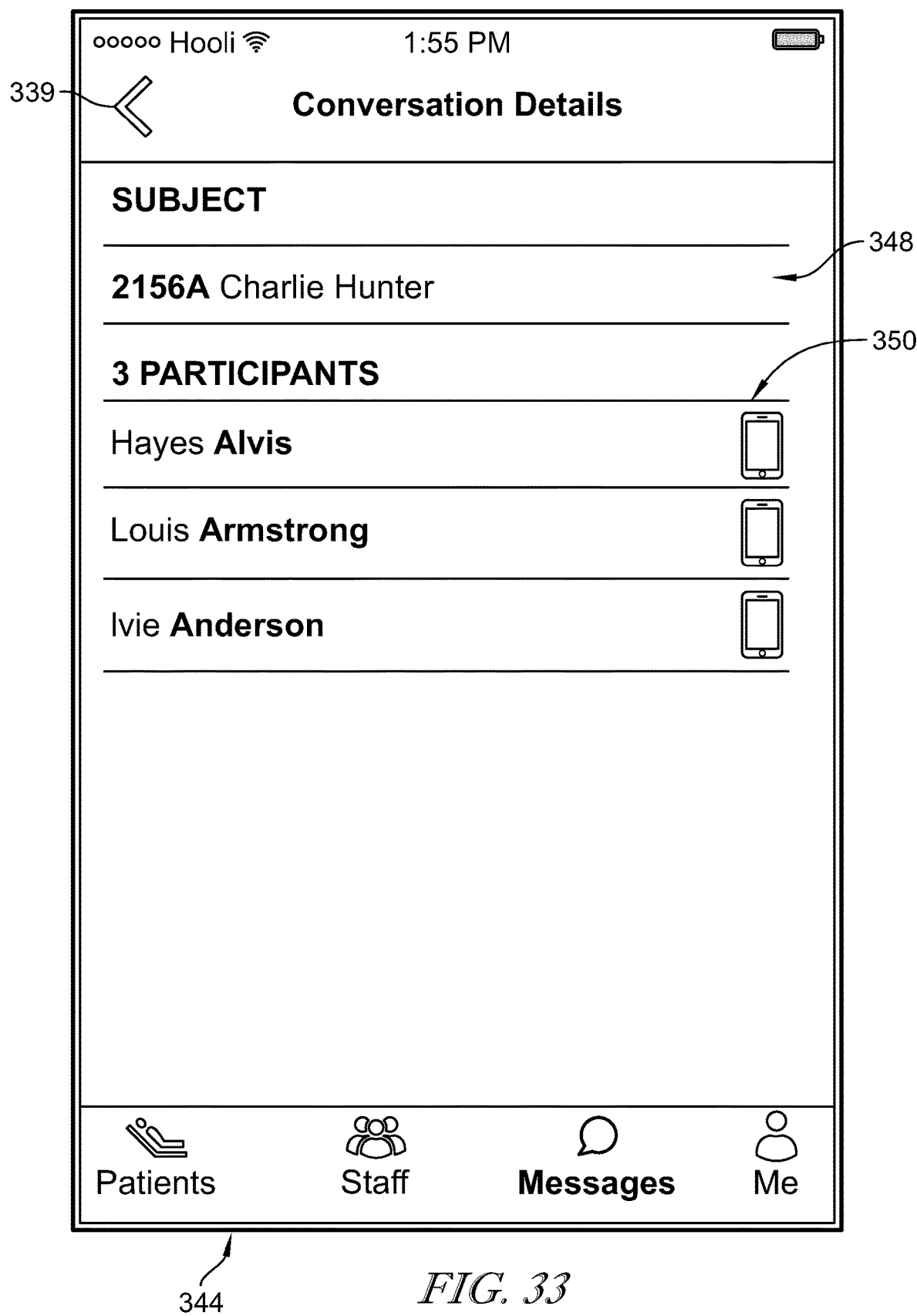
FIG. 33 is a screen shot of a Conversation Details screen that appears on the caregiver's mobile device in response to an information ("i") icon being selected on the screen of FIG. 32 showing a list of participants to the message string of FIG. 32.

Referring now to FIG. 33, a Conversation Details screen 344 appears on the caregiver's mobile device 52 in response to an information ("i") icon 346 being selected on the screen 340 of FIG. 32. Screen 344 has a field 348 showing the subject of the conversation (Charlie Hunter of room 2156A in the given example) and showing a list 350 of participants to the message string 342 of FIG. 32. Icon 339 also appears on screen 344 and is selectable to return back to the screen 340 of FIG. 32.

Figure 34:
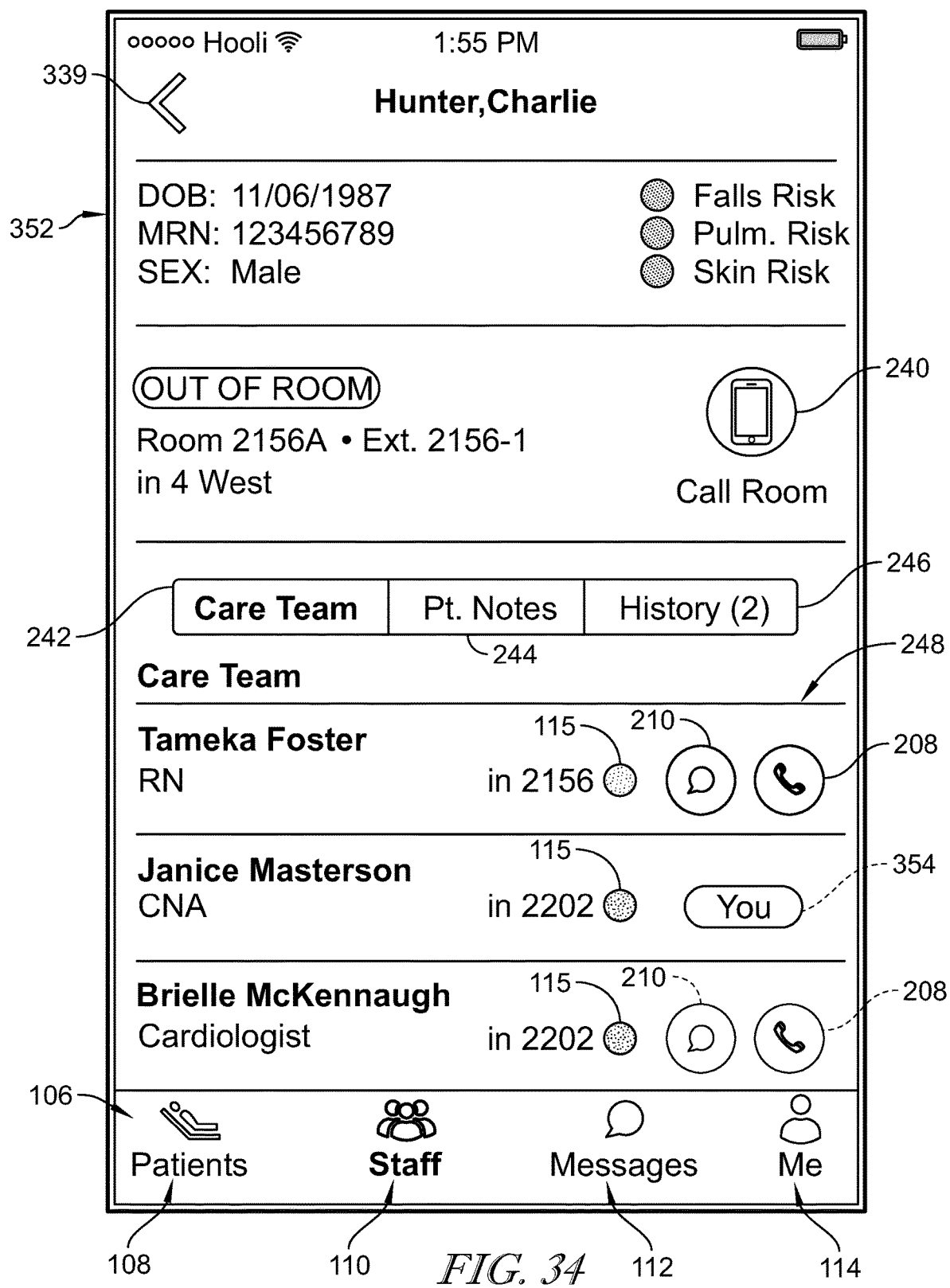
FIG. 34 is a screen shot, similar to FIG. 17, of a Care Team screen that appears on a caregiver's phone who does not have administrative rights to set states for the respective patient, the Care Team screen including an upper section having information indicating the patient's location, date of birth, sex, and medical risks, and having a Call Room icon that permits the caregiver to call into the patient's room and the Care Team screen having a bottom section including a Care Team list and icons for messaging or calling members of the listed care team.

Referring now to FIG. 34, a Care Team screen 352, similar to screen 232 of FIG. 17, appears on a caregiver's phone 52 for a caregiver (Janice Masterson in the given example) who does not have administrative rights to set states for the respective patient. The same reference numbers are used in FIG. 34 for those portions of screen 352 that are the same as or substantially similar to like portions of screen 232 of FIG. 17 and the descriptions above are equally applicable. In FIG. 34, icons 234, 236, 238 are omitted because these functions are not available to particular staff member. Also, a You indicia 354 appears in list 248 next to the caregiver's name.

Figure 35:
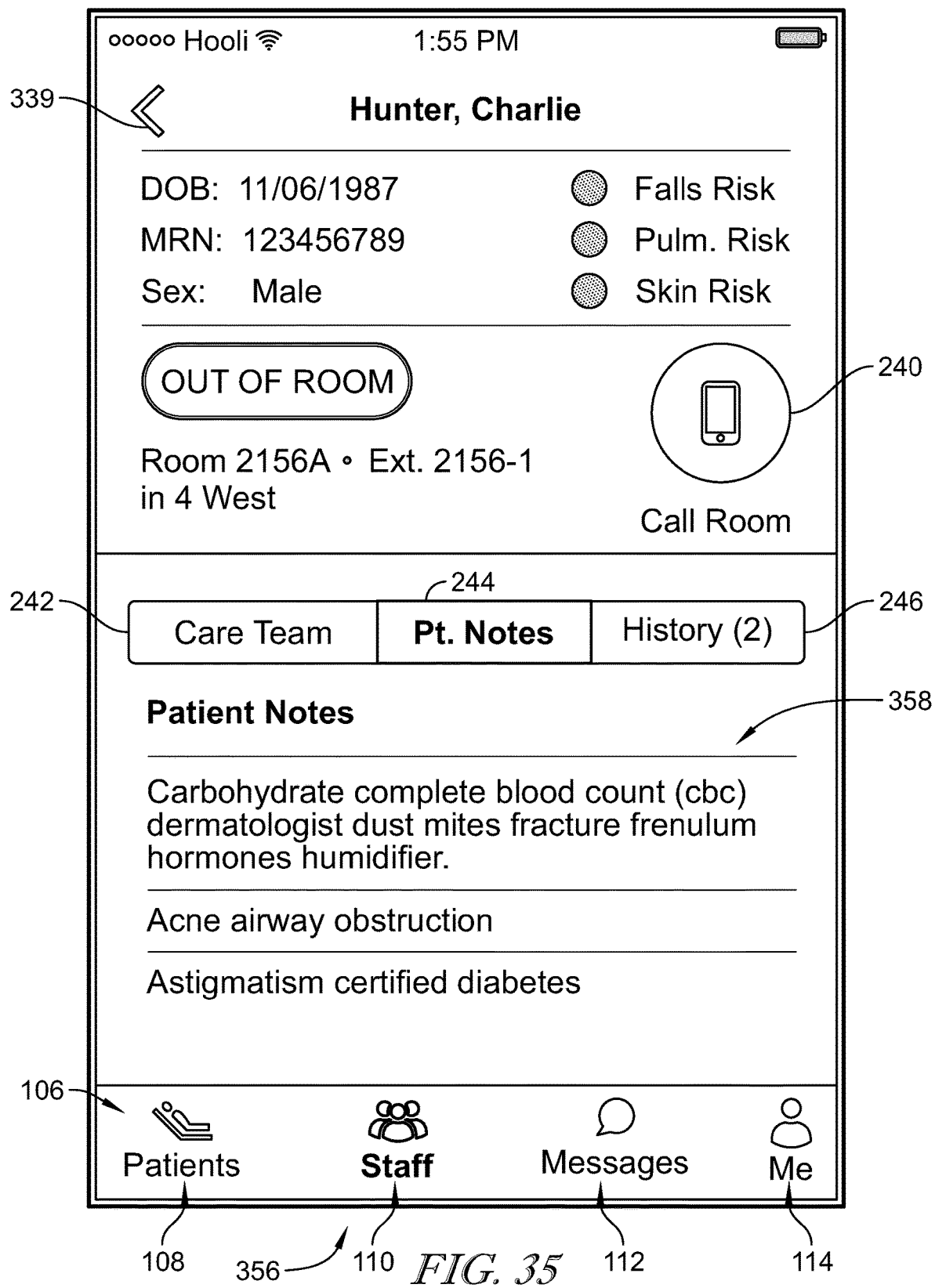
FIG. 35 is a Patient Notes screen that appears on the caregiver's mobile device in response to selection of a Pt. Notes icon on the screen of FIG. 34, the Patient Notes screen having caregiver's notes about the patient in the bottom section.

Referring now to FIG. 35, a Patient Notes screen 356 appears on the caregiver's mobile device 52 in response to selection of the Pt. Notes icon 244 on the screen 352 of FIG. 34. The Patient Notes screen 356 has a window 358 in the bottom section beneath icons 242, 244, 246 that contains notes that have been entered by one or more caregivers about the patient using their mobile devices 52 or other equipment (e.g., nurse call computers, EMR computers, ADT computers) of system 50.

Figure 36:
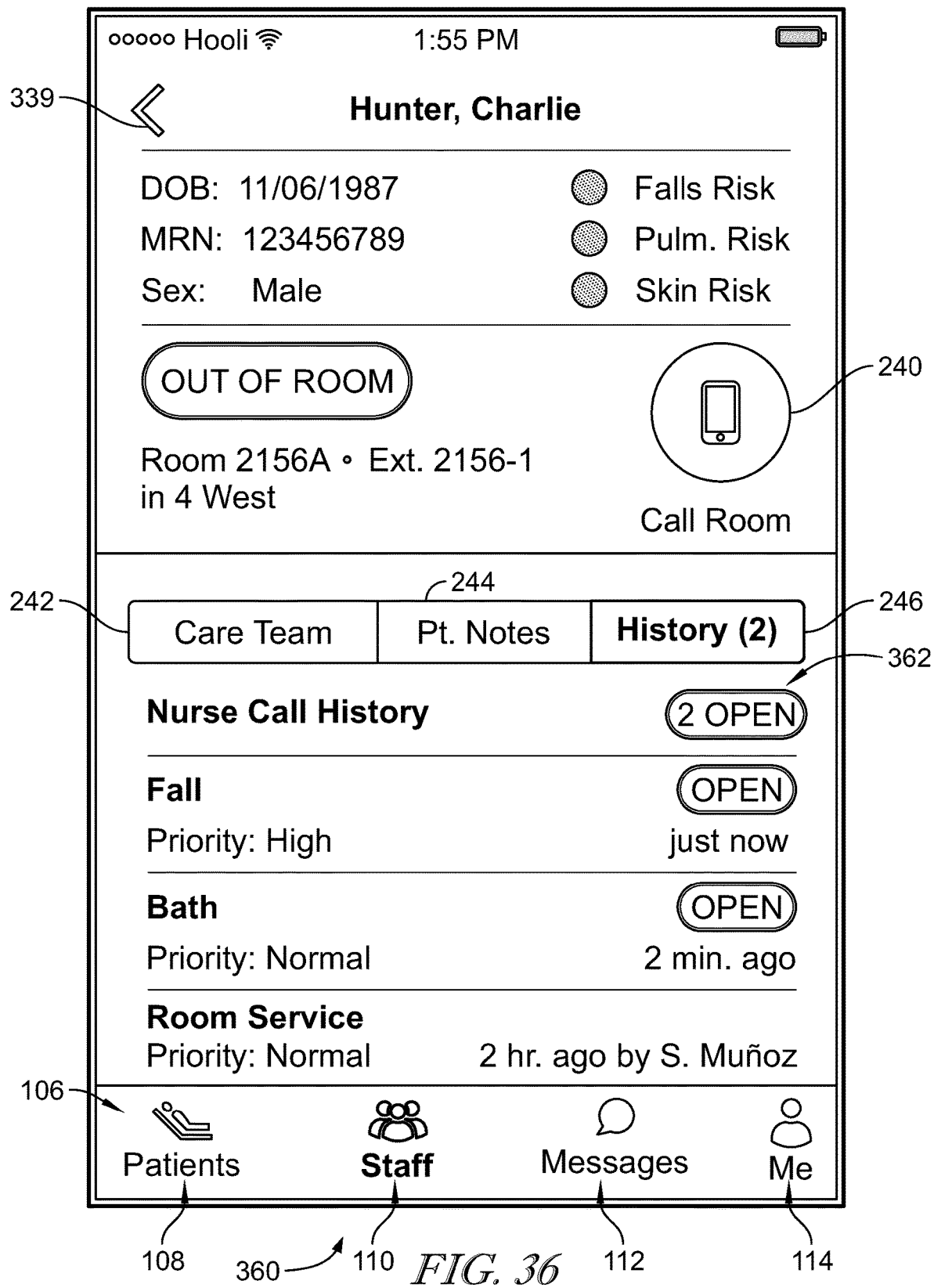
FIG. 36 is a History screen that appears on the caregiver's mobile device in response to selection of a History icon on the screen of FIG. 34 or FIG. 35, the History screen having a history of the patient's nurse calls in the bottom section, including nurse calls that are still open.

Referring now to FIG. 36, a History screen 360 appears on the caregiver's mobile device 52 in response to selection of the History icon 246 on screen 352 of FIG. 34 or screen 356 of FIG. 35. The History screen 360 has a history window 362 in the bottom section beneath icons 242, 244, 246 that contains a list of the patient's nurse calls including currently open nurse calls and older nurse calls that have been previously completed by caregivers.

Figure 37:
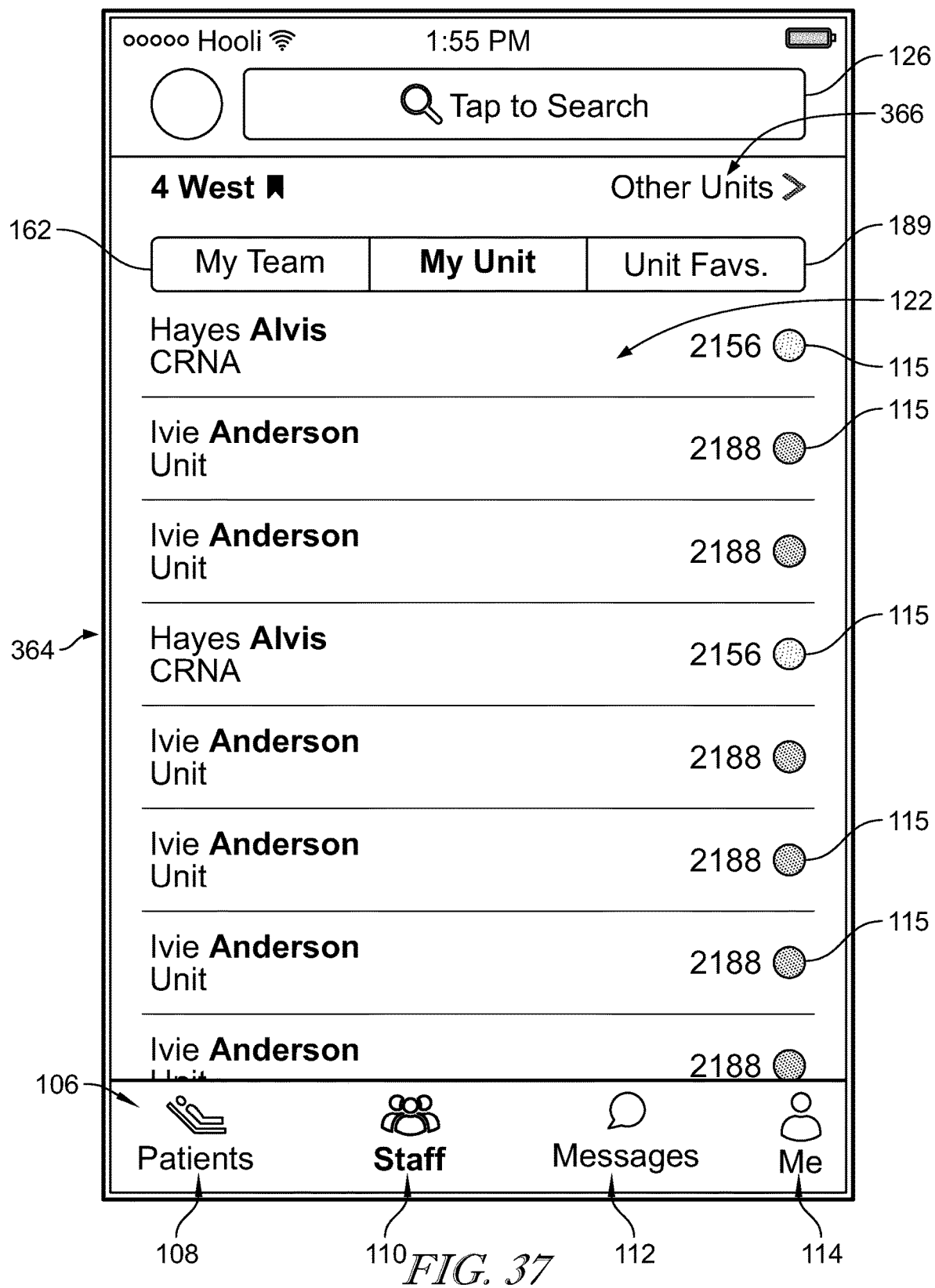
FIG. 37 is a screen shot, similar to FIG. 9, of an alternative My Unit screen showing a list of staff assigned to the same unit as the caregiver.
Figure 38:
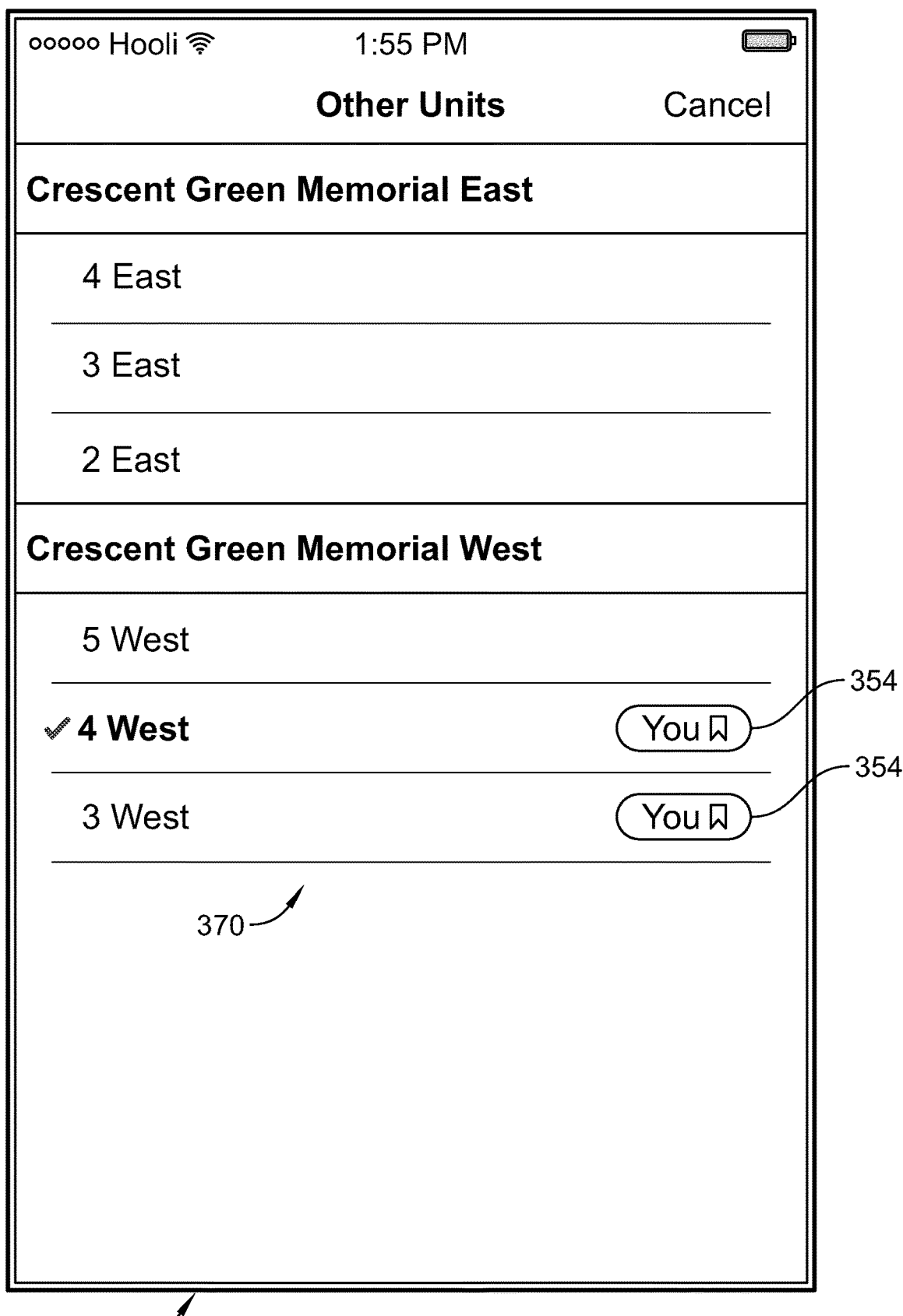
FIG. 38 is a screen shot of an Other Units screen that appears on the caregiver's mobile device in response to selection of an Other Units icon on the screen of FIG. 37, the Other Units screen having a list of other units of first and second hospital campuses.

Referring now to FIG. 37, an alternative My Unit screen 364, similar to FIG. 9, is shown with list 122 displaying a portion of staff assigned to the same unit as the caregiver. Scrolling is needed on screen 364 to see other staff of the unit. The same reference numbers are used in FIG. 37 as were used in FIG. 9 and the descriptions above are equally applicable. Screen 364 includes an Other Units icon 366 which is selectable by the caregiver to navigate to staff lists for other units of the healthcare facility. For example, FIG. 38 shows an Other Units screen 368 that appears on the caregiver's mobile device 52 in response to selection of the Other Units icon 366 of screen 364 of FIG. 37. The Other Units screen 368 has a list 370 of other units of first and second hospital campuses (Crescent Green Memorial East and Crescent Green Memorial West in the given example). Screen 368 also includes the You indicia 354 to indicate the units to which the caregiver belongs.

Figure 39:
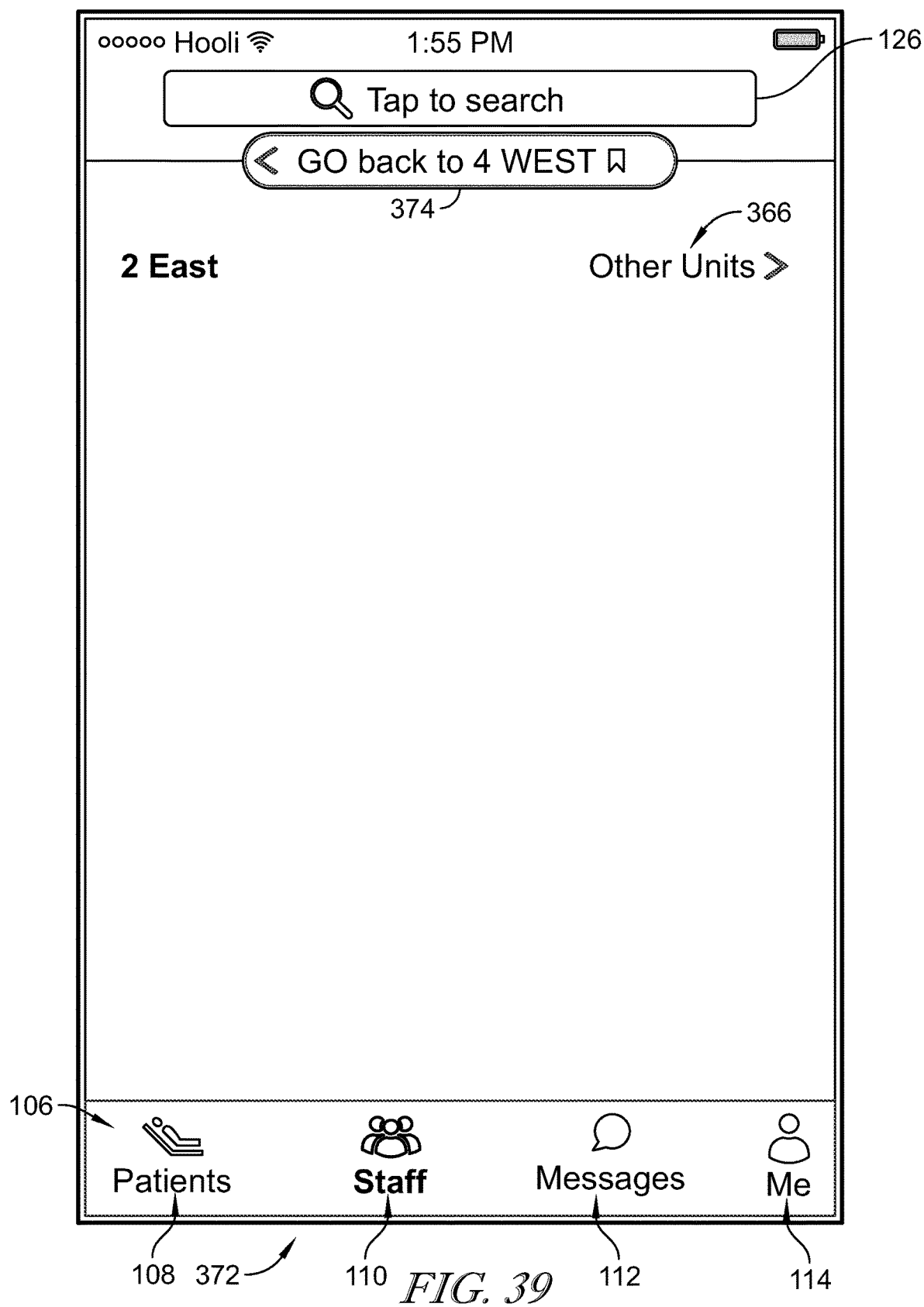
FIG. 39 is a screen shot of a Non-Home Results screen that appears on the caregiver's mobile device in response to selection of a unit from a hospital campus different than the caregiver's campus on the Other Units screen of FIG. 38.
Figure 40:
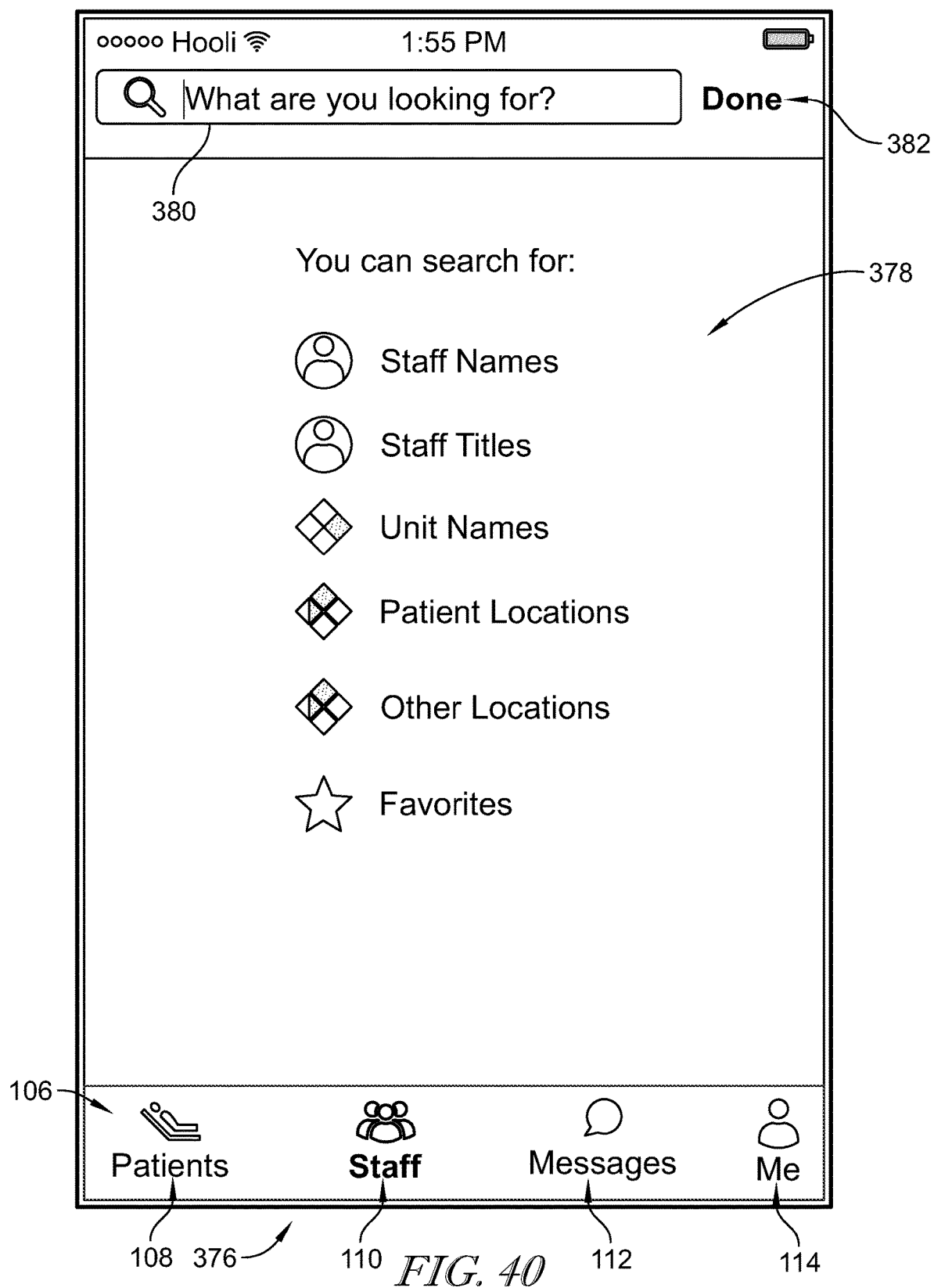
FIG. 40 is a screen shot of a Tapped Search screen that appears on the caregiver's mobile device in response to selection of a "Tap to search" icon at the top of the screens of FIG. 37 or FIG. 39, the Tapped Search screen having a list of different types of staff searches that can be undertaken by the caregiver.

Referring now to FIG. 39, a Non-Home Results screen 372 that appears on the caregiver's mobile device 52 in response to selection of a unit from a hospital campus different than the caregiver's campus on the Other Units screen 368 of FIG. 38. Screen 372 includes a "Go back to 4 West" button 374 that is selected by the caregiver to return to screen 364 of FIG. 37. FIG. 40 shows a Tapped Search screen 376 that appears on the caregiver's mobile device 52 in response to selection of the "Tap to search" icon 126 at the top of the screens 364, 372 of FIG. 37 or FIG. 39, respectively. The Tapped Search screen 376 has a list or menu 378 of different types of staff searches that can be undertaken by the caregiver. The choices in menu 378 are self-explanatory in FIG. 40. Screen 376 also has a "What are you looking for?" field 380 in which search strings are enterable by the caregiver. A Done icon 382 is also provided at the top of screen 376 for selection by the caregiver to close out of screen 376.

Figure 41:
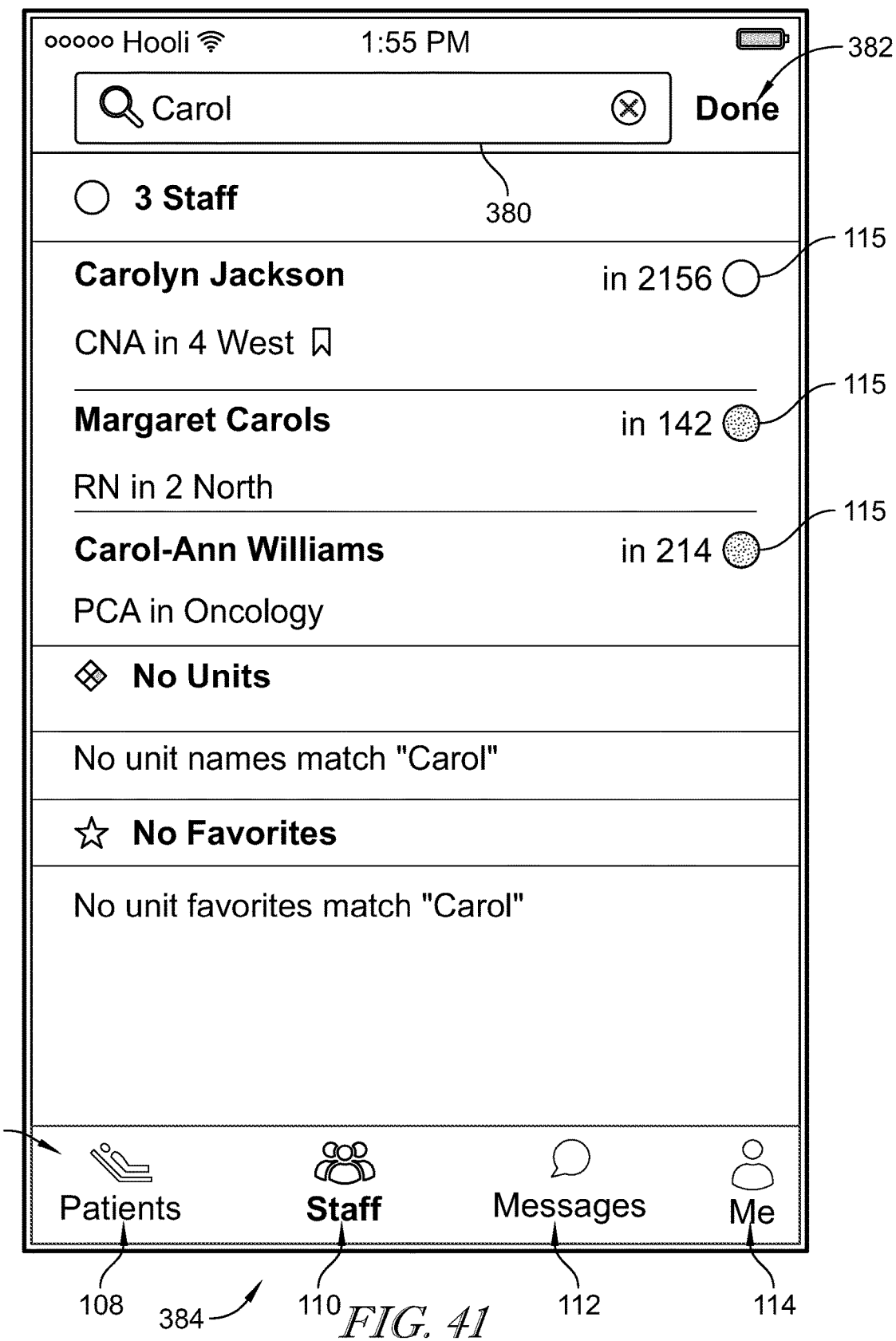
FIG. 41 is a screen shot of a first Search Results page that appears on the caregiver's mobile device in response to a search string "Carol" being entered in a "What are you looking for?" field at the top of the Tapped Search screen of FIG. 40.
Figure 42:
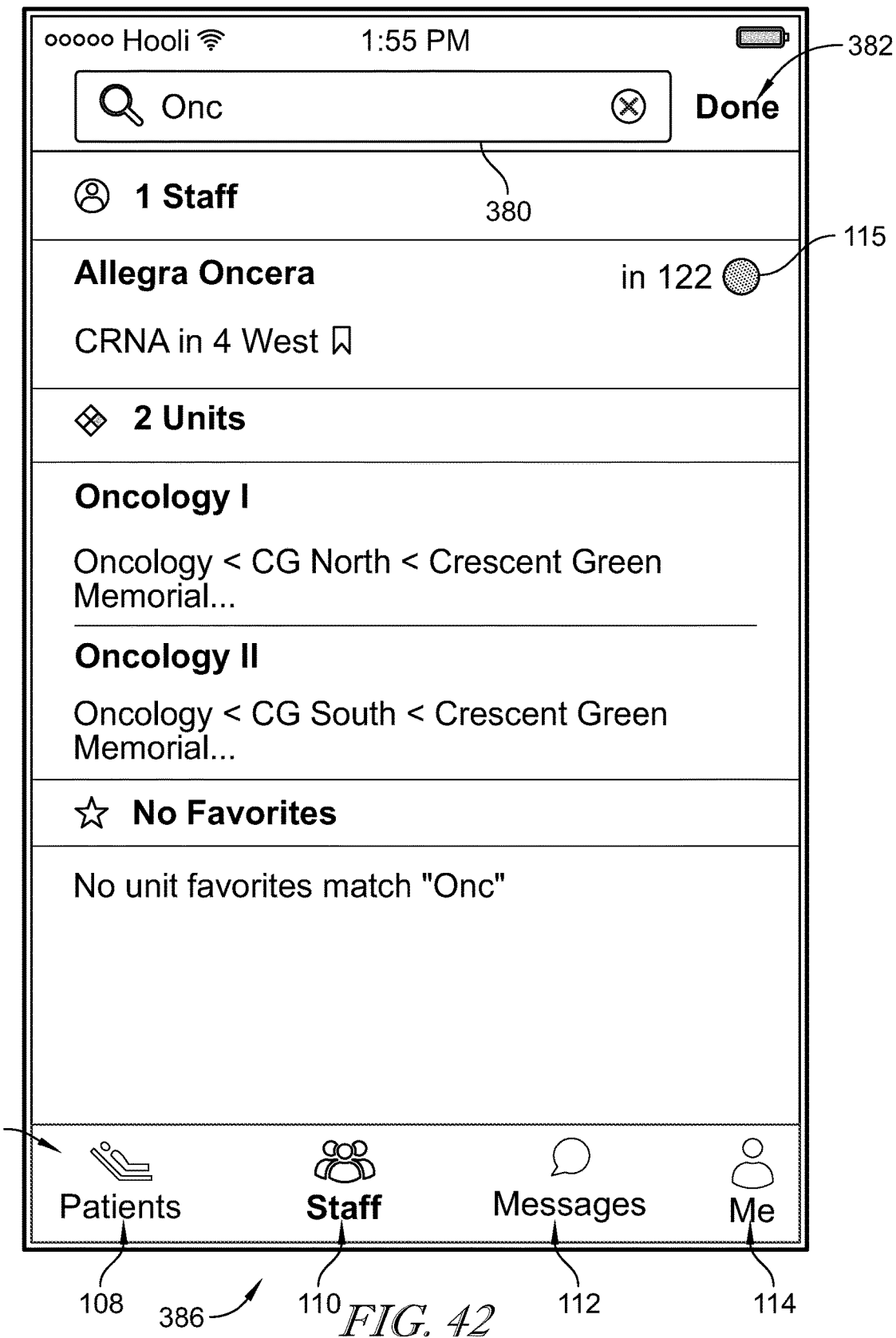
FIG. 42 is a screen shot of a second Search Results page that appears on the caregiver's mobile device in response to a search string "Onc" being entered in the "What are you looking for?" field at the top of the Tapped Search screen of FIG. 40.
Figure 43:
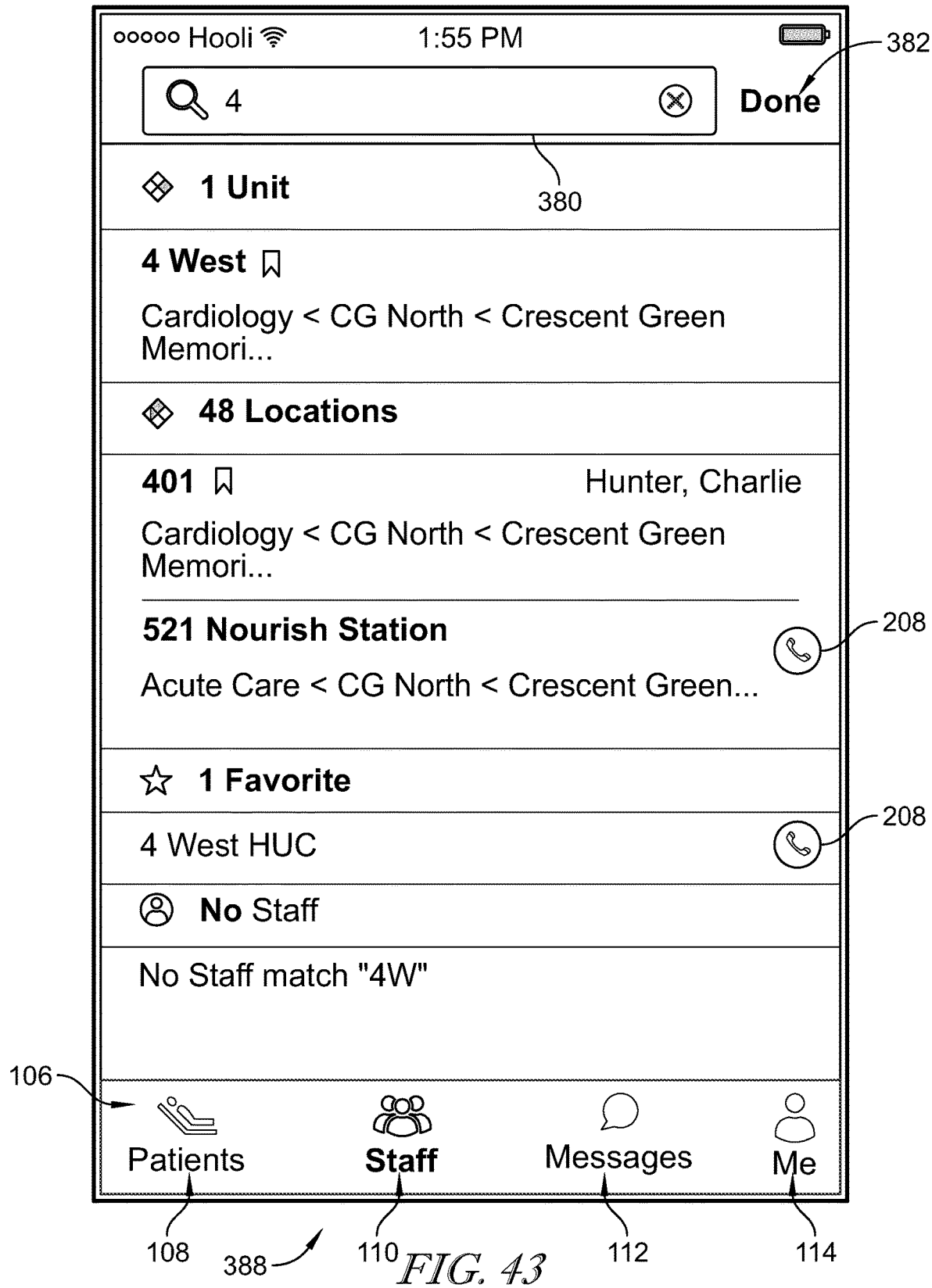
FIG. 43 is a screen shot of a third Search Results page that appears on the caregiver's mobile device in response to a search string "4" being entered in the "What are you looking for?" field at the top of the Tapped Search screen of FIG. 40.
Figure 44:
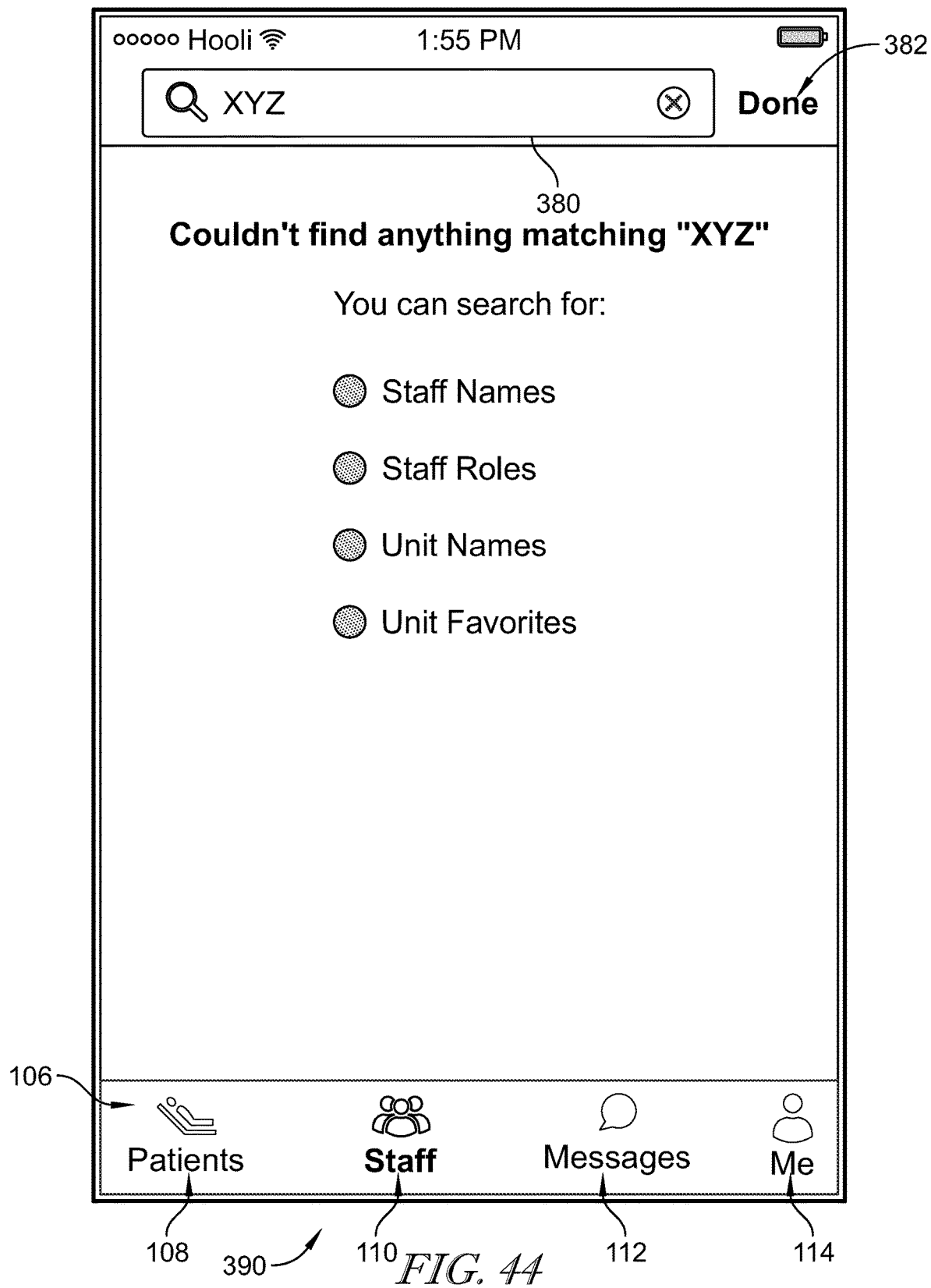
FIG. 44 is a screen shot of a fourth Search Results page that appears on the caregiver's mobile device in response to a search string "XYZ" being entered in the "What are you looking for?" field at the top of the Tapped Search screen of FIG. 40.

Referring now to FIG. 41, a first Search Results page 384 appears on the caregiver's mobile device in response to a search string "Carol" being entered in the "What are you looking for?" field 380 at the top of the Tapped Search screen 376 of FIG. 40. The search results of screen 384 include three staff members, no units, and no favorites. FIG. 42 shows a second Search Results page 386 that appears on the caregiver's mobile device 52 in response to a search string "Onc" being entered in the "What are you looking for?" field 380 at the top of the Tapped Search screen 376 of FIG. 40. The search results of screen 386 include one staff member, two units, and no favorites. FIG. 43 shows a third Search Results page 388 that appears on the caregiver's mobile device 52 in response to a search string "4" being entered in the "What are you looking for?" field 380 at the top of the Tapped Search screen 376 of FIG. 40. The search results of screen 388 include one unit, 48 locations, one favorite, and no staff. FIG. 44 shows a fourth Search Results page 390 that appears on the caregiver's mobile device 52 in response to a search string "XYZ" being entered in the "What are you looking for?" field 380 at the top of the Tapped Search screen 376 of FIG. 40. There were no matches for the search string "XYZ" as indicated on screen 390.

Figure 45:
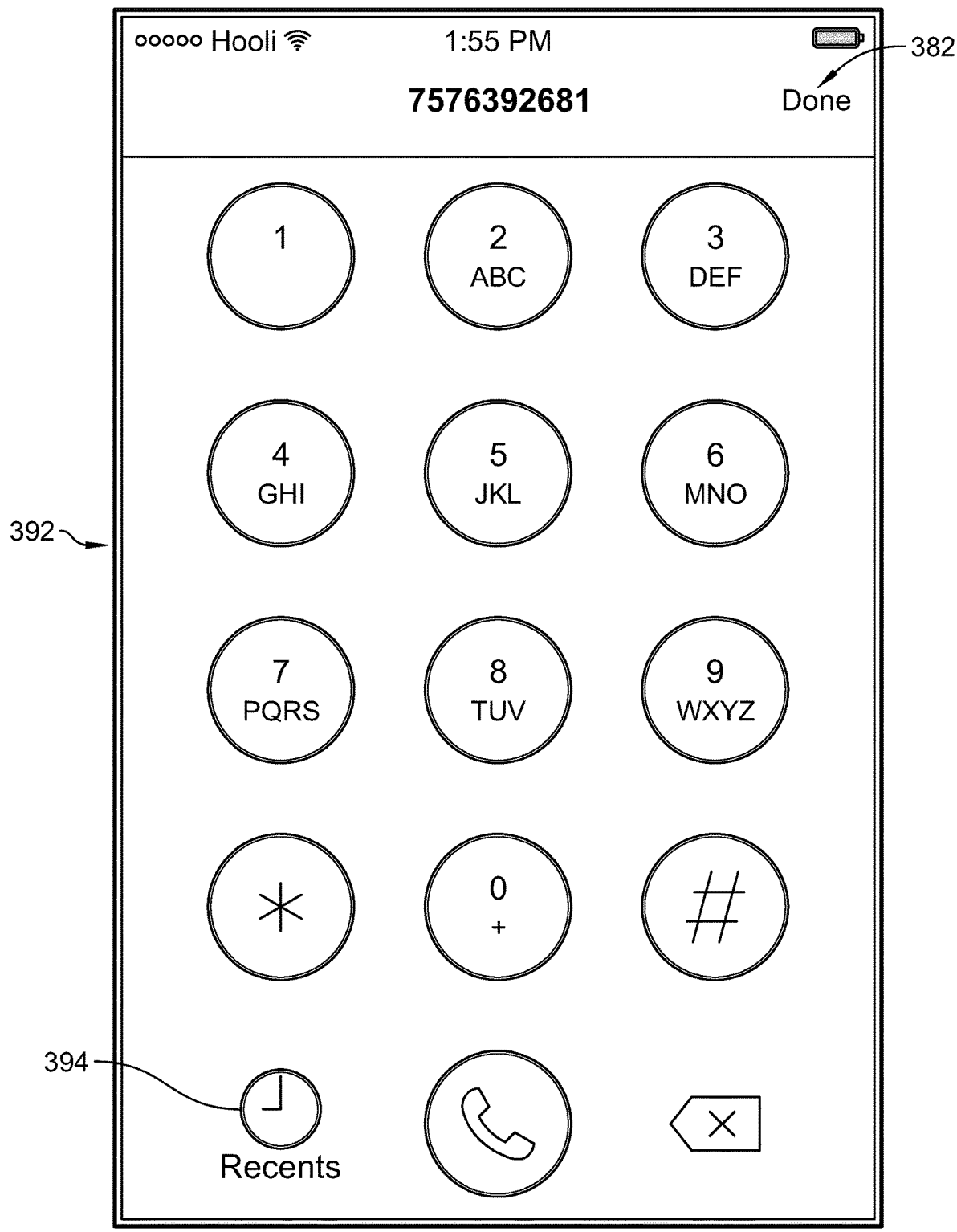
FIG. 45 is a screen shot of a Dial Pad screen that appears on the caregiver's mobile device in response to selection of a Mobile icon, shown in FIG. 7, or a phone icon such as those shown in FIGS. 13, 17, 20, 34 and 43.

Referring now to FIG. 45, a screen shot of a Dial Pad screen 392 appears on the caregiver's mobile device 52 in response to selection of the Mobile icon 176 of FIG. 7 and, in some embodiments, in response to selection of the phone icon 208 such as those shown in FIGS. 13, 17, 20, 34 and 43, for example, if an extension to another mobile device 52 or to one of audio stations 62, 64, as the case may be, is nonexistent or otherwise not available for the associated staff member or patient. Dial Pad screen 392 has a telephone dial pad that is used to place a call to a phone number as is well-known.

Figure 46:
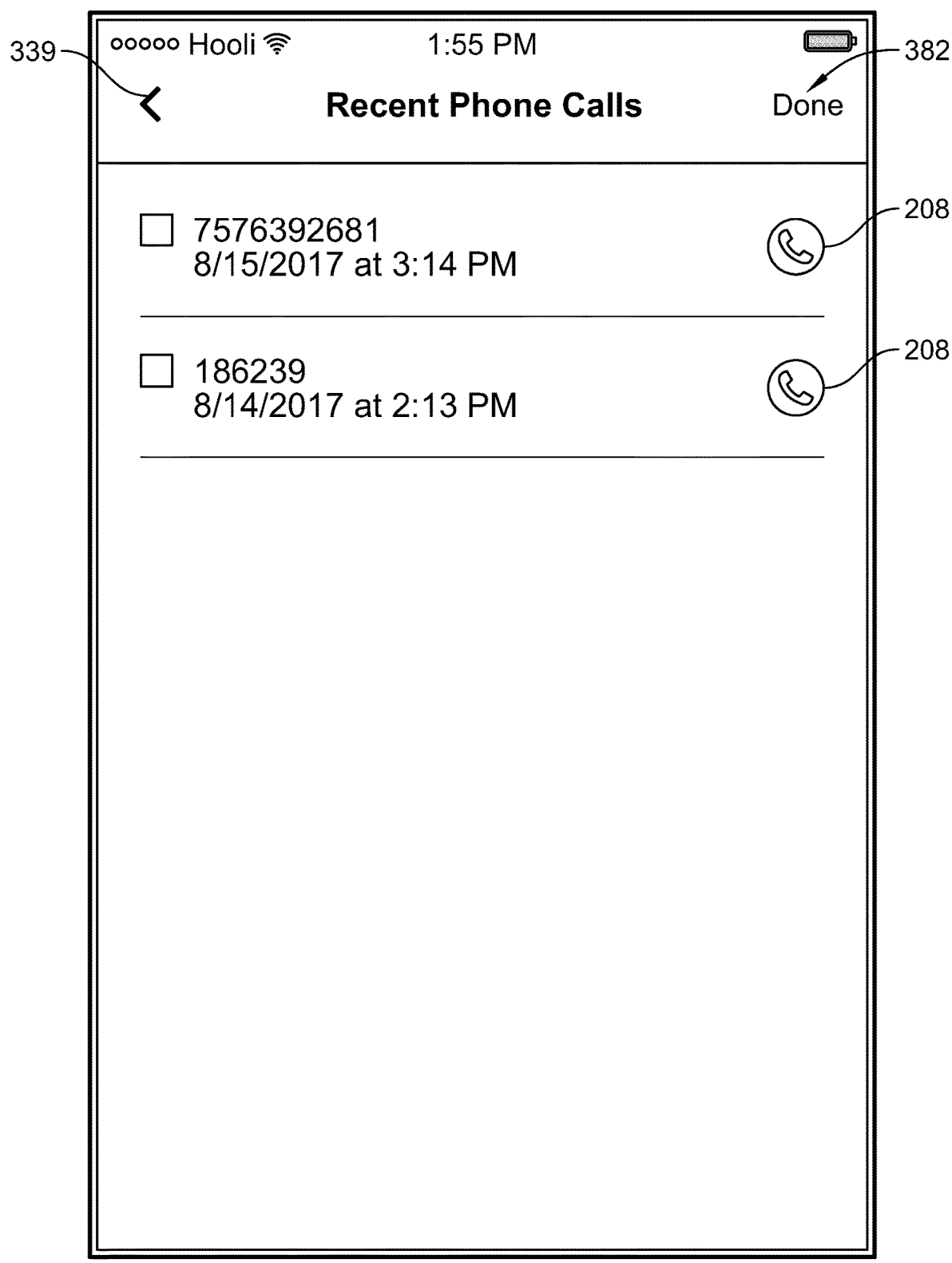
FIG. 46 is a screen shot of a Recent Phone Calls screen that appears on the caregiver's mobile device in response to selection of a Recents icon on the Dial Pad screen of FIG. 45.

Screen 392 includes a Recents icon 394 in the lower left corner of the screen 392. FIG. 46 shows a Recent Phone Calls screen 396 that appears on the caregiver's mobile device 52 in response to selection of the Recents icon 394 on the Dial Pad screen 392 of FIG. 45. Two recent phone calls are shown on screen 396 in the illustrative example. Icons 208 are provided in each row of the list of recent calls and are selectable to place a voice call to the respective phone number of the recent call.

The following provides additional information and also summarizes various aspects of the present disclosure:

Patient Details—The patient details screen is divided into two main sections. The top section shows relatively static information about the patient such as date of birth, risks, location, and the ability to call into the patient's room. The bottom section is subdivided into three sections: (1) Care Team—Shows all other caregivers who are assigned to care for this patient. Includes such details as their title (RN, Cardiologist, etc.), their location, and their availability; also includes options to message or call the caregiver if possible; tapping the message button will start a new conversation or look up an existing conversation between you and the selected caregiver with this patient as the subject; (2) Patient Notes—Shows the recorded notes for this patient; and (3) Nurse Call History—Shows a log of recent nurse calls, including the current state, the priority, how long ago it transpired, and who handled it.

Messages Tab—This tab contains everything to do with text messaging. List—The list of all conversations. From here you can also start a new conversation or check voicemail. Start New Conversation—A conversation can contain multiple caregiver participants. It can optionally reference a specific patient or location. New Conversation, Typing Participant—One way to add participants is to start typing a name. Any matching caregivers in your assigned unit(s) will be displayed and can be added with a tap. New Conversation, Browsing Caregivers—Alternatively, you can use the full staff browsing interface (the same as the Staff Tab) to find caregivers. The entire care team or unit can be added with a single tap. New Conversation, Typing Subject—One way to add a subject is to type the name of the patient or location. Any matches will be displayed and can be added with a tap. New Conversation, Browsing Subjects—Alternatively, you can use the full patient browsing interface (the same as the Patients Tab) to find a subject. Conversation with Picture—Pictures can be taken and displayed inline in a conversation. Multiparty Conversation—Each message is annotated with the sending party and the read status of your latest message is indicated. Conversation Details—You can see the subject, who is involved in this conversation and call them.

Staff Tab—This tab allows you to browse the staff members of any unit and also search for a specific caregiver, unit, or location. List—The tab defaults to displaying your assigned unit. Throughout the Staff Tab, units to which you are assigned are indicated with the bookmark icon. You can see your team, which is all the caregivers on your unit who share patient assignments with you, your entire unit, and a list of commonly needed contacts for the unit (such as pharmacy, social workers, chaplain, dietary, etc.). From this screen, you can also access the dial pad, perform a search, and browse to other units. Other Units—Other units within the enterprise can be browsed. They are grouped by a common ancestor. Tapping a unit displays the staff on that unit. Units to which you are assigned are indicated. Non-home List—When you are viewing a unit that is not one of your assigned units, you can go back "home" to it with just a tap. Tapped Search—Tapping the search field invokes the search screen. Search is very powerful and you are presented with a list of search criteria as a hint. Search "Carol"—This is an example of searching for a caregiver by name. Matching staff are displayed along with their assignment, their current location, and their availability. Tapping the row will navigate to that staff's details. Search "Onc"—This is an example of searching for a unit. The list is always kept in a particular order—Staff, Units, Locations, Favorites unless no results are found for that section. For a unit, its hierarchy in the enterprise is shown. Tapping will navigate to the list of staff in that unit. Search "4"—This example shows results for units, locations (which can be patient locations or ancillary locations), and favorites. No Results—If no results at all are found, the user is reminded of the search criteria. Dial Pad—There is an in-app dial pad so that an arbitrary number within the hospital may be called. Recents—This is a list of recent incoming and outgoing phone calls.

Me Tab—This tab displays information relevant to the currently logged in user. The top portion shows static details as well as the ability to change their availability. The bottom portion shows calls and favorites. Start—From here, the user can access settings and in-app help. They can also change availability. The Active Calls tab displays this user's open nurse calls. New calls are displayed at the top with a new indicator. You can see the state of the call, the originating location and patient, the priority, and the elapsed time. If there are actions to be taken on the call, a swipe to the left will reveal them, as in the second row. Favorites—A user can keep a list of favorite staff. They can be reordered and deleted at will. Add Favorite—There are currently two kinds of favorites: Arbitrary and Staff. Arbitrary favorites require the user to enter a label and a phone number. Staff favorites require the user to select a staff or location using the browse staff interface (the same as the Staff Tab). This choice must be made first. New Arbitrary Favorite—The favorite can be given any label and phone number and the app will attempt to dial the number as-is. Change Availability (DnD Inactive)—Tapping "Change" on the Me Tab will reveal the abilities to go on Do Not Disturb (DnD) or Sign Out completely. When going on DnD, you are able to choose a duration. One minute before DnD ends, you will receive a notification alerting you to the end of your DnD session. This notification will give you the option to further extend it another 5 minutes or let it elapse. Change Availability (DnD Active)—When DnD is active, it can be terminated at any time.

A Session Initiation Protocol (SIP) stack is used to provide secure voice, video, and text communication between device-to-device communication of devices 52 and between devices 52 and other equipment of system 50.

Figure 47:
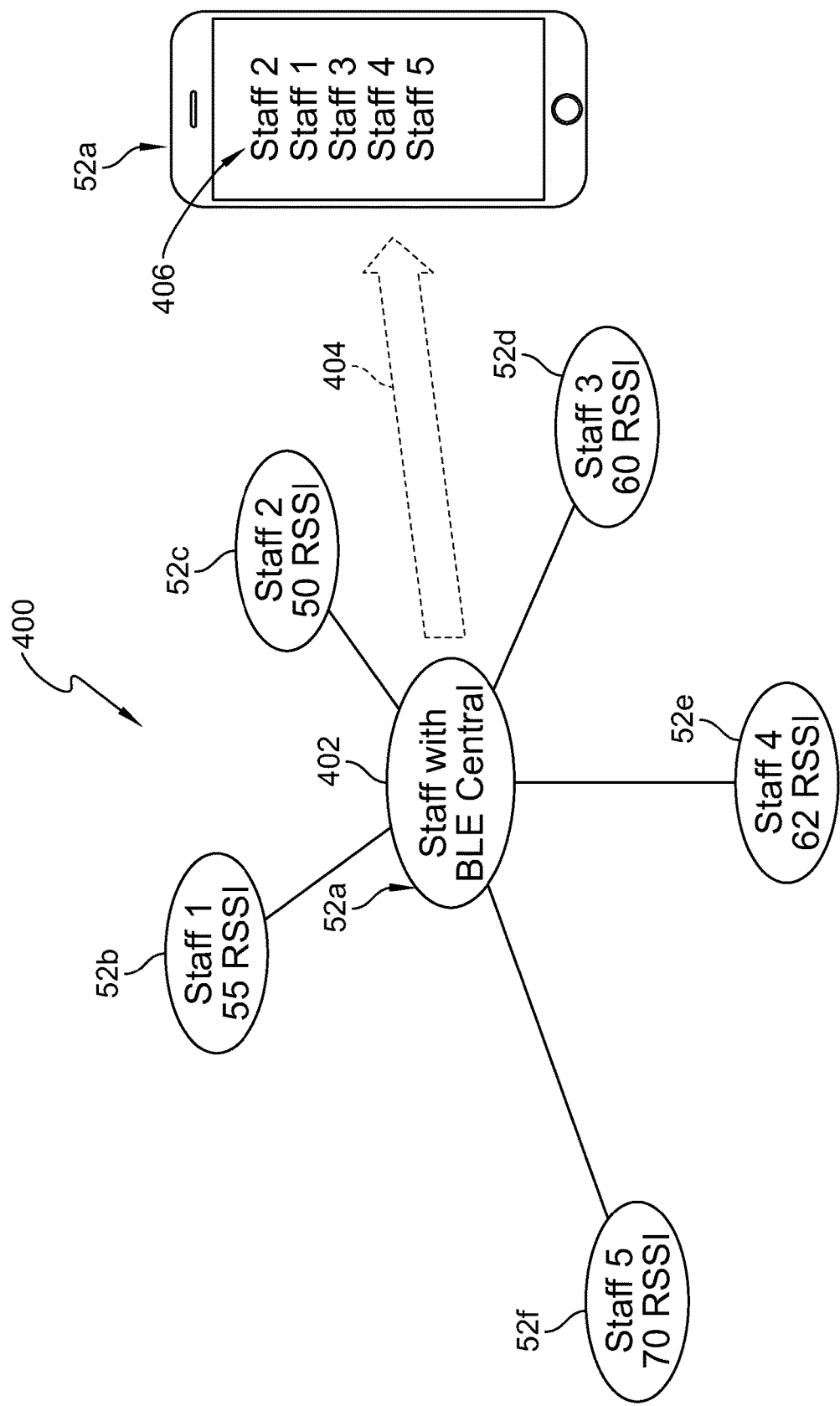
FIG. 47 is a block diagram showing a mobile device of a caregiver that has received signal strength indication (RSSI) software to determine a distance between the caregiver and other caregivers labeled as Staff 1-5 and showing a screen of the mobile device rank ordering the Staff 1-5 based on relative location, closest to farthest, from the caregiver.

Referring now to FIG. 47, a block diagram 400 shows an embodiment in which mobile device 52a of a first caregiver is equipped with received signal strength indication (RSSI) software 402, as indicated by dotted arrow 404. Software 402 is Bluetooth Low Energy (BLE) Central software in the illustrative example. Staff members in the vicinity of mobile device 52a have mobile phones 52b-f that serve as BLE peripherals of device 52a. Based on the received signal strength of messages between device 52a and each of devices 52b-f, an RSSI is determined by device 52a. In the illustrative example of FIG. 47, mobile devices 52b-f are carried by five different staff members as indicated by the text Staff 1-5 in each block corresponding to devices 52b-f. As also indicated in the blocks corresponding to devices 52b-f, a numerical RSSI value is provided indicating, for example, the distance in feet between device 52a and each of devices 52b-f. In the illustrative example of FIG. 47, device 52b is 55 feet away from device 52a, device 52c is 50 feet away from device 52a, device 52d is 60 feet away from device 52a, device 52e is 62 feet away from device 52a, and device 52f is 70 feet away from device 52a.

Software 402 is operable to provide a rank ordered listing 406 on the display screen of device 52a screen to indicate the relative locations or distances of the five staff members, from closest to farthest, away from the caregiver carrying device 52a. In the illustrative example, Staff 2 is the closest to the caregiver carrying device 52, Staff 1 is the second closest, Staff 3 is the third closest, Staff 4 is the fourth closest, and Staff 5 is the farthest away from the caregiver carrying 52a. It should be understood that list 406 may include more or less than five staff members depending upon how many mobile devices 52 are within the reception range of device 52a for purposes of determining the RSSI using software 402. In some embodiments, the staff members shown on list 406 are contacted by the caregiver carrying device 52a in response to touching or otherwise selecting the Staff 1-5 text in list 406. The Staff 1-5 text in FIG. 47 is used in place of the caregiver names for illustrative purposes. That is, this disclosure contemplates that list 406 contains the names of the staff members whose mobile devices 52 are in reception range of device 52a. Selection of one of the staff member names in list 406 results in a voice call being made to the respective mobile device 52a-f, as the case may be, of the selected staff member or results in a text message window appearing for sending a text message to the mobile device 52a-f of the selected staff member. In some embodiments, a window or screen may appear in response to selection of a staff member name on list 406 giving the caregiver carrying device 52a the option to place a voice call or compose a text message.

In some embodiments, mobile devices 52b-f advertise the availability of the associated staff member to device 52a such that unavailable staff members do not appear on list 406. Messages to device 52a from devices 52b-f regarding staff member availability include some identifying data and a security token in some embodiments. It is contemplated by this disclosure, therefore, that the caregiver carrying device 52a opens up software 402 via an appropriate selection of an icon on the display screen of device 52a when the caregiver wishes to contact another staff member, such as for help with a patient, just to give one example.

In some embodiments, the caregiver carrying device 52a is able to filter the other staff members that are to appear on list 406 by role. For example, the caregiver carrying device 52a may want to find out which housekeeping staff is in the vicinity or which nursing technicians are in the vicinity, just to give a couple of examples. Thus, only the staff members having the selected role or roles in those embodiments permitting selection of more than one role, will appear on list 406 and staff members not having the selected role(s) are omitted from list 406. The software 402 scans the advertisements from the mobile devices 52 within reception range after the roles are selected. The software 402 resolves the information from the advertisements into names of staff members and their roles. Then, software 402 operates to display on list 406 the staff members meeting the search criteria (e.g., roles) based on the RSSI as described above. The caregiver carrying device 52a can then call or text a selected staff member as also described above.

Figure 48:
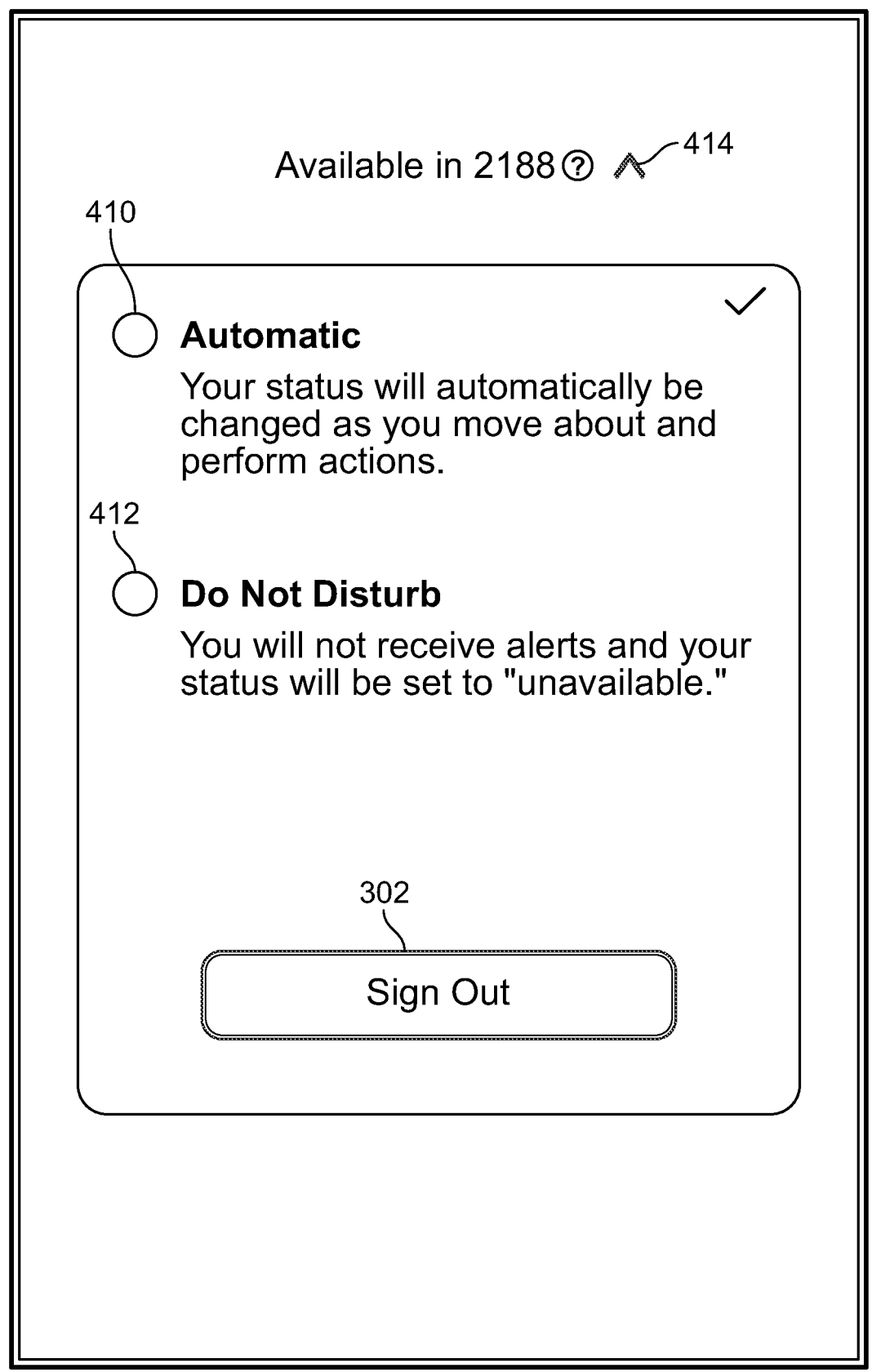
FIG. 48 is a screen shot of an Availability screen that a caregiver uses to select an Automatic availability function in which the caregiver's availability status changes automatically as the caregiver moves about a healthcare facility and to select a Do Not Disturb function in which the caregiver ceases to receive alerts and is indicated as unavailable on other devices of the system.

Referring now to FIG. 48, is a screen shot of another example of an Availability screen 408, similar to screen 294 of FIG. 23 and screen 306 of FIG. 24 discussed above. Screen 408 includes an Automatic radio button 410 that a caregiver uses to turn on and off, via sequential selections of button 410, an Automatic availability function. When the Automatic availability function is turned on, or active, radio button 410 is filled in and the caregiver's availability status changes automatically as the caregiver moves about the healthcare facility. For example, when the caregiver is in a patient room, the caregiver's availability status is set to unavailable and when the caregiver leaves the patient room and is in a public area of the healthcare facility, such as a hallway, the caregiver's availability is set to available. In some embodiments, the Automatic availability function is turned on as a default setting during the caregiver's shift. When the Automatic availability function is turned off, radio button 410 is empty or not filled in.

Screen 408 of FIG. 48 also has a Do Not Disturb radio button 412 that a caregiver uses to turn on and off, via sequential selections, a Do Not Disturb function. When the Do Not Disturb function is turned on, or active, radio button 412 is filled in and the caregiver ceases to receive alerts. The caregiver is also indicated as unavailable on other devices of the system 50 in response to the Do Not Disturb function being active. In response to the Do Not Disturb function being turned off, radio button 412 is empty or not filled in and the caregiver is, once again, able to receive alerts. Screen 408 also has Sign Out icon 302 which operates the same as described above in connection with FIGS. 23 and 24. Thus, icon 302 is selected by the caregiver to sign out at the end of their shift. After sign out, the caregiver is no longer available to receive alert messages occurring within system 50. An up arrow icon 414 is provided in the top region of screen 408 and is selected by the caregiver to close out of screen 408 and return to the previous screen.

Figure 49:
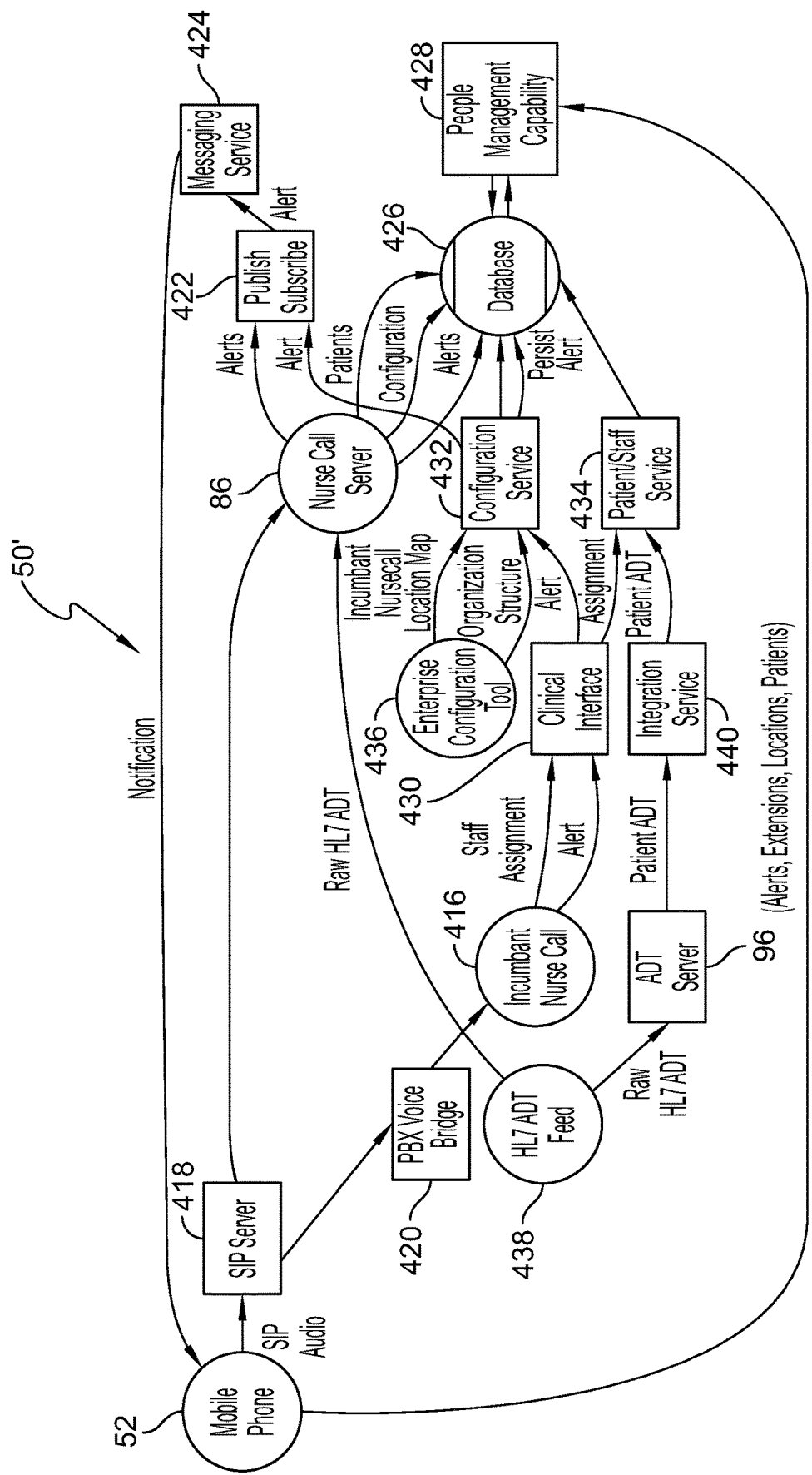
FIG. 49 is a block diagram of a network architecture implementing an embodiment of a caregiver and staff information system in which a healthcare facility has two different types of nurse call systems.

Referring now to FIG. 49, a block diagram of a caregiver and staff information system 50', similar to system 50 of FIG. 1, is shown having a network architecture according to an embodiment contemplated by the present disclosure. System 50' is illustrative of the scenario in which a healthcare facility has two different types of nurse call systems. Like system 50, system 50' has caregivers with mobile devices such as phones 52 (only one mobile device 52 is shown in FIG. 49), a nurse call server 86 and an ADT server 96. Nurse call server 86 is part of the first nurse call system of overall system 50' and a second nurse call server 416 is included in system 50' as part of the second nurse call system. System 50' is configured so that alerts arising in both the first and second nurse call systems are able to be sent to mobile phones 52 for display using the caregiver and staff communication software application contemplated herein and described in connection with FIGS. 1-48 and 50-59.

System 50' includes a Session Initiation Protocol (SIP) server 418 that receives SIP Audio from mobile phones 52 as shown in FIG. 49. SIP server 418 communicates with nurse call server 416 via a Private Branch Exchange (PBX) bridge 420. However, no PBX bridge is needed in order for SIP server 418 to communicate with nurse call server 86. Thus, the first and second nurse call systems are configured for different types of voice communications in system 50'. Alerts occurring within the first nurse call system are communicated from nurse call server 86 to a publish/subscribe application which, in the illustrative embodiment, is stored on a publish/subscribe server 422 which, in turn, provides the alerts to a messaging service application or server 424 for communication to one or more phones 52. In some embodiments, the publish/subscribe application or server 422 keeps track of which phones 52 are to receive which alerts occurring in the first nurse call system. For example, the publish/subscribe application or server 422 includes information regarding the phone numbers of devices 52 of caregivers that are assigned to the patient or room from which the alerts are being generated.

Nurse call server 86 of system 50' also sends alert data, configuration data, and patients data for storage in a database 426 as indicated by the arrows labeled Alerts, Configuration, and Patients that extend from server 86 to database 426 in FIG. 49. Database 426 is also in two-way or bidirectional communication with a people management capability server 428. Mobile phones 52 are a further source of information for server 428 and provide data regarding alerts, extensions, locations, and patients to server 428.

Nurse call server 416 of the second nurse call system of overall system 50' sends alerts and staff assignment data to a clinical interface application or server 430. Clinical interface server 430 separates the incoming data from nurse call server 416 such that the alerts are sent to a configuration service application or server 432 and such that the staff assignment data is sent to a patient/staff service application or server 434. Server 434 is linked to database 426 to communicate patient/staff assignment data to database 426.

Configuration service server 432 reformats and otherwise converts the alert data received from the clinical interface application 430 of the second nurse call system so as to be compatible with the format and protocols required by the caregiver and staff communication software application contemplated herein and described in connection with FIGS. 1-48 and 50-59. An Enterprise Configuration Tool (ECT) 436 is provided for programming the manner in which the configuration service server 432 reformats or converts the incoming alerts from clinical interface 430 into the outgoing alerts. For example, the ECT 436 is used to alter the organization and structure of the incoming alerts.

The ECT 436 also is used to reconfigure the location structure data from the second nurse call system to facilitate mapping into database 426 in the same manner that location structure data is mapped from the first nurse call system. In this regard, the ECT 436 has an import/export capability. The staff-to-patient assignment information is similarly mapped by the patient/staff service server 434 so as to match the manner that staff-to-patient assignment information is mapped in the first nurse call system. The reconfigured location structure and staff-to-patient assignment data is stored in database 426. The ECT 436 is a software application that, in some embodiments, is executed by server 432 and, in other embodiments, is executed on its own server or some other server.

The reconfigured and/or reformatted alerts from the configuration service server 432 are transmitted to the publish subscribe server 422 which, in turn, provides the reconfigured and/or reformatted alerts from the second nurse call system to the messaging service server 424 just like the alerts originating from the first nurse call server which do not need to be reconfigured or reformatted prior to receipt by the publish subscribe server 422 or the messaging service server 424. The alerts originating from both the first and second nurse call systems are transmitted from the messaging service server 424 to the appropriate mobile devices 52 of caregivers assigned to the patient or rooms from which the alerts were generated.

In the illustrative example of FIG. 49, a health level seven (HL7) admission/discharge/transfer (ADT) feed or server 438 communicates raw HL7 ADT data to nurse call server 86 and ADT server 96. The raw HL7 ADT data, in some instances, also may be indicative of alert conditions that, in turn, are sent from nurse call server 86 to one or more mobile devices 52 via servers 422, 424. The ADT server 96 extracts patient ADT data from the raw HL7 ADT data and transmits it to an integration service server 440 which, in turn, transmits the patient ADT data to patient/staff service server 434. Server 434 subsequently transmits the patient ADT data to database 426 for storage. The staff-to-patient assignment data and/or the staff-to-room assignment data and/or the staff-to-patient-to-room assignment data from the second nurse call system is stored in database 426 and is used by other portions of system 50' so that the same assignment data does not need to be entered a second time in some other portion of system 50'.

Figure 50:
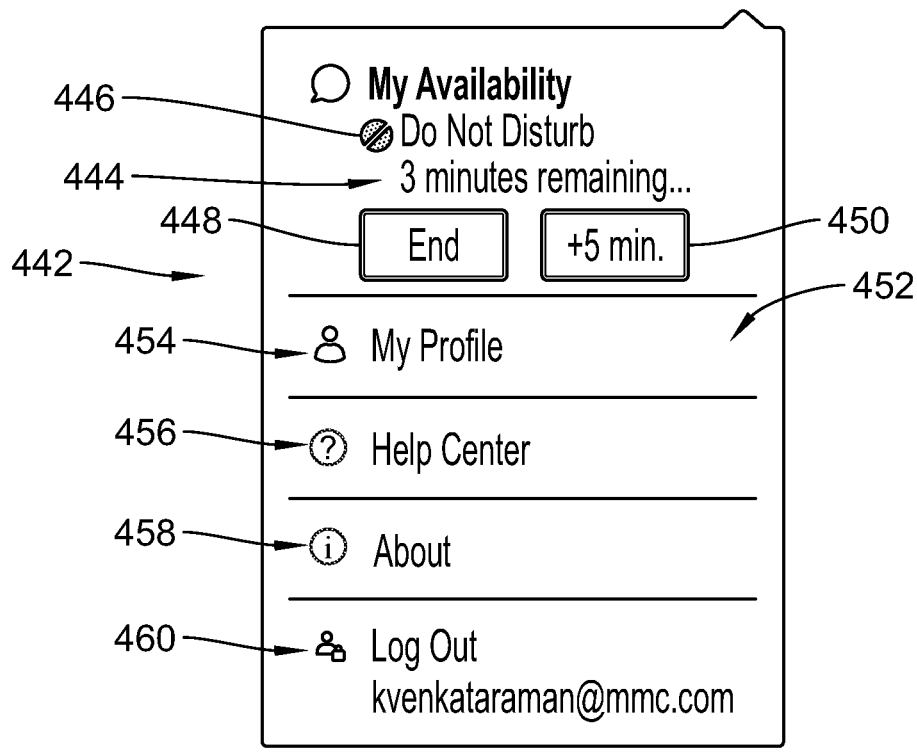
FIG. 50 is a screen shot of a first My Availability screen showing that a caregiver has three minutes remaining of a Do Not Disturb status and showing a graphical End button that the caregiver selects to end the Do Not Disturb status and a graphical +5 min. button that the caregiver selects to extend the Do Not Disturb status by an additional five minutes.

Referring now to FIG. 50, an example is given of a first My Availability screen 442 that appears on the display screen of a caregiver's mobile device 52 in some embodiments contemplated herein. For example, screen 442 appears on the caregiver's mobile device 52 after Do Not Disturb icon 412 of screen 408 of FIG. 48 is selected. Screen 442 has a line of text 444 indicating that the caregiver has three minutes remaining of a Do Not Disturb status. A Do Not Disturb icon 446 appears above the line of text 444 to further indicate that the caregiver has selected Do Not Disturb as their availability status. Screen 442 also includes a graphical End button 448 that the caregiver selects to end the Do Not Disturb status and a graphical +5 min. button 450 that the caregiver selects to extend the Do Not Disturb status by an additional five minutes. Beneath buttons 448, 450, screen 442 includes a menu 452 having, from top to bottom, a My Profile icon 454 that the caregiver selects to navigate to their profile information, a Help Center icon 456 that the caregiver selects to link to a help center, an About icon 458 that a caregiver selects to obtain further information about patients, and a Log Out icon 460 that a caregiver selects to log out of the caregiver and staff communication software application.

Figure 51:
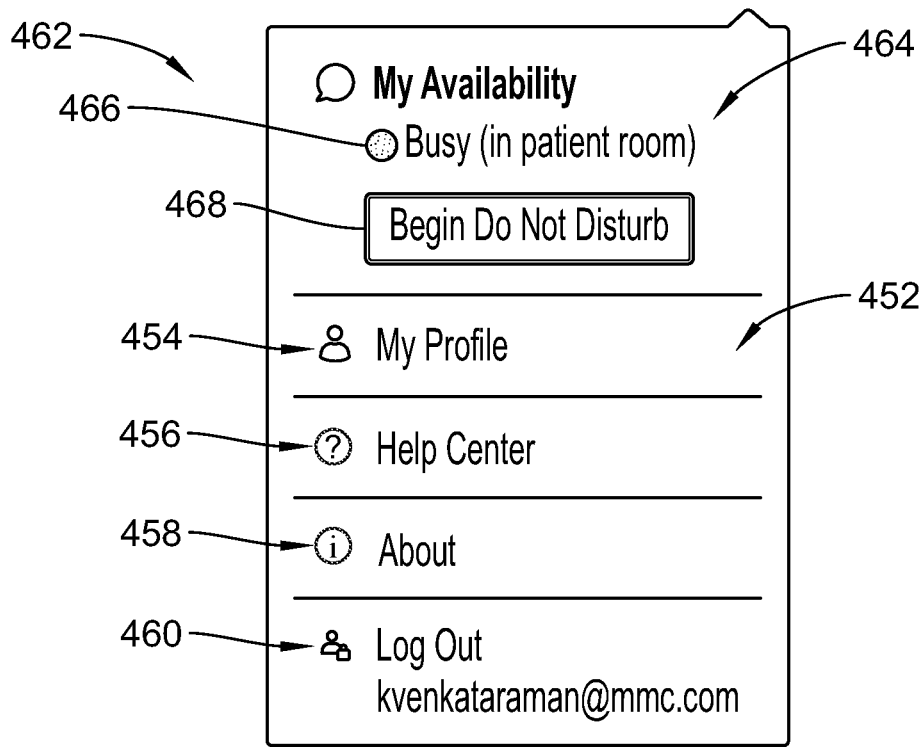
FIG. 51 is a screen shot of a second My Availability screen showing that a caregiver has a status of Busy (in patient room) and showing a graphical Begin Do Not Disturb button that the caregiver selects to change their status to Do Not Disturb.

Referring now to FIG. 51, an example is given of a second My Availability screen 462 that appears on the display screen of the caregiver's mobile device 52 in some embodiments contemplated herein. For example, screen 462 appears on the caregiver's mobile device 52 after Automatic icon 410 of screen 408 of FIG. 48 is selected and after the caregiver enters a patient room. Screen 462 has a line of text 464 indicating that the caregiver is Busy and in a patient room. A Busy icon 466 appears to the left of the line of text 464 to further indicate that the caregiver's current status is Busy. Screen 462 also includes a graphical Begin Do Not Disturb button 468 that is located beneath the line of text 464 and icon 466 and that the caregiver selects to change their status to the Do Not Disturb status. Screen 462 also includes menu 452 and icons 454, 456, 458, 460 and the description of these above is equally applicable.

Figure 52:
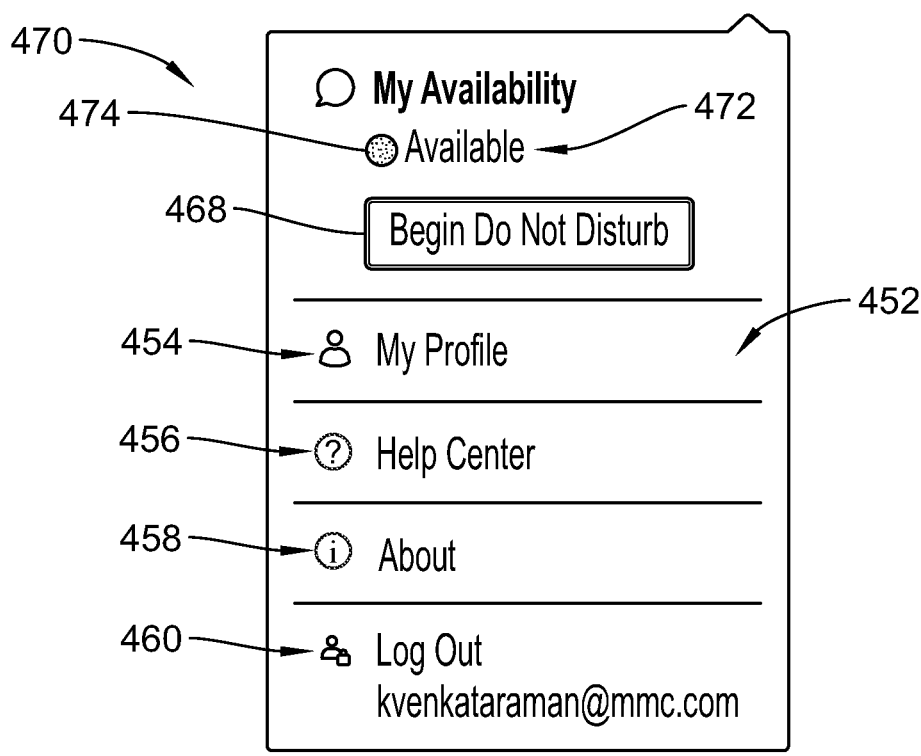
FIG. 52 is a screen shot of a third My Availability screen showing that a caregiver has a status of Available and showing the graphical Begin Do Not Disturb button that the caregiver selects to change their status to Do Not Disturb.

Referring now to FIG. 52, an example is given of a third My Availability screen 470 that appears on the display screen of the caregiver's mobile device 52 in some embodiments contemplated herein. For example, screen 470 appears on the caregiver's mobile device 52 after Automatic icon 410 of screen 408 of FIG. 48 is selected and after the caregiver enters a public area of the healthcare facility, such as a hallway. Screen 470 has a line of text 472 indicating that the caregiver is Available and an Available icon 474 appears to the left of the line of text 472 to further indicate that the caregiver's current status is Available. Like screen 462, screen 470 also includes the graphical Begin Do Not Disturb button 468 that is located beneath the line of text 472 and icon 474 and that the caregiver selects to change their status to the Do Not Disturb status. Screen 470 also includes menu 452 and icons 454, 456, 458, 460 and the description of these above is equally applicable.

Icons 446, 466, 474 of respective screens 452, 462, 470 are color coded in some embodiments. For example, icon 446 is red, icon 466 is yellow, and icon 474 is green in one contemplated embodiment. In other embodiments, a different color coding scheme may be used for each of icons 446, 466, 474.

According to the present disclosure, one or more desktop computers including computer devices such as primary staff console 78 (aka master nurse station computer), staff console 80, staff terminal 82, or a caregiver tablet computer (similar to patient tablets 56) of FIG. 1 also have the caregiver and staff communication software application loaded thereon such that the desktop computer(s) is/are able to engage in secure voice and text communications with mobile devices 52 of other caregivers. Examples of the manner in which the caregiver and staff communication software application is used on a desktop computer are provided in FIGS. 53-59 and are discussed below.

Figure 53:
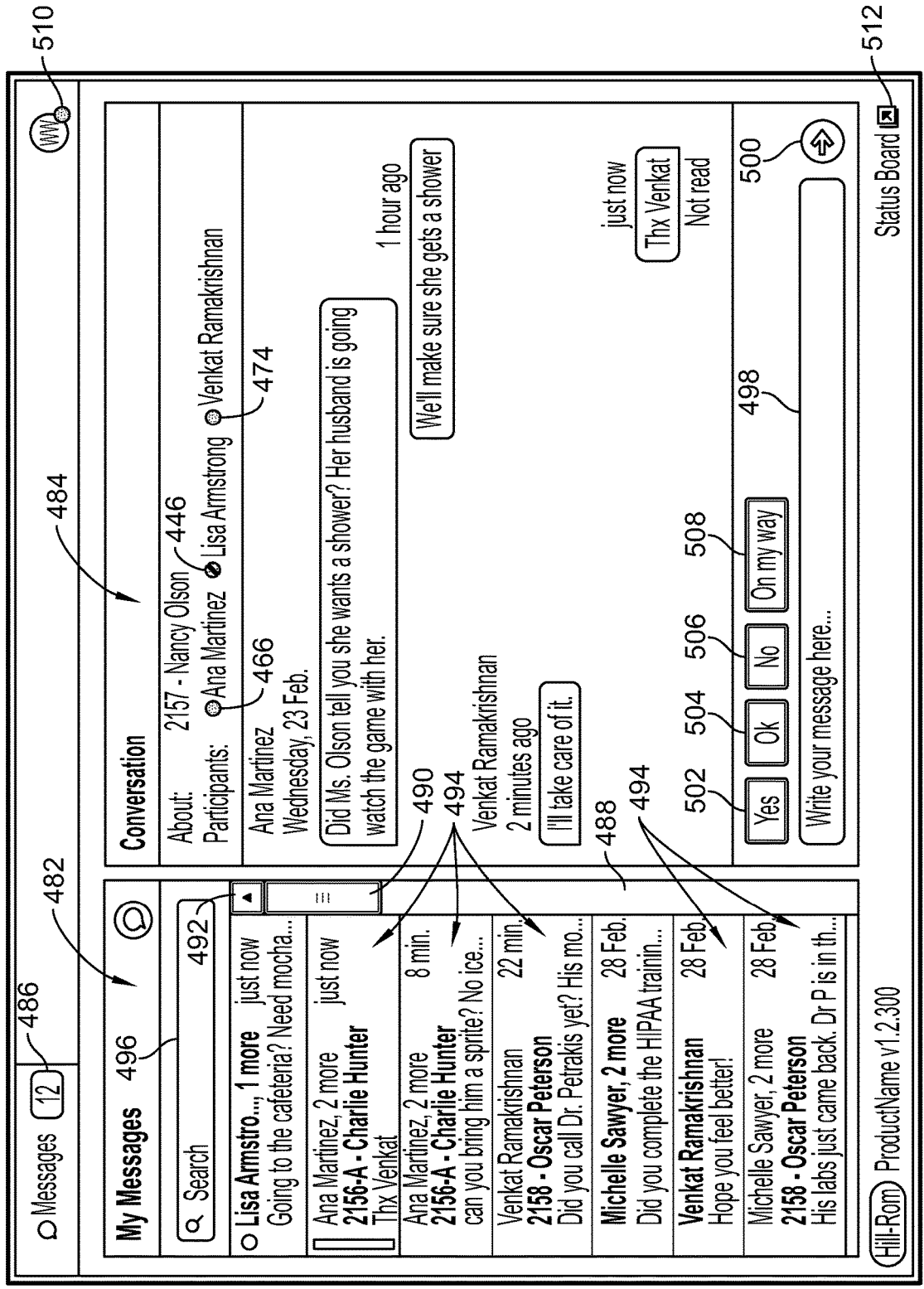
FIG. 53 is a screen shot showing a Past Conversation screen displayed on a desktop display screen of a computer that is used to view a past text message conversation between other caregivers about a particular patient and showing, at the top of the text message conversation, the current availability status of the caregivers involved in the past text message conversation.

Referring now to FIG. 53, an example is given of a Past Conversation screen 480 that appears on a desktop computer during use of the caregiver and staff communication software communication application contemplated herein. Screen 480 includes a My Messages window 482 on a left side of screen 480 and a Conversation window 484 to the right of window 482. Window 482 takes up roughly one third of the area of screen 480 and window 484 takes up roughly two thirds of screen 480, not including a header area above windows 482, 484 and a footer area beneath windows 482, 484. Window 482 includes a list of the past conversations in which the caregiver using the desktop computer has participated.

In the header area of screen 480, a box 486 indicates the number of past conversations appearing in window 482. In the illustrative example of FIG. 53, box 486 indicates that there have been twelve past conversations for the caregiver. However, window 482 only presents information, in abbreviated form, for seven of the twelve past conversations. Thus, window 482 includes a scroll bar 488 and a movable scroll icon 490 that can be selected and dragged along bar 488 to reveal the other past conversation information that is currently not displayed in window 482. A scroll arrow 492 is illustrated above scroll bar 488 in the illustrative example and can be selected to scroll through the past conversation information in window 482 as well. A similar scroll arrow appears beneath scroll bar 488 in appropriate circumstances.

The abbreviated past conversation information in window 482 is provided in blocks 484. Each block contains a date (e.g., 28 February for three of blocks 494 of window 482 in the illustrative example) or a duration, in minutes, since the most recent entry of a past conversation or indicates "just now" if the conversation is ongoing currently. A duration cutoff, such as 5 minutes, may delineate whether to indicate the duration in minutes since the most recent entry or whether to designate the conversation as "just now." The abbreviated past conversation information in blocks 494 also includes the name, or a portion of the name, of the caregiver that initiated the past conversation; the name, or a portion of the name, of the patient to which the past conversation pertains; the room number of the patient to which the past conversation pertains; and the caregiver's most recent entry, or a portion of the caregiver's most recent entry, in the past conversation.

Window 482 lists the abbreviated past conversation information in blocks 494 in order from most recent, at the top of window 482, to oldest, at the bottom of window 482. Selection of one of blocks 494 by the caregiver, such as by placing a cursor over the block 494 and clicking a button of a mouse or on a keyboard or by touching the desired block 494, results in the selected past conversation being displayed in window 484 of screen 480. A search box 496 appears in window 482 above blocks 494. The caregiver is able to select box 496 and then type a search string into box 496 to search for past conversations having the search string therein. Thus, use of search box 496 filters out past conversations not meeting the search criteria and only those past conversations meeting the search criteria appear in window 492.

Window 484 shows the messages between the various caregivers who participated in the past conversation selected from the list in window 482. The name and room number of the patient about which the selected past conversation pertained is shown at the top window 484. Beneath the patient's name and room number, the names of the participants of the selected past conversation are shown. In the illustrative example, the appropriate one of the availability icons 446, 466, 474 for each past message participant is shown to the left of the name of each participant of the past conversation. Icons 446, 466, 474 in window 484 indicate the participant's current availability status. Icons 446, 466, 474 were discussed above in connection with FIGS. 50-52 and indicate the same availability status (unavailable or Do Not Disturb, Busy, or Available, as the case may be) on the desktop computer as they do on mobile devices 52.

After a past conversation has been selected in window 482 for display in window 484, the caregiver using the desktop computer can post another message in the conversation. A message box 498 appears at the bottom of window 484 beneath the selected past conversation. The caregiver is able to select box 498 and then type a message into box 498. After the caregiver completes the desired message, the caregiver selects a post icon 500 to post the message in box 498 to the conversation. Posting the message in this manner results in the message being sent to the mobile device of each of the participants of the past conversation appearing in window 484. Once posted to the conversation, the message in box 498 disappears from box 498 and appears in window 484 beneath the previously most recent message in the conversation.

Just above box 498 at the bottom of window 484 are a set of icons, each having a predetermined short word or phrase that can be selected to appear in box 498. In the illustrative example, these icons include a "Yes" icon 502, an "Ok" icon 504, a "No" icon 506, and an "On my way" icon 508. Thus, icons 502, 504, 506, 508 are common phrases that caregivers use during their shifts to communicate with one another. By providing icons 502, 504, 506, 508 in window 485, caregiver efficiency is increased because they do not need to manually type these common words and phrases into box 498 each time they wish to use them. After the caregiver is finished selecting one or more of icons 502, 504, 506, 508 to cause the associated word or phrase to appear in box 498, the caregiver selects post icon 500 as discussed above to post the message in box 498 to the conversation appearing in window 484.

In the top right header area of screen 480, a connectivity icon 510 is provided to indicate the connectivity status of the desktop computer to the network (e.g., other devices) of system 50. For example, in some embodiments, icon 510 is colored green to indicate that the desktop computer is successfully communicating in system 50 and is colored red or amber to indicate a connectivity problem. In the bottom right footer area of screen 480, a status board icon 512 is provided and is selectable by the caregiver to bring up a status board for display on the desktop computer. Additional details of a status board can be found in U.S. Pat. No. 8,779,924, particularly with reference to FIG. 3, and which is hereby incorporated by reference herein for all that it teaches to the extent not inconsistent with the present disclosure which shall control as to any inconsistencies.

Figure 54:
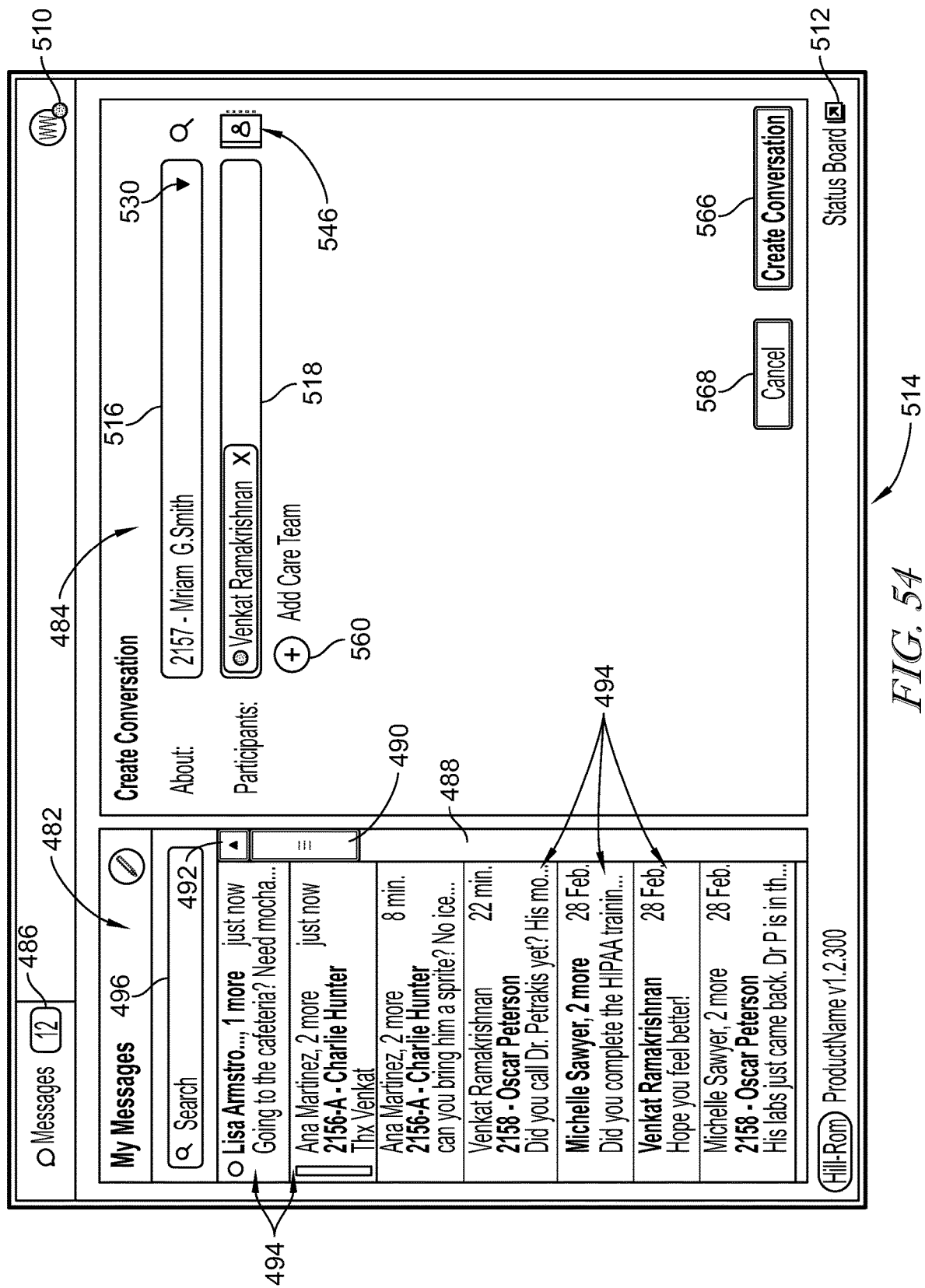
FIG. 54 is a screen shot showing a Create Conversation screen displayed on a desktop display screen of a computer that is used to create a text message conversation with one or more other caregivers about a particular patient and showing, at the top of the text message conversation, a caregiver designated as a participant in the text message conversation.

Referring now to FIG. 54, an example is given of a Create Conversation screen 514 that appears on the desktop computer during use of the caregiver and staff communication software communication application if one of the past conversations is not being displayed in window 484. Screen 514 of FIG. 54 has many of the same fields, boxes, and icons as screen 480 of FIG. 53 and so, like reference numbers are used and the description above of screen 480 is equally applicable to the like portions of screen 514. A couple of the main differences between screen 480 and screen 514 is that window 484 of screen 514 includes an About box 516 and a Participants box 518 at the top region of window 484. Box 516 lists the name and room number of the patient about which the conversation being created by the caregiver is to pertain. Box 518 lists the one or more caregivers who are selected for participation in the conversation being created.

Figure 55:
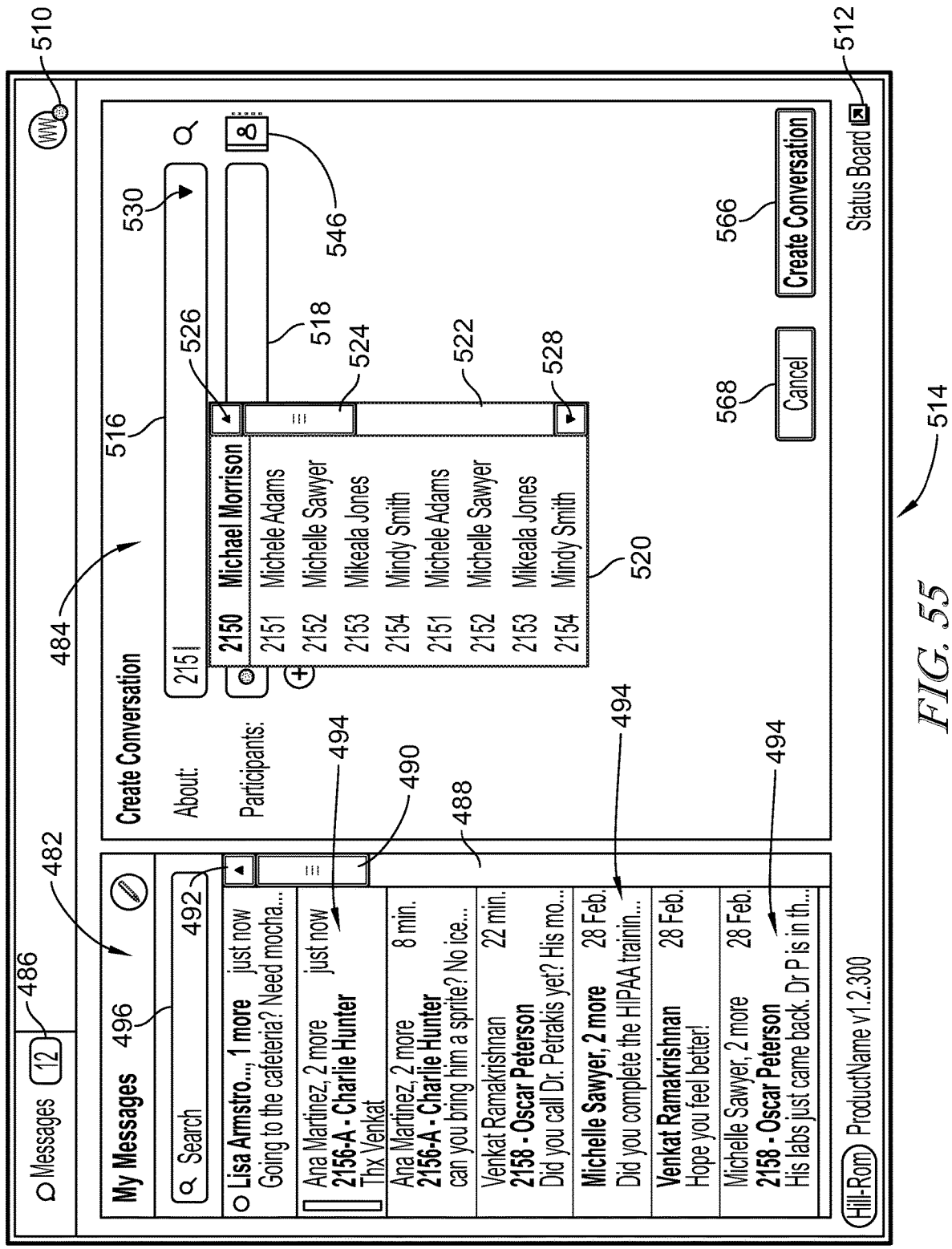
FIG. 55 is a screen shot, similar to FIG. 54, showing an example of a drop down menu of patient names and locations that appears on the Create Conversation screen in response to a portion of a room number being typed in an About text field near the top of the Create Conversation screen.

As shown in FIG. 55, in response to a room number of a patient being typed into box 516, a drop down menu 520 appears in window 484 beneath box 516. Menu 520 is a dynamic menu in that, as the caregiver types more digits into box 516, only those room numbers and associated patient names matching the partially typed room number are displayed in the menu 520. Thus, when the first digit of the patient's room number, "2" in the illustrative example, is typed into box 516, all room numbers that begin with the first digit are shown in menu 520. Then, when the second digit of the patient's room number, "1" in the illustrative example, is typed into box 516, all room numbers that begin with the first two digits are shown in menu 520. As shown in FIG. 55, the third digit of the patient's room number, "5" in the illustrative example, has been typed into box 518 and, therefore, menu 520 of FIG. 55 lists the patient room numbers and patient names of all of the rooms having the first three typed digits, "215" in the illustrative example.

If desired, the caregiver can select the desired patient from the menu 520 before the complete room number of the patient has been typed. In the illustrative example, menu 520 is of a certain size that, in many cases, does not permit all patient rooms that meet the partially typed room number criteria from being viewable in the menu 520. Thus, a scroll bar 522, a scroll icon 524, a scroll up arrow icon 526, and a scroll down arrow icon 528 are provided at the right of menu 520. The caregiver using the desktop can select and drag icon 524 along bar 522 or can select icons 526, 528 to scroll up and down, respectively, to view other room numbers meeting the search criteria. In FIG. 54, box 516 contains "2157—Miriam G. Smith" therein and so, in the illustrative example of FIG. 55, it can be seen that the caregiver would need to scroll down to view the room 2157 information for subsequent selection. After a patient name and room number is selected from menu 520, the selection appears in box 516 and menu 520 disappears from screen 514.

Figure 56:
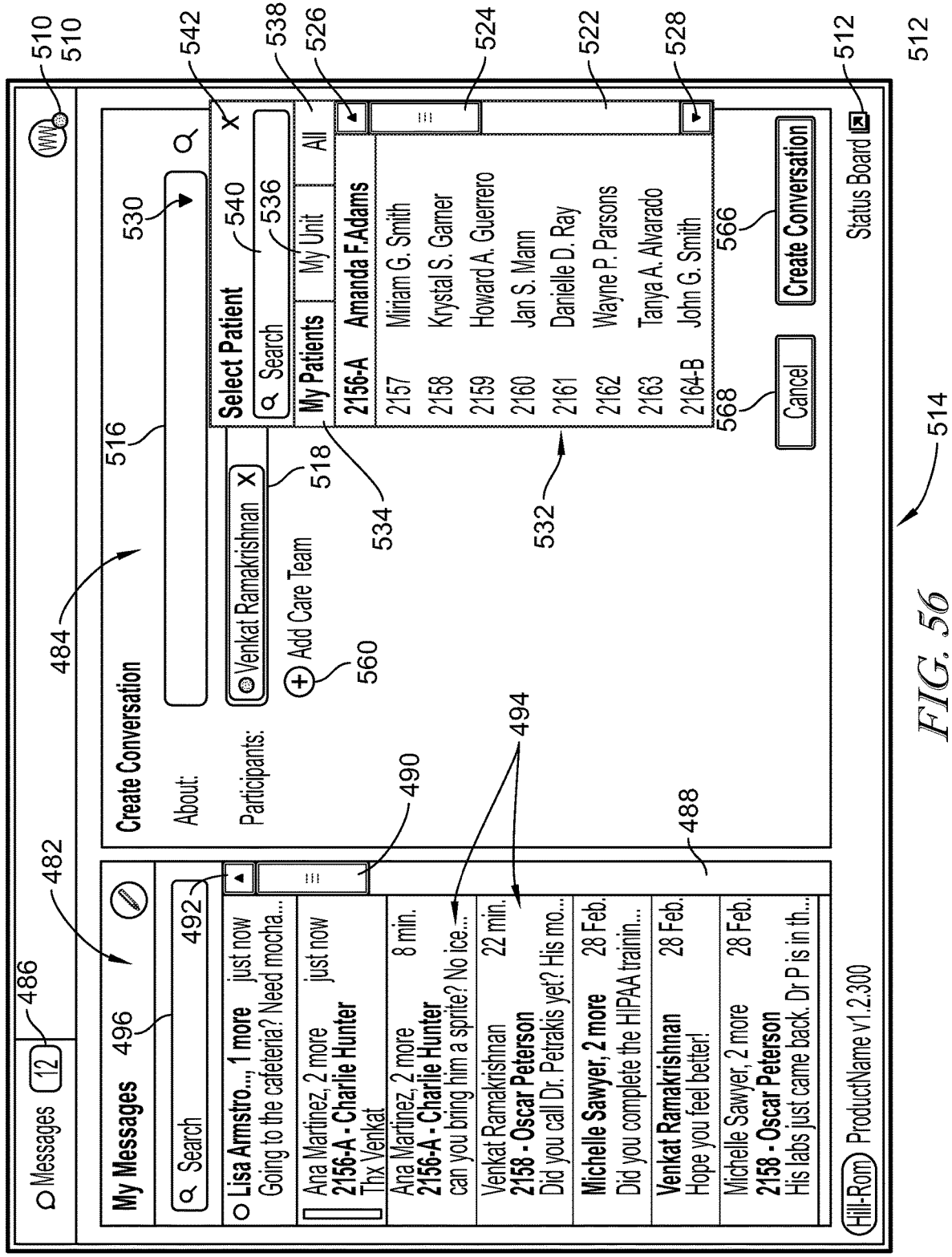
FIG. 56 is a screen shot, similar to FIG. 54, showing an example of a drop down menu of patient names and locations that appears on the Create Conversation screen in response to selection of a down arrow icon appearing on the right hand side of the About text field.

Box 516 of window 484 of screen 514 also includes a down arrow or search icon 530 that the caregiver can select, if desired, to bring up a menu 532 of rooms and patient names as shown, for example, in FIG. 56. Thus, selection of icon 530 to bring up menu 532 is an alternative way to search for a desired patient rather than typing a room number into box 516. As shown in FIG. 56, menu 532 includes a My Patients tab 534, a My Unit tab 536, and an All tab 538. In the given FIG. 56 example, the My Patients tab 534 has been selected and so menu 532 lists the room number and patient names for the patients that have been assigned to the caregiver using the desktop computer. Selecting My Unit tab 536 results in menu 532 listing all room numbers and patient names for the caregiver's unit and selecting the All tab 538 results in menu 532 listing all patients in the healthcare facility (or at least all the patients known in system 50 in connection with the caregiver and staff communication software application).

The right hand portion of menu 532 has scroll bar 522, scroll icon 524, scroll up arrow icon 526, and scroll down arrow icon 528 that operate the same in connection with menu 532 as was discussed above in connection with menu 520. Thus, the description is not repeated. Above tabs 534, 536, 538 is a search box 540 in which a patient's name or room number can be typed by the caregiver as an alternative search methodology. In some embodiments, menu 532 is dynamic and lists the patients and room numbers meeting the search criteria of the partially typed information in box 540. After a patient name and room number is selected from menu 532, the selection appears in box 516 and menu 532 disappears from screen 514. Alternatively, if the caregiver decides not to make a selection from menu 532, then a close icon 542 is selected to close menu 532.

Figure 57:
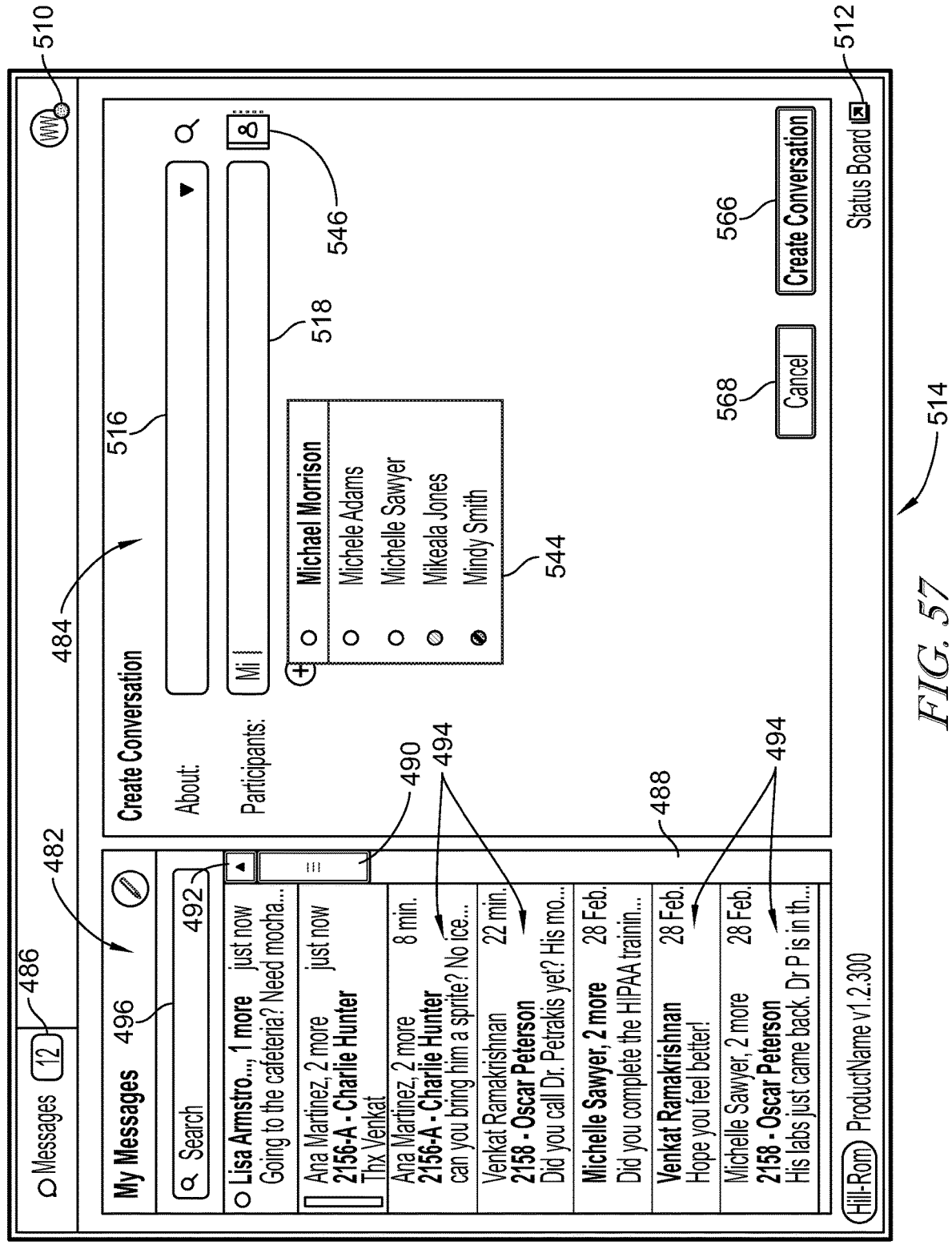
FIG. 57 is a screen shot, similar to FIG. 54, showing an example of a drop down menu of caregiver names and availability status that appears on the Create Conversation screen in response to a portion of a caregiver name being typed in a Participant text field near the top of the Create Conversation screen.

As shown in FIG. 57, in response to a participant's name being typed into box 518, a drop down menu 544 appears in window 484 beneath box 518. Menu 544 is a dynamic menu in that, as the caregiver types more letters into box 518, only those participant names matching the partially typed name are displayed in the menu 544. Thus, when the first letter of the participant's name, "M" in the illustrative example, is typed into box 518, all participants that begin with the letter "M" are shown in menu 544. Then, when the second letter of the participant's name, "i" in the illustrative example, is typed into box 518, all names that begin with the first two letters "Mi" are shown in menu 544.

If desired, the caregiver can select the desired participant name from the menu 544 before the complete name of the participant has been typed. In the illustrative example of FIG. 57, the number of names meeting the search criteria in box 518 is small enough to be displayed in menu 544 without the need for any a scroll bar, a scroll icon, or scroll arrow icons. However, if more names meet the search criteria than there is room to display in menu 544, then a scroll bar, icon, and arrows are provided to the right of menu 544. After a participant's name is selected from menu 544, the selection appears in box 518 and menu 544 disappears from screen 514.

Figure 58:
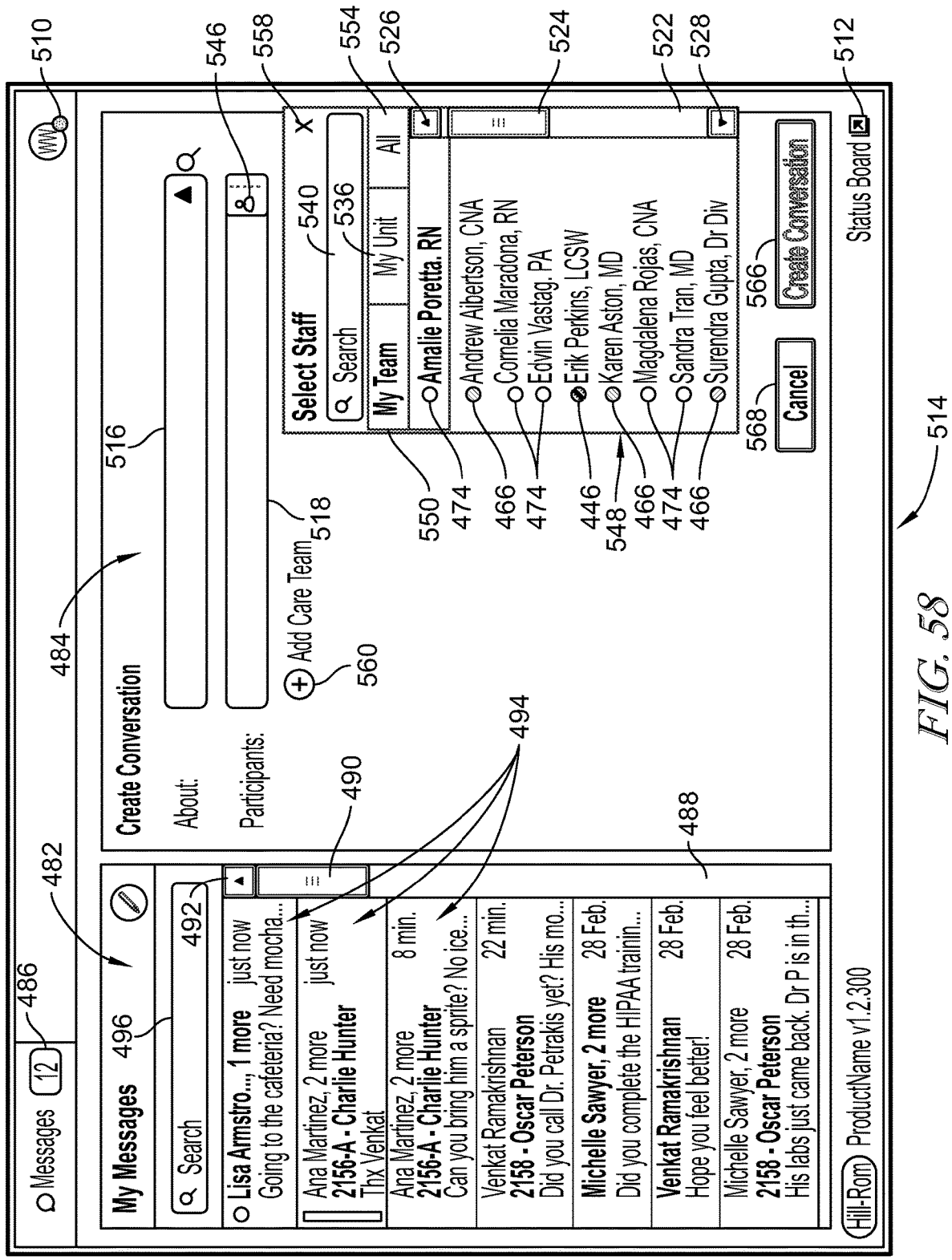
FIG. 58 is a screen shot, similar to FIG. 54, showing an example of a drop down menu of caregiver names and availability status that appears on the Create Conversation screen in response to selection of a staff icon appearing to the right of the Participants text field.

To the right of box 518 of window 484 of screen 514 is a staff search icon 546 that the caregiver can select, if desired, to bring up a menu 548 of staff names for possible selection as participants in a new conversation as shown, for example, in FIG. 58. Thus, selection of icon 546 to bring up menu 548 is an alternative way to search for one or more desired conversation participants rather than typing a participant name in box 518. As shown in FIG. 58, menu 548 includes a My Team tab 550, a My Unit tab 552, and an All tab 554. In the given FIG. 58 example, the My Team tab 550 has been selected and so menu 548 lists the staff names for the staff that have been assigned to the same team as the caregiver using the desktop computer. Selecting My Unit tab 552 results in menu 548 listing the staff names for the caregiver's unit and selecting the All tab 554 results in menu 548 listing all staff in the healthcare facility (or at least all the staff known in system 50 in connection with the caregiver and staff communication software application).

The right hand portion of menu 548 has scroll bar 522, scroll icon 524, scroll up arrow icon 526, and scroll down arrow icon 528 that operate the same in connection with menu 548 as was discussed above in connection with menu 520. Thus, the description is not repeated. Above tabs 550, 552, 554 is a search box 556 in which a staff name can be typed by the caregiver as an alternative search methodology. In some embodiments, menu 548 is dynamic and lists the staff names meeting the search criteria of the partially typed information in box 556. After a staff name is selected from menu 548, the selection appears in box 518 and menu 548 disappears from screen 514. Alternatively, if the caregiver decides not to make a selection from menu 548, then a close icon 558 is selected to close menu 532. To the left of each staff name in menu 548 is the appropriate availability icon 446, 466, 474 for each staff member based on their current availability. Icons 446, 466, 474 were discussed above in connection with FIGS. 50-52 and indicate the same availability status (unavailable or Do Not Disturb, Busy, or Available, as the case may be) in menu 548 of the desktop computer as they do on mobile devices 52.

Figure 59:
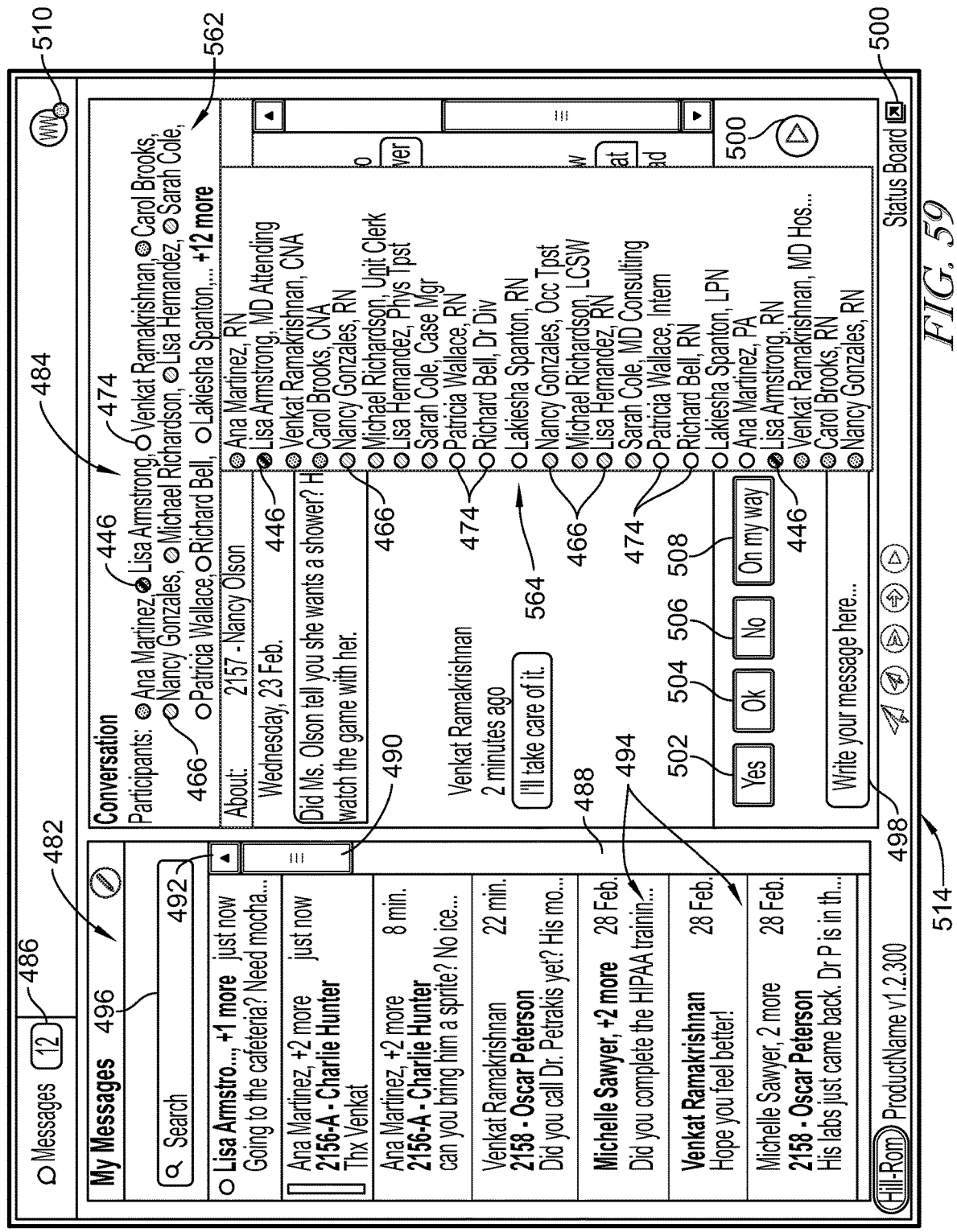
FIG. 59 is a screen shot, similar to FIG. 54, showing a list of an entire care team of Participants appearing in the Participants text field in response to an Add Care Team icon being selected on the Create Conversation screen after a patient name is added in the About text field.

As shown in FIGS. 54 and 58, window 484 of screen 514 includes an Add Care Team icon 460 that is selectable to add the caregiver's entire care team as participants in the conversation being created. As shown in FIG. 59, icon 460 has been selected and the staff names and respective availability icons 446, 466, 474 of the entire care team appears in the Participants text field at the top of window 484. In the FIG. 59 example, there are more staff members on the caregiver's care team than can fit into the allotted space of the Participants text field and so an expand list icon 562 is provided at the end of the list of staff names that are able to fit into the Participants text field. Selection of icon 562 by the caregiver results in a Care Team list 564 being shown in window 484 beneath the Participants text field. List 564 includes all of the names and respective availability status icons 446, 466, 474 of the caregiver's Care Team.

After at least one participant is listed in box 518 of window 484 of screen 514, respectively, a Create Conversation icon 566 becomes active as shown in FIGS. 54-56 and is selectable by the caregiver to begin a conversation with the one or more participants listed in box 518. FIGS. 57 and 58 show icon 566 grayed out in an inactive state due to no participants being listed in box 518 of those two figures. Alternatively, if the caregiver using the desktop computer decides that they no longer wish to create a conversation, the caregiver selects a Cancel icon 568 to abort the create conversation process. If any patient or staff information appears in boxes 516, 518 when icon 568 is selected, the information is deleted and boxes 516, 518 become empty. After the caregiver selects Create Conversation icon 566, then message box 498 and icons 500, 502, 504, 506, 508 appear at the bottom region of window 484 as shown in FIG. 59 and are used by the caregiver to create messages in the same manner as described above.

With regard to the availability status of the staff as discussed herein, the following functions are enabled or disabled as the case may be in some embodiments: 1) Available—The caregiver is logged in and can receive phone calls and text messages on their mobile devices 52; 2) Busy—The caregiver is logged in, is located in a patient room, can receive phone calls and text messages, but is not able to respond using their mobile devices 52; 3) Do Not Disturb—The caregiver is logged in, marked as unavailable, can leave voice mail and send text messages, but notification and response may not be immediate; and 4) Not Logged In—The caregiver can leave voice mail and send text messages, but responses and notifications will not be received until the next log in for the caregiver.

In some embodiments of system 50, the conversations between caregivers using mobile devices 52 and/or the desktop computer having the caregiver and staff communication software application discussed herein are stored in EMR server 94 if a patient is designated in connection with the conversation. Thus, the EMR server 94 is periodically updated with the conversations pertaining to patients having EMR records in server 94 such that the associated patient's records in server 94 each contain a record of the caregiver conversations pertaining to that patient. In other embodiments, the conversations between caregivers using mobile devices 52 and/or the desktop computer are not stored in the EMR server 94, or any server for that matter, but instead, are automatically deleted after a period of time or after ADT server 96 sends a message to mobile devices 52 and/or the desktop computer, or a server in communication with these devices, that a particular patient has been discharged from the healthcare facility.

Although certain illustrative embodiments have been described in detail above, many embodiments, variations and modifications are possible that are still within the scope and spirit of this disclosure as described herein and as defined in the following claims.

The invention claimed is:

1. A system comprising
a plurality of mobile devices carried by caregivers;
a messaging server for sending alert messages to the plurality of mobile devices;
a first nurse call server in communication with a first plurality of patient devices in a first patient room, the first plurality of patient devices being configured to generate first alert messages in response to interactions with a first patient in the first patient room, the first alert messages being communicated in a first format according to a first protocol to the messaging server which, in turn, provides first notifications to one or more mobile devices of the plurality of mobile devices,
a second nurse call server in communication with a second plurality of patient devices in a second patient room, the second plurality of patient devices being configured to generate second alert messages in response to interactions with a second patient in the second patient room, and
a configuration server in communication with the second nurse call server, the second alert messages being communicated in a second format according to a second protocol, different than the first format and first protocol, respectively, to the messaging server which, in turn, converts the second alert messages into third alert messages having the first format according to the first protocol, the third alert messages being communicated to the messaging server which, in turn, provides second notifications to one or more mobile devices of the plurality of mobile devices.

2. The system of claim 1, further comprising a Session Initiation Protocol (SIP) server and a private branch exchange (PBX) voice bridge, wherein voice communications from the plurality of mobile phones are communicated to the first nurse call server via the SIP server without involving the PBX voice bridge, and wherein voice communications from the plurality of mobile phones are communicated to the second nurse call server via the SIP server and the PBX voice bridge.

3. The system of claim 1, further comprising a publish/subscribe server that manages which mobile phones of the plurality of mobile phones are to receive each alert message of the first and third alert messages, the first alert messages from the first nurse call server and the third alert messages from the configuration server being provided to the publish/subscribe server as inputs and the publish/subscribe server sending outputs to the messaging server.

4. The system of claim 1, wherein the first plurality of patient devices comprises a first patient bed, a first pillow speaker unit, and a first patient tablet.

5. The system of claim 4, wherein the second plurality of patient devices comprises a second patient bed, a second pillow speaker unit, and a second patient tablet.

6. The system of claim 1, wherein the second plurality of patient devices comprises a patient bed, a pillow speaker unit, and a patient tablet.

7. The system of claim 1, wherein at least one mobile device of the plurality of mobile devices stores and executes a machine readable medium, the machine readable medium being non-transitory and comprising a plurality of instructions that, in response to being executed, results in a mobile device of a caregiver:
receiving at the mobile device multiple alerts relating to multiple patients assigned to the caregiver;
displaying on a display screen of the mobile device a first list of accepted alerts that the caregiver has accepted and that have not been escalated to another caregiver; and
displaying on the display screen of the mobile device a second list of escalated alerts that have been escalated to the caregiver from another caregiver.

8. The system of claim 1, further comprising a desktop computer having a display on which a Past Conversation screen is displayed, the Past Conversation screen being usable to view a past text message conversation between at least some of the caregivers about a selected patient.

9. The system of claim 8, wherein the Past Conversation screen also displays a current availability status of each of the caregivers involved in the past text message conversation.

10. The system of claim 1, further comprising a desktop computer having a display on which a Create Conversation screen is displayed, the Create Conversation screen being usable to start a text message conversation between a user of the desktop computer and one or more other caregivers about a selected patient.

11. The system of claim 10, wherein the Create Conversation screen permits selection of the patient about which the text message conversation pertains by using a first drop down menu listing all patients admitted in a unit or by using a second drop down menu that appears on the Create Conversation screen in response to typing a portion of a patient name.

12. The system of claim 10, wherein the Create Conversation screen permits selection of the one or more other caregivers to participate in the text message conversation by using a first drop down menu listing all caregivers on duty in a unit or by using a second drop down menu that appears on the Create Conversation screen in response to typing a portion of a caregiver name.

13. The system of claim 10, wherein the Create Conversation screen includes an icon that is selectable to designate all caregivers on duty in a unit as participants in the text message conversation.

14. The system of claim 10, wherein the Create Conversation screen displays an availability status of each of the caregivers involved in the text message conversation.

15. The system of claim 1, wherein the plurality of mobile devices are configured to display on a display screen of respective mobile devices a first icon indicating the corresponding caregiver's availability status for accepting more alert messages and wherein the plurality of mobile devices are further configured to display on the display screen of the respective mobile devices a second icon that is selectable by the corresponding caregiver to change the availability status.

16. The system of claim 15, wherein the plurality of mobile devices are configured to display on the display screen of the respective mobile devices a menu of availability status choices in response to selection of the second icon.

17. The system of claim 16, wherein the availability status choices include two or more of the following: All, Available, Busy, or Unavailable.

18. The system of claim 1, wherein the plurality of mobile devices are configured to display on a display screen of respective mobile devices a first selectable icon that, in response to being selected, results in the caregiver's availability status being set to an automatic mode in which the caregiver's availability is changed automatically as the caregiver moves throughout the healthcare facility.

19. The system of claim 18, wherein the plurality of mobile devices are configured to display on the display screen of the respective mobile devices a second selectable icon that, in response to being selected, results in the caregiver's availability being set to a do not disturb mode in which the caregiver is designated as unavailable.

20. The system of claim 1, wherein the plurality of mobile devices are configured to display on a display screen of respective mobile devices at least one screen that enables the caregiver to select a numerical length of time during which no new incoming alert messages will be received by the respective mobile device and during which the caregiver will be designated as unavailable.

* * * * *